US011624041B2

(12) United States Patent
Saveliev et al.

(10) Patent No.: US 11,624,041 B2
(45) Date of Patent: *Apr. 11, 2023

(54) CLEAVABLE SURFACTANTS

(71) Applicant: PROMEGA CORPORATION, Madison, WI (US)

(72) Inventors: Sergei Saveliev, Madison, WI (US); Daniel Simpson, Middleton, WI (US); Keith V. Wood, Mount Horeb, WI (US); Harry Tetsuo Uyeda, Los Osos, CA (US); Carolyn Woodroofe Hitko, Grover Beach, CA (US); Dieter Klaubert, Arroyo Grande, CA (US)

(73) Assignee: Promega Corporation, Madison, WI (US)

( * ) Notice: Subject to any disclaimer, the term of this patent is extended or adjusted under 35 U.S.C. 154(b) by 367 days.

This patent is subject to a terminal disclaimer.

(21) Appl. No.: 16/805,333

(22) Filed: Feb. 28, 2020

(65) Prior Publication Data

US 2020/0263110 A1  Aug. 20, 2020

Related U.S. Application Data

(60) Continuation of application No. 15/729,406, filed on Oct. 10, 2017, now Pat. No. 10,626,349, which is a division of application No. 12/249,584, filed on Oct. 10, 2008, now Pat. No. 9,816,054.

(60) Provisional application No. 60/979,316, filed on Oct. 11, 2007.

(51) Int. Cl.
| | |
|---|---|
| *C07C 309/15* | (2006.01) |
| *C11D 1/14* | (2006.01) |
| *C07D 307/56* | (2006.01) |
| *C11D 1/20* | (2006.01) |
| *C07C 309/10* | (2006.01) |
| *C07C 309/14* | (2006.01) |
| *C07C 309/16* | (2006.01) |
| *C07C 323/12* | (2006.01) |
| *C07C 329/06* | (2006.01) |
| *C07D 307/40* | (2006.01) |
| *C07D 317/22* | (2006.01) |
| *C07D 333/16* | (2006.01) |

(52) U.S. Cl.
CPC .............. *C11D 1/20* (2013.01); *C07C 309/10* (2013.01); *C07C 309/14* (2013.01); *C07C 309/15* (2013.01); *C07C 309/16* (2013.01); *C07C 323/12* (2013.01); *C07C 329/06* (2013.01); *C07D 307/40* (2013.01); *C07D 307/56* (2013.01); *C07D 317/22* (2013.01); *C07D 333/16* (2013.01); *C11D 1/143* (2013.01)

(58) Field of Classification Search
CPC .. C07D 307/40; C07D 307/56; C07D 317/22; C07D 333/16; C07C 309/10; C07C 309/14; C07C 309/15; C07C 309/16; C07C 323/12; C07C 329/06; C11D 1/20; C11D 1/143

See application file for complete search history.

(56) References Cited

U.S. PATENT DOCUMENTS

| | | |
|---|---|---|
| 4,360,515 A | 11/1982 | Buck |
| 4,535,108 A | 8/1985 | Rosenquist et al. |
| 5,037,729 A | 8/1991 | Furlan et al. |
| 5,232,633 A * | 8/1993 | Ilardi .................... C07C 309/12 510/159 |
| 5,846,685 A | 12/1998 | Pappas et al. |
| 6,090,250 A | 7/2000 | Mazzeo et al. |
| 6,472,496 B2 | 10/2002 | Matsumoto et al. |
| 6,828,412 B1 | 12/2004 | Brocchini et al. |
| 7,074,936 B2 | 7/2006 | Caprioli et al. |
| 7,414,076 B2 | 8/2008 | Kong et al. |
| 8,058,409 B2 | 11/2011 | Nishimura et al. |
| 9,816,054 B2 | 11/2017 | Saveliev et al. |
| 10,626,349 B2 * | 4/2020 | Saveliev ............... C07C 309/15 |
| 2004/0152913 A1 | 8/2004 | Caprioli et al. |
| 2006/0057659 A1 | 3/2006 | Bouvier et al. |
| 2009/0095628 A1 | 4/2009 | Saveliev et al. |

FOREIGN PATENT DOCUMENTS

| | | |
|---|---|---|
| EP | 0519942 | 10/1994 |
| GB | 1415349 | 11/1975 |
| WO | WO 1991/13610 | 9/1991 |
| WO | WO 1994/00425 | 1/1994 |
| WO | WO 2000/70334 | 11/2000 |

(Continued)

OTHER PUBLICATIONS

Tilley et al. Tyrosine-selective protein alkylation using Allylpalladium complexes. J. Am. Chem. Soc. 2006, vol. 128, pp. 1080-1081. (Year: 2006).*

Chen, E.I. et al., "Optimization of mass spectrometry-compatible surfactants for shotgun proteomics," J. Proteome Res. (2007) 9:2529-2538.

(Continued)

*Primary Examiner* — Shafiqul Haq
(74) *Attorney, Agent, or Firm* — Anne M. Reynolds; Casimir Jones, S.C.

(57) ABSTRACT

The invention provides surfactant compounds of formulas I-IX, which can be used in methods for aiding the solubilization, digestion, preparation, analysis, and/or characterization of biological material, for example, proteins or cell membranes. The compounds can also aid in the recovery of peptides generated during protein digestion, particularly for in-gel digestion protocol. Additionally, the compounds can improve enzymatic protein deglycosylation without interfering with downstream sample preparation steps and mass spectrometric analysis. The compounds can be specifically useful as digestion aids that can be decomposed by an acid, by heat, or a combination thereof. Decomposition of the surfactants allows for facile separation from isolated samples, and/or allows for analysis of the sample without interfering with the sensitivity of various analytical techniques.

16 Claims, 29 Drawing Sheets

(56) References Cited

FOREIGN PATENT DOCUMENTS

| WO | WO 2002/44324 | 6/2002 |
|---|---|---|
| WO | WO 2002/083829 | 10/2002 |
| WO | WO 2003/102225 | 12/2003 |
| WO | WO 2004/048507 | 6/2004 |
| WO | WO 2008/001888 | 1/2008 |
| WO | WO 2009/048611 | 4/2009 |

OTHER PUBLICATIONS

Epstein, W.W. et al., "The synthesis of a photolabile detergent and its use in the isolation and characterization of protein," Anal. Biochem. (1982) 119(2):304-312.
Hellberg, P-E. et al., "Cleavable surfactants," J. Surfactants and Detergents (2000) 3(1):81-91.
Hervey, W.J. et al., "Comparison of digestion protocols for microgram quantities of enriched protein samples," J. Proteome Res. (2007) 6(8):3054-3061.
Koenig, S et al., "Sodium dodecyl sulfate versus acid-labile surfactant gel electophoresis: comparative proreomic studies on rat retina and mouse brain," Electrophoresis (2003) 24(4):751-756.
Kraft, P. et al., "Mass spectrometric analysis of cyanogen bromide fragments of integral membrane proteins at the picomole level: application to rhodopsin," Anal. Biochem. (2001) 292:76-86.
Mohlin, K. et al., "Nonionic ortho ester surfactants as cleavable emulsifiers," J. Colloid and Interface Science (2006) 299:435-442.
Nomura, E. et al., "Acid-labile surfactant improves in-sodium dodecyl sulfate polyacrylamide gel protein digestion for matrix-assisted laser desorption/ionization mass spectrometric peptide mapping," J. Mass Spectro. (2004) 202-207.
Norris, J.L. et al., "Mass spectrometry of intracellular and membrane proteins using cleavable detergents," Anal. Chem. (2003) 75(23):6642-6647.
Puschel, F. et al., "Zusammenhange swischen der konstitution und einigen eigenschaften von grenzflachenaktiven benzolsulfonated mit heteroatomen in der aliphatischen seitenkette," Tenside (1970) 7:249-253.
Ross, A.R. et al., "Identification of proteins from two-dimensional polyacrylamide gels using a novel acid-labile surfactant," Proteomics (2002) 2(7):928-936.
Sergei, S. et al., "Improve protein analysis with the new mass spectrometry-compatible proteas MAX surfactant," Promega Notes No. 99 (May 1, 2008) 3-7.
Tehrani-Bagha, A. et al., "Cleavable surfactants," Curr. Opin. Colloid and Interface Sci. (2007) 12(2):81-91.
Urban, J. et al., "Synthesis of potassium 4-(alkoxycarbonylthio)- and 4 (alkoxythiocarbonylthio)-3,5-dinitrobenzenesulfonates as amphiphiles," Synth. Comm. (1990) 20(20):3201-3206.
Wada, Y. et al., "In-gel digestion with endoproteinase LysC," J. Mass Spectrom. (2003) 38(1):117-118.
Yu, Y-Q., et al., "Enzyme-friendly, mass spectrometry-compatible surfacant for insolution enzymatic digestion of proteins," Anal. Chem. (2003) 75(21):6023-6028.
Zeller, M. et al., "Use of an acid-labile surfactant as an SDS substitute for gel electrophoresis and proteomic analysis," J. Biomol. Tech. (2002) 13(1):1-4.
Zhong, H. et al., "Protein sequencing by mass analysis of polypeptide ladders after controlled protein hydrolysis," Nature Biotech. (2004) 22(10):1291-1296.
International Search Report and Written Opinion for Application No. PCT/US2008/011644 dated May 7, 2009 (25 pages).
Invitation to Pay Additional Fees and Partial Search Report for Application No. PCT/US2008/011644 dated Mar. 9, 2009 (12 pages).
European Patent Office Action for Application No. 08838555.4 dated Mar. 22, 2011 (6 pages).
European Patent Office Action for Application No. 12189625.2 dated Mar. 4, 2013 (13 pages).
United States Patent Office Action for U.S. Appl. No. 12/249,584 dated Apr. 11, 2011 (9 pages).
United States Patent Office Action for U.S. Appl. No. 12/249,584 dated Nov. 30, 2011 (12 pages).
United States Patent Office Action for U.S. Appl. No. 12/249,584 dated Dec. 6, 2012 (16 pages).
United States Patent Office Action for U.S. Appl. No. 12/249,584 dated Apr. 4, 2016 (10 pages).
European Patent Search Report for Application No. 12189625.2 dated Jun. 19, 2013 (19 pages).
Japanese Patent Office Action for Application No. 2010-528892 dated Sep. 2, 2013 (5 pages).
Japanese Patent Office Action for Application No. 2010-528892 dated Apr. 26, 2014 (3 pages, English translation only).
European Patent Office Action for Application No. 12189625.2 dated Jun. 13, 2014 (4 pages).
United States Patent Office Final Action for U.S. Appl. No. 12/249,584 dated Nov. 10, 2016 (15 pages).
United States Patent Office Action for U.S. Appl. No. 12/249,584 dated Jul. 7, 2017 (8 pages).

* cited by examiner

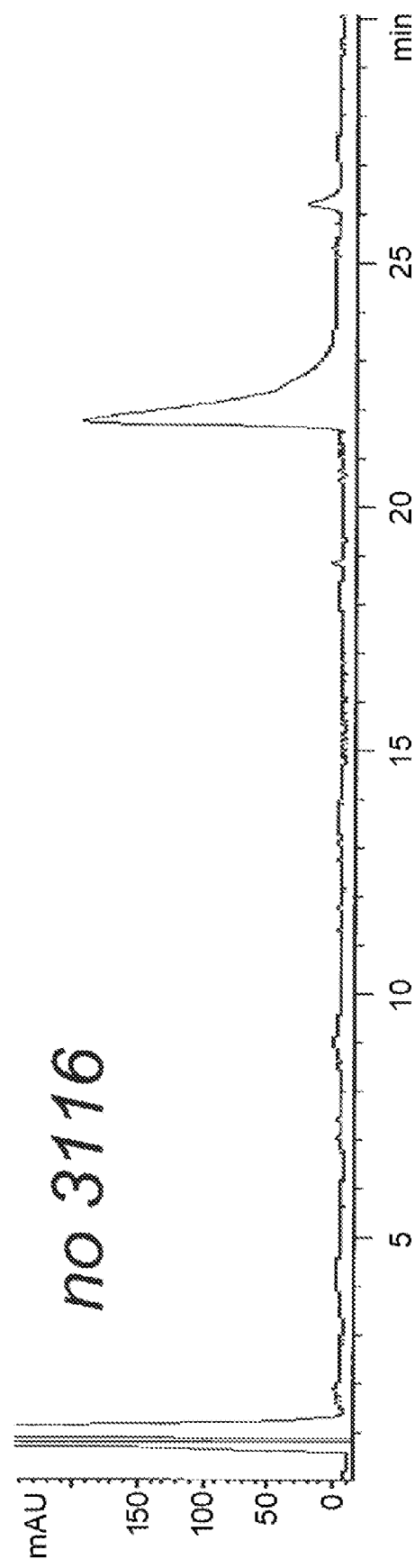
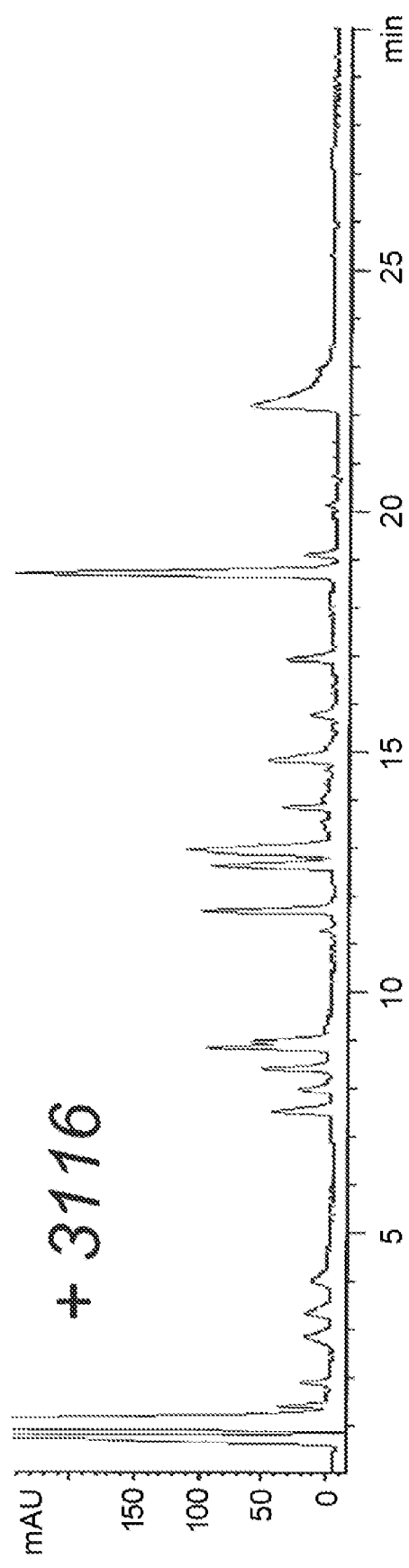
FIG. 3(a)
FIG. 3(b)

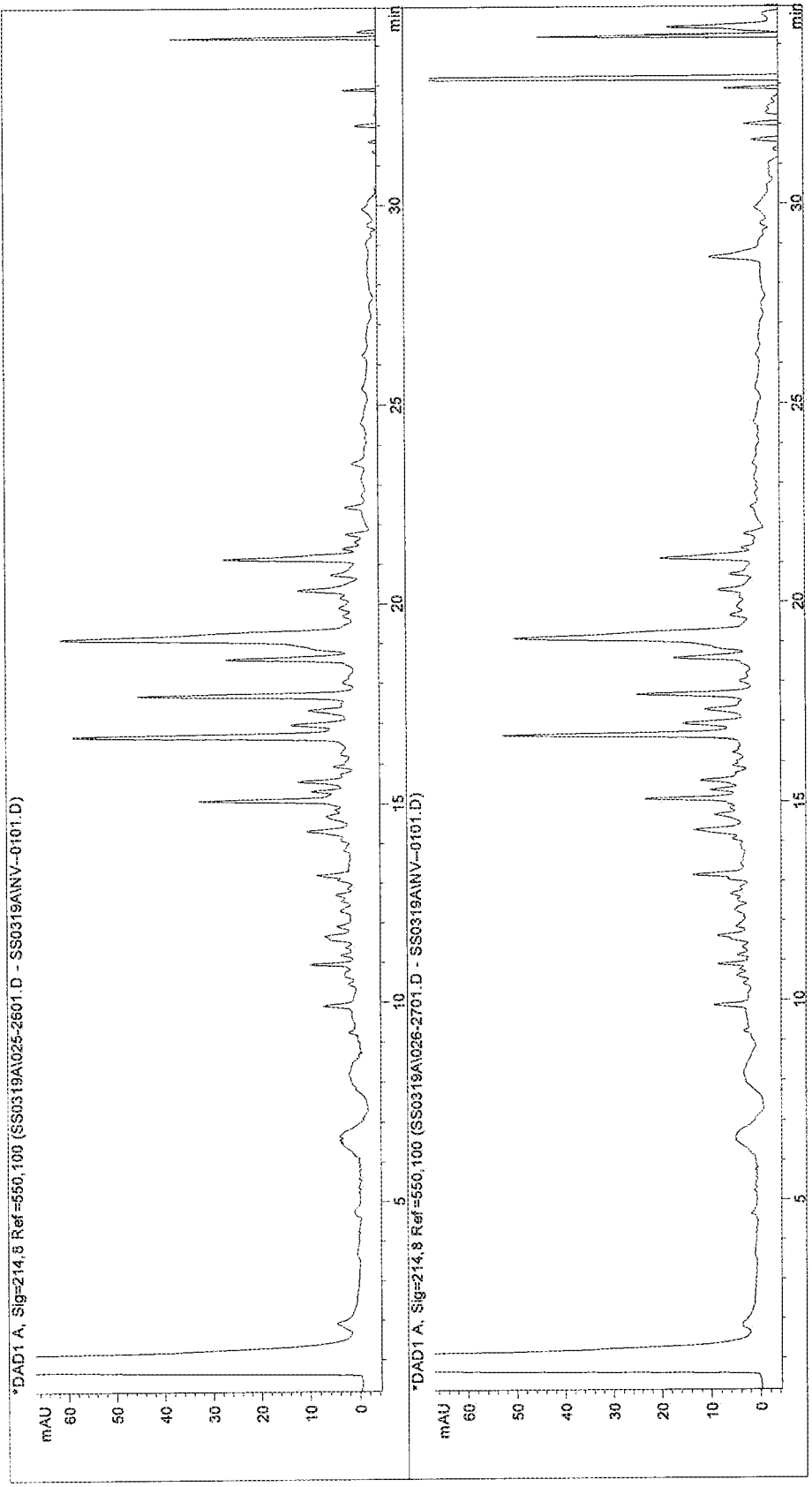

Compound 3271: Bacteriorhodopsin/Chymotrypsin digest

CLEAVABLE SURFACTANTS

RELATED APPLICATIONS

This application is a continuation of U.S. patent application Ser. No. 15/729,406, filed Oct. 10, 2017, now U.S. Pat. No. 10,626,349, issued Apr. 21, 2020, which is a divisional of U.S. patent application Ser. No. 12/249,584, filed Oct. 10, 2008, now U.S. Pat. No. 9,816,054, issued Nov. 14, 2017, which claims priority under 35 U.S.C. § 119(e) to U.S. Provisional Patent Application No. 60/979,316, filed Oct. 11, 2007, the contents of each of which are incorporated herein by reference.

BACKGROUND OF THE INVENTION

The preparation of protein samples for analysis, for example, mass spectrometry analysis, typically includes three main steps: solubilization, digestion, and peptide recovery. Current methods and reagents applied to one step are rarely compatible with the following step. For example, solubilizing agents such as surfactants (e.g., sodium dodecyl sulfate (SDS)) or denaturants (e.g., acetonitrile, urea, or guanidine) typically inhibit the proteases, such as trypsin, that are used in the digestion that follows solubilization. Even when used in concentrations that can be tolerable for trypsin activity, the presence of these surfactants or denaturants interfere with subsequent analyses, such as liquid chromatography or mass spectrometric analysis. Accordingly, removal of the surfactants and organic solvents is typically required before conducting further analysis on a sample (e.g., proteins or peptides). The manipulations required for removal of these reagents complicates the sample preparation process and often leads to loss of sample material.

The digestion step frequently presents a major challenge in protein sample preparation. A typical protein digestion with trypsin requires overnight incubation to reach completion. Even after overnight incubation, some proteins that are resistant to digestion, such as membrane proteins, can remain intact, thus requiring extraordinary conditions to achieve satisfactory digestion. Current methods employed in an attempt to overcome these limitations and to speed the digestion process include the use of organic solvents (e.g., acetonitrile), elevated temperatures, denaturants (e.g., urea), and/or detergents (e.g., SDS) to improve protein solubilization and protein denaturation, thus improving digestion. However, these alternative methods and additives often result in incomplete cleavage and low reproducibility, limiting their utility. The use of these reagents also leads to inhibition of trypsin activity, interference with HPLC separation, and suppression of peptide detection in mass spectrometry.

In-gel protein digestion brings specific challenges to protein sample preparation. Success of in-gel digestion relies not only on efficient protein digestion but also on efficient post-digestion peptide extraction from the gel. Peptide extraction from the gel can be lengthy and laborious and it is often only moderately efficient in terms of peptide recovery. Recovered peptides are generally limited to the size of about 2,500 Da. Longer peptides are largely trapped in the gel. See "In-gel digestion with endoproteinase Lys-C", Y. Wada, M. Kadoya, *J. of Mass Spectrom.* 2003; 38: 117-118. Recovery of peptides with increased hydrophobicity is also impacted.

Other procedures related to protein sample preparation include analysis of post-translational protein modifications. About 60% of all human proteins are glycosylated. Glycosylation was shown to play important role in many key cellular mechanisms. To analyze glycosylation, a glycan should be separated from a protein. This removal, referred to as deglycosylation, is performed by using glycosidases. Deglycosylation is frequently a time-consuming process. Reagents such as sodium dodecyl sulfate (SDS) can dramatically improve deglycosylation, potentially by providing better access to glycan attachment sites for the glycosidases. However, SDS interferes with downstream sample preparation steps, mass spectrometric analysis, and HPLC analysis.

Accordingly, there is a need for improved methods for protein sample preparation. There is also a need for methods or reagents that benefit one or more of the three major protein preparation steps: solubilization, digestion, and peptide recovery, in order to streamline the protein sample preparation process. Preferably, these methods or reagents would not lead to the inhibition of protease activity, and would not interfere with isolation and/or characterization techniques. There is a particular need to streamline in-gel digestion protocols and to improve recovery of peptides from gels. Finally, there is a need for improved methods of protein deglycosylation that do not interfere with downstream sample preparation and mass spectrometric analysis of proteins and glycans.

SUMMARY

The invention provides surfactant compounds useful for aiding the solubilization, digestion, analysis, and/or characterization of biological material, for example, proteins. The compounds can also aid in the recovery of peptides generated during protein digestion. The compounds can improve enzymatic protein deglycosylation without interfering with downstream sample preparation steps and mass spectrometric analysis. The compounds are specifically useful as digestion aids that can be decomposed by an acid, by heat, or a combination thereof. Decomposition of the surfactants allows for facile separation from isolated samples, and/or allows for analysis of the sample without interfering with the sensitivity of various analytical techniques.

The surfactant compounds can also enhance the stability and reactivity of proteases, for example, trypsin and chymotrypsin, thus providing a method for faster and more efficient cleavage of peptide bonds in a sample. This increased stability and/or reactivity of the protease can therefore reduce the amount of protease required for effective sample digestion, and reduce the amount of time required for the digestion. The reduction of time required for digestion thus provides a method amenable to rapid on-line, automated digestion and analysis.

Accordingly, the invention provides methods for solubilization of proteins, including highly hydrophobic proteins (i.e., membrane proteins), protease-assisted protein digestion for proteins, for example, for proteins 'in solution', and for proteins 'in-gel'. The method includes combining a sample (in gel or in solution) and a protease with a surfactant compound of the invention. The protease can be any suitable protease for a given purpose, for example, trypsin or chymotrypsin. Other suitable proteases include serine proteases, threonine proteases, cysteine proteases, aspartic acid proteases (e. g., plasmepsin), metalloproteases, glutamic acid proteases, or a combination thereof.

The invention also provides methods for improved recovery of peptides obtained in in-solution and in-gel digestion protocols. The surfactants described herein can achieve the improved recovery by preventing peptide loss due to absorption or adsorption by glassware and plastic-ware, and/or by preventing peptide loss due to precipitation, and by allowing for improved extraction of peptides from a gel matrix for in-gel digestion.

For in-gel protein digestion, the surfactants described herein can streamline the sample preparation protocol by combining protein digestion and peptide extraction into a single step. The digestion and extraction can be completed within about one hour. The resulting efficiency represents a significant improvement over conventional in-gel protocol, which typically require overnight digestion followed by 2-3 hours of peptide extraction.

The surfactants described herein can also improve protein recovery in protein extract depletion methods, such as plasma depletion methods. In the depletion method, abundant proteins are removed from the protein extract or plasma. This improves analysis of low abundant proteins, detection of which is frequently compromised due to dominant interference with highly abundant proteins. The disadvantage of typical depletion methods is loss of substantial amount of low abundant proteins, which are nonspecifically absorbed by highly abundant proteins. The surfactants described herein can disrupt this nonspecific absorption. In contrast to commonly used surfactants and detergents, the surfactants described herein lessen or eliminate impact to downstream applications, such as mass spectrometry, because the surfactants of the invention can degrade during the sample preparation protocol.

Additionally, the surfactants described herein can provide a convenient 'self-degrading' mode of action (i.e., they can degrade by hydrolysis in solution during the protocol). This 'self-degrading' mode of action has not been shown by currently known reagents used in protein sample preparation, wherein the surfactants self-degrade by the end of the sample preparation protocol. This offers a convenient method of using the surfactants for the sample preparation, in which no degradation of the surfactant is required after sample preparation protocol is complete.

Accordingly, the invention provides compounds of formulae I-IX, for example, a compound of formula I:

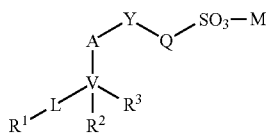

(I)

wherein:

Q is $(C_1-C_6)$alkyl, $(C_6-C_{10})$aryl, $(C_5-C_{10})$heteroaryl, or $(C_6-C_{10})$aryl-NH$(C_1-C_6)$alkyl;

Y is O, S, NH, —X—C(=O)—, —C=N—, carbonyl, or —O—C(=Z)—X—;

A is aryl, aryl$(C_1-C_6)$alkyl, heteroaryl, or a direct bond;

Z is O or S;

X is O, NH, or S;

V is C or N;

M is H, an alkali metal, or tetra$(C_1-C_{20})$alkylammonium;

L is —X—C(=Z)—X— or a direct bond;

$R^1$ is $(C_4-C_{20})$alkyl, $(C_2-C_{20})$alkenyl, $(C_6-C_{16})$aryl, $(C_5-C_{10})$heteroaryl, $(C_1-C_{20})$alkoxy$(C_1-C_{20})$alkyl, $(C_1-C_{12})$alkyl $(C_6-C_{20})$polyalkoxy, or $(C_6-C_{20})$(alkylthio)-$(C_1-C_6)$alkyl, or absent when V is N;

$R^2$ and $R^3$ are each independently H or $(C_1-C_{20})$alkyl; or $R^2$ and $R^3$ together form a 3-8 membered carbocycle ring, or a 3-8 membered heterocyclic ring comprising 1, 2, or 3 N($R^x$), S, or O; or —V($R^2$)($R^3$)-L-$R^1$ is optionally —O—$R^1$ when A is aryl;

wherein any alkyl, alkenyl, aryl, or heteroaryl, carbocyclic ring, or heterocyclic ring, is optionally substituted with one or more (e.g., 1, 2, 3, 4, or 5) $(C_1-C_{20})$alkyl, $(C_2-C_{20})$alkenyl, $(C_2-C_{10})$alkynyl, $(C_3-C_{10})$cycloalkyl, $(C_1-C_{20})$alkoxy, $(C_1-C_{20})$alkylcarbonyl, $(C_1-C_{20})$alkylcarboxyl, halo, hydroxyl, —CO$_2R^x$, —SO$_2R^x$, —SO$_3R^x$, nitro, amino, N($R^x$)$_2$, mercapto, $(C_1-C_{20})$alkylthio, $(C_6-C_{16})$aryl, $(C_6-C_{30})$arylthio, trifluoromethyl, =O, heteroaryl, or heterocycle groups; provided that Q is not substituted with CO$_2$H; and each $R^x$ is independently H, $(C_1-C_6)$alkyl, $(C_6-C_{16})$aryl, or $(C_1-C_6)$alkyl-$(C_6-C_{16})$aryl;

or a salt thereof.

One embodiment includes methods for analyzing a sample, including contacting the sample with a surfactant compound of formula I. In certain embodiments, the method includes analyzing the sample by high performance liquid chromatography. In various embodiments, the method includes analyzing the sample by mass spectrometry. In some embodiments, the method includes analyzing the sample by ion-pair liquid chromatography.

Another embodiment provides a method for performing electrophoresis that includes contacting a sample with a surfactant compound of Formula I. The electrophoresis can be gel electrophoresis, for example, polyacrylamide gel electrophoresis, including tube, slab gel and capillary formats of polyacrylamide gel electrophoresis. The electrophoresis can be free zone electrophoresis or capillary electrophoresis. The methods can include degrading the surfactant after electrophoresis. The methods can also include degrading the surfactant after electrophoresis with an acidic solution, with heat, or a combination thereof. The methods can further include purifying the sample after degrading the surfactant.

The invention also provides a kit for performing analysis of a biomaterial sample that includes a surfactant compound of formula I. The kit can include a component for degrading the surfactant, and optionally a molecular weight standard. The kit can also include a staining reagent. In certain embodiments, the surfactant is incorporated into a gel medium in the kit. The kit can optionally include a plastic in-gel digestion device, an enzyme, such as a protease, for example a serine protease, such as trypsin, or chymotrypsin, or Lys-C, or a glycosidase, for example, PNGase F. The kit can also optionally include C18 clean-up tips, and reagents such as chemical tags and/or iodoacetamide.

Additionally, the invention provides a method for enhancing chemical digestion of a biomolecule, including contacting the molecule with a digestive enzyme and a surfactant compound of formula I, to thereby enhance the chemical digestion of the molecule.

The invention also provides methods of making the surfactant compounds of the invention, and provides intermediates used in their preparation.

The invention also provides a method for recovery of peptides after a digestion (in-solution or, in alternatively, in-gel) is complete. The method allows for a dramatic increase in peptide yield resulting from improved peptide extraction from a gel (in in-gel digestion) and from preventing peptide loss due to absorption by glassware or plastic-ware, or due to precipitation (in both in-solution and in-gel digestions). Peptides extracted from gels are generally limited to the size of about 2,500 Da. Longer peptides largely remain trapped in the gel. Recovery of peptides with increased hydrophobicity is also impacted. The method allows for increased recovery of longer and more hydrophobic peptides in amounts amenable for advanced analysis, such as MS/MS. Additionally, the method can improve the quality of protein analysis by preserving acid-labile amino acids and acid-labile post-translational modifications.

The invention also provides a method to combine in-gel protein digestion and peptide extraction into a single step comprising contacting a protein-containing gel with an aqueous solution that contains a protease and a compound of the invention, whereby a protein in the gel solubilizes and unfolds to allow for digestion by the protease in the aqueous solution, and separating the aqueous solution that contains digested peptides extracted from the gel. The presence of the compound of the invention can improve and accelerate the digestion of the protein in the gel, compared to known surfactants, and simultaneously enhances the extraction of the digested peptides from the gel and eliminates the need for further extraction.

Additionally, the invention provides a method for enhancing enzymatic deglycosylation of glycoproteins. Use of the surfactants described herein can achieve the enhancing enzymatic deglycosylation of glycoproteins without interfering with downstream sample preparation steps and mass spectrometric analysis.

Although certain aspects, embodiments, drawings and elements of the invention are described herein, they are meant to be illustrative and not limiting. For example, one of ordinary skill in the art will be able to establish equivalents to certain elements herein, and those equivalents are considered to be within the spirit and scope of the present invention.

BRIEF DESCRIPTION OF THE DRAWINGS

The following drawings form part of the present specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 3A and FIG. 3B illustrate the stimulation of protein digestion according to one embodiment, using compound 3116. FIG. 3A shows an HPLC chromatogram after overnight incubation of horse myoglobin with trypsin in the absence of 3116. FIG. 3B shows an HPLC chromatogram after one hour of incubation of horse myoglobin with trypsin in the presence of 3116.

FIG. 7A shows a spectrum of peptides extracted into a digestion mixture after overnight digestion of Bovine Serum Albumin (BSA) without the aid of a surfactant of the invention. FIG. 7B shows a spectrum of peptides extracted into a digestion mixture after 1 hour of digestion with the aid of a surfactant described herein, according to an embodiment of the invention.

FIG. 8A shows the mass spectrum without the aid of surfactant 3211, where the protein was incubated overnight, and then peptides were extracted according to the peptide extraction protocol. FIG. 8B shows the mass spectrum with the aid of surfactant 3211, according to one embodiment, where the protein digestion and peptide extraction was complete in a single 1 hour step. Peptides were concentrated with C18 clean-up tips and analyzed using MALDI-TOF mass spectrometry.

In FIG. 13A, FIG. 13B and FIG. 13C, the upper chromatogram is the RapiGest™ surfactant assisted digestion reaction (control) and the lower chromatogram is the result obtained with compound 3211. Typical reaction and HPLC conditions are described in Example 12.

FIG. 17B illustrates the comparative effect of compound 3266 to aid in the solubilization and digestion of Bacteriorhodopsin with Chymotrypsin as compared with the commercially available surfactant RapiGest™. In both FIG. 17A and FIG. 17B, the upper chromatogram is the RapiGest™ surfactant assisted digestion reaction (control) and the lower chromatogram is the result obtained with compound 3266. Typical reaction and HPLC conditions are described in Example 12.

DETAILED DESCRIPTION

Figure 1:
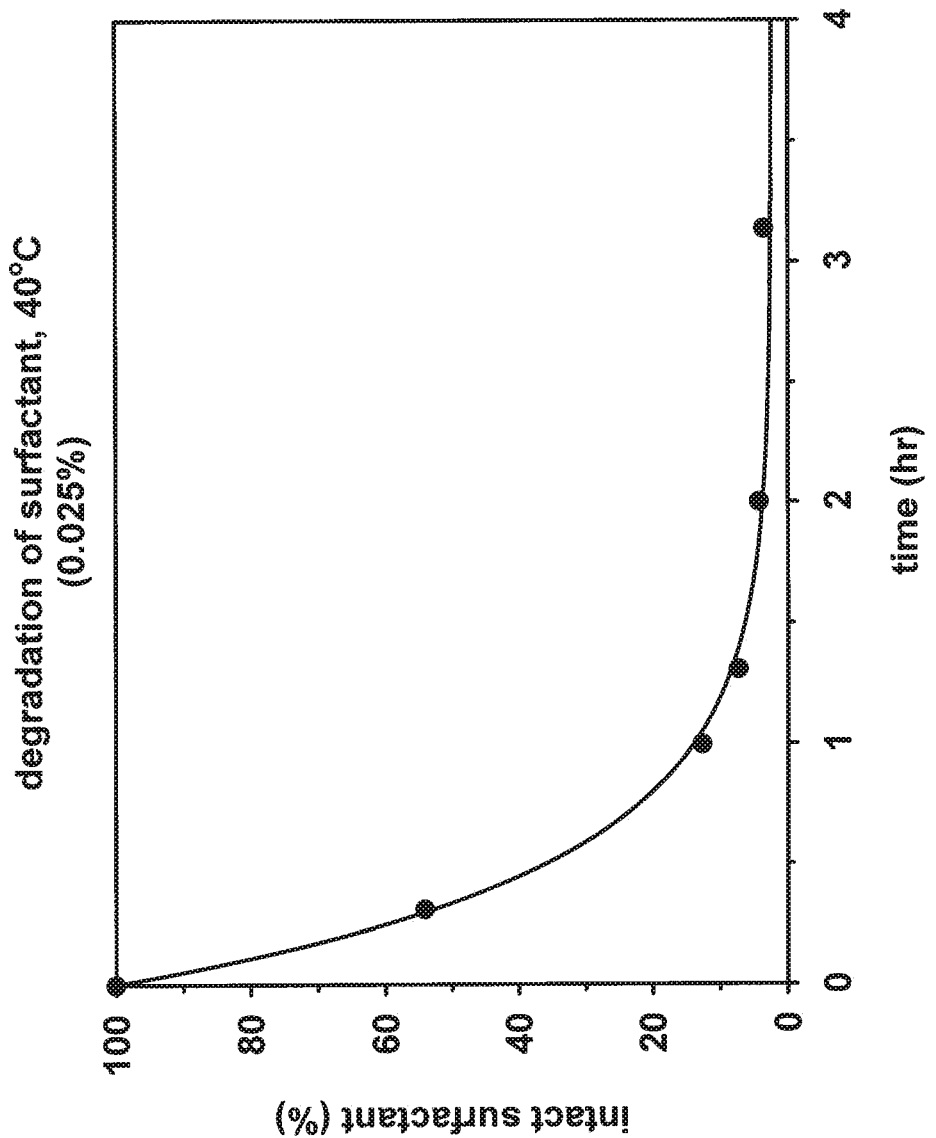
FIG. 1 illustrates the degradation profile of a 0.025% solution of surfactant 3211 at 40° C., according to one embodiment.

Many analytical systems are sensitive to the presence of surfactants. For example, SDS and triton surfactants suppress the analyte signal during matrix assisted laser desorption ionization mass spectrometry (MALDI-MS) analysis. Signal suppression from surfactant contamination is contemplated to result from physical and chemical blockage of the ionization/desorption process of MALDI-MS. Surfactant compositions and methods suitable for MALDI-MS analyses, and other analyses, of hydrophobic molecules including natural and synthetic polymers and polypeptides/proteins, are of significant interest to researchers working with biomaterials.

This invention relates to the treatment of a sample, such as a tissue section, protein, or protein extract from a plant or animal, or other organism, with a compound or mixture of compounds that can perform multi-functional roles in the preparation of these samples for analysis, e.g., mass spectrometry or chromatography, at designed times determined by treatment conditions. These compounds can function as a surfactant in helping solubilize hydrophobic or other non-soluble compounds, or they can help to unfold (denature) proteins, thereby drastically accelerating and improving protein digestion with proteases.

The surfactant compounds disclosed herein can also function as enhancers of enzymatic deglycosylation of glycoproteins. Finally, the surfactant compounds can aid the recovery of generated peptides by improving peptide extractions from a gel (in in-gel digestion) and by preventing peptide loss due to absorption by labware, or due to precipitation. Due to built-in cleavable bonds, appropriate treatment of the sample, for example, with acid, base, heat, etc., can then cause decomposition of the agent to two or more smaller parts, each of which does not materially interfere with the analysis.

The resulting degraded products can often be removed from the sample more readily than the original surfactant compound. In addition, mass spectrometric sensitivity of the molecules can be significantly greater in the presence of the surfactants than in the presence of SDS at similar concentrations, even in the presence of these degraded products. The invention thus has applicability in a variety of techniques that benefit from the initial presence and concomitant removal of a surfactant.

The invention aids in solving problems in the art associated with analysis of proteins and peptides. Many analytical systems function best when samples are aqueous or the molecules being analyzed in the sample are solubilized in an aqueous environment. For example, bringing proteins to a soluble state is a requirement for efficient protein digestion. Also, maintaining peptides in a soluble state is a requirement for efficient analysis by mass spectrometry or liquid chromatography.

Mass spectrometric analysis of hydrophobic molecules or molecules with significant hydrophobic regions (e.g., proteins or peptides) can be difficult or problematic using currently known techniques. These molecules are difficult, or sometimes essentially impossible, to suspend in aqueous solution. They tend to aggregate and precipitate out of solution as the hydrophobic domains interact in a manner to minimize contact with the aqueous environment of typical MS samples preparations. The surfactants described herein can prevent these effects.

Molecules of commercial importance include polymers, hydrophilic or hydrophobic, with a particular advantage for hydrophobic polymers, such as certain constituents of hydrophobic polypeptides, for example membrane associated proteins and cellular components. The typical approach to manipulating such molecules is to apply surfactants to bring the hydrophobic molecule of interest out of its native environment and into a more aqueous environment. Surfactants generally include a hydrophilic (or polar) head group and a hydrophobic tail. They may arrange about a hydrophobic molecule with the tails interacting with hydrophobic areas on the molecule and the polar head group interacting with water in the environment.

For example, receptor proteins are often associated with or inserted into the plasma membrane of a cell and are generally hydrophobic in nature (at least the lipid associated portions thereof). Surfactants can be useful to isolate the receptor protein away from the plasma membrane. However, certain surfactants have also been known to interfere with MALDI-MS analysis. The addition of common surfactants, such as sodium dodecyl sulfate, triton surfactants, and Tween, essentially eliminates a molecular signal generated by MALDI-MS, as well as electrospray ionization MS. Accordingly, the present invention provides compositions and methods that solve these and other problems of the art.

Accordingly, the surfactants described herein offer a significant improvement to protein sample preparation protocol. They improve solubilization, digestion, deglycosylation, and peptide recovery. They achieve these effects on protein sample preparation protocol without interfering with downstream sample preparation steps such as liquid chromatography and mass spec analysis. Additionally, the surfactants described herein can provide a novel, self-degrading mode of action in which no special manipulation of the surfactants (i.e., acid- or thermal degradation) is required after the sample preparation protocol is complete.

A. Enzyme-Compatible Degradable Surfactants

The invention provides acid-labile and thermolabile surfactants that dramatically accelerate protein digestion. The surfactants solubilize and denature proteins intended for digestion without inhibiting trypsin activity. The surfactants allow for rapid digestion of proteins, including the membrane protein bacteriorhodopsin. An acid- and thermolabile site in the surfactant allows for facile removal from solution. The surfactants can be designed, and the protocol conditions can be optimized, in a way that the surfactants degrade within the digestion reaction time period, thus eliminating the requirement for a separate degradation step.

In the event that the digestion protocol is modified (for example, if a user digests proteins in shorter period than recommended) and some amount of the surfactants is still present, the surfactant can be readily degraded with a small amount of acid or by heat, and removed by centrifugation, or by solid phase extraction (e.g. by using an Omix® tip from Varian, Inc.). The acid or thermal degradation technique can render the surfactant innocuous to downstream liquid chromatography and mass spectrometry analysis. Experiments have shown that the peptides can then be directly analyzed with mass spectrometry with no detectable interference from the degraded detergent.

The detergent accelerates digestion by unfolding proteins thus providing access to internal protein sites for trypsin. Furthermore, experimental data also suggest that the detergent dramatically stabilizes trypsin. In various experiments, trypsin was found to retain a high level of activity for hours of incubation in the presence of the detergent, whereas it gradually lost activity in the absence of the detergent.

The stimulating effect of the surfactants is not only limited to trypsin. The surfactants also accelerated protein digestion with chymotrypsin. Chymotrypsin is a commercially important protease because it is increasingly used to digest membrane proteins. It is likely that the surfactants are compatible with many commercially important proteases and can be used broadly as general protease enhancers.

In addition to improving protein digestion and stabilizing trypsin, the surfactants have good solubilizing properties. The membrane protein bacteriorhodopsin, which is insoluble in aqueous solutions, has been efficiently solubilized in the presence of the surfactants. Therefore, the surfactants are useful not only for protein digestion, but potentially for extraction of membrane and other hydrophobic proteins from cells tissues.

The invention also provides a method for recovery of peptides after digestion (in-solution or in-gel) is complete. This surfactant assisted method allows for an increase in peptide yield resulting from improved peptide extraction from gel (in in-gel digestion) and preventing peptide loss due to absorption by glassware or plastic-ware, or due to precipitation (for both in-solution and in-gel digestions). The method also simplifies peptide extraction steps for in-gel digestion by combining digestion and extraction into a single step and better preserves acid-labile amino acids and acid-labile post-translational modifications. Additionally, the invention provides a method for enhancing enzymatic deglycosylation of glycoproteins. The invention can achieve this enhancing without interfering with downstream sample preparation steps and/or mass spectrometric analysis.

B. Thermolabile Surfactants for Protein Analysis

While acid degradation is a simple and efficient way to remove surfactants from peptide solution, under certain conditions the acid can cause unwanted side effects such as cleavage of acid-labile post-translational protein modifications (PTMs) or cleavage of acid-labile peptide bonds. A supplemental approach has been developed that retains all the advantages offered by acid-labile surfactants for protein analysis but does not require acid to degrade the surfactant structure. These new surfactants have excellent protein solubilizing properties and dramatically improve protein digestion.

After digestion is complete, the surfactant can be degraded by simply increasing the reaction temperature. In addition, the thermolabile properties provide a substantially unique 'self-degrading' mode of action (i.e., they can degrade by hydrolysis in solution during the protocol). With this self-degrading mode, not shown with any currently used reagent for protein sample preparation, the surfactants can self-degrade by the end of the sample preparation protocol. This mode offers a convenient method of using the surfactants for sample preparation where no further manipulation is required for degradation of the surfactant after sample preparation protocol is complete.

For example, degradation of surfactant compound 3211 after protein digestion is not required because the surfactant degrades during the digestion process. The stability of a 1% solution of 3211 (10% degradation) is 8 hours at 23° C., 12 days at 4° C., and an estimated >3 years at −20° C. However, the degradation rate of surfactant 3211 increases in a typical protein digestion protocol. FIG. 1 shows the degradation profile of a 0.025% solution of surfactant 3211 at 40° C. Less than about 5% of intact surfactant remains after only 2 hours.

When necessary, the surfactants can be degraded within a few minutes at temperatures above about 90° C., or within about 20-30 minutes at lower temperature (e.g., about 65° C.). For example, when working with a sufficiently robust sample, boiling the surfactant composition for 2-3 minutes completely degrades the thermolabile surfactants. In other instances, the surfactant completely degrades by the end of the digestion reaction time period, and the sample can be readily analyzed, for example, by mass spectrometry or chromatography. As degradation typically occurs at neutral pH (in the digestion buffer), the surfactants disclosed herein allow for better preservation of acid-labile or alkali-labile PTMs. In addition, by eliminating the need for the addition of acids, the degradation protocol is rendered more user-friendly.

While an acid is not required to degrade the peptides of interest, lowering the reaction pH with acid can accelerate the degradation process and allow rapid degradation at lower temperatures (e.g., about 37° C.). Thus the surfactants disclosed herein offer at least two different means (temperature and acid) for rendering the surfactants innocuous. In addition, the ability to heat degrade the surfactant offers additional options to deactivate the protease following digestion, offering further alternatives to a protease digestion format.

As used herein, the following terms have the following definitions.

The language "hydrocarbon" includes substituted or unsubstituted alkyl, alkenyl, alkynyl, or aryl moieties.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 20 or fewer carbon atoms in its backbone (e.g., $C_1$-$C_{20}$ for straight chain, $C_3$-$C_{20}$ for branched chain), and in some embodiments, six or fewer. In certain other embodiments, the carbon chain can have 1-12 carbons, 1-10 carbons, 1-8 carbons, 1-6 carbons, or 1-4 carbon atoms in its backbone. Likewise, certain cycloalkyls have from 3-8 carbon atoms in their ring structure, and in some embodiments, 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), allyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_1$-$C_{20}$ for straight chain, $C_3$-$C_{20}$ for branched chain). Likewise, cycloalkenyl groups may have from 3-8 carbon atoms in their ring structure, and more preferably have 5 or 6 carbons in the ring structure. In other embodiments, the carbon chain can have 1-12 carbons, 1-10 carbons, 1-8 carbons, 1-6 carbons, or 1-4 carbon atoms in its backbone.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 20 or fewer carbon atoms in its backbone (e.g., $C_1$-$C_{20}$ for straight chain, $C_3$-$C_{20}$ for branched chain). In other embodiments, the carbon chain can have 1-12 carbons, 1-10 carbons, 1-8 carbons, 1-6 carbons, or 1-4 carbon atoms in its backbone.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Alkyl groups can be lower alkyls. Unless the number of carbons is otherwise specified, "lower alkyl" as used herein means an alkyl group, as defined above, but having from one to ten carbon atoms. "Lower alkenyl" and "lower alkynyl" can have chain lengths of, for example, 1-6, 2-6, 3-6, 1-4, 1-3, 2-4, 3-4, or 3 or 4 carbon atoms.

The term "acyl" includes compounds and moieties that contain the acyl radical ($CH_3CO-$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alknyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, and the like.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties that contain a carbon connected with a double bond to an oxygen atom. Examples of moieties that contain a carbonyl include aldehydes, ketones, carboxylic acids, amides, esters, anhydrides, etc.

The term "thiocarbonyl" or "thiocarboxy" includes compounds and moieties that contain a carbon connected with a double bond to a sulfur atom.

The term "ester" includes compounds and moieties that contain a carbon or a heteroatom bound to an oxygen atom that is bonded to the carbon of a carbonyl group.

The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "thioether" includes compounds and moieties that contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom that is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated," e.g., perfluorinated, generally refers to a moiety, e.g., perfluorocarbons, wherein all hydrogens are replaced by halogen atoms, e.g., fluorine.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Examples of heteroatoms are nitrogen, oxygen, sulfur and phosphorus.

The term "surfactant" refers to a surface-acting agent, or wetting agent, that lowers the surface tension of a liquid, or lowers the interfacial tension between two liquids. A surfactant can be an amphiphilic organic compound, for example, a soap-like detergent such as sodium dodecyl sulfate. Surfactants can be soluble in both organic solvents and water. A surfactant of the invention, or a surfactant as described herein, refers to a compound of any one of formulas I-IX.

The term "sample" or "biomaterial" refers to any biological material, tissue, or molecule that may be used in the methods of the invention. Examples include, without limitation, cell membranes and macromolecules, including proteins, and peptides. The sample can be a solution or extract containing a molecule or mixture of molecules that comprises at least one biomolecule originating from a biological source that can be subjected to analysis. A sample can include a crude or a purified, e.g., isolated or commercially obtained, sample. Further examples include, but are not limited to, inclusion bodies, biological fluids, biological tissues, biological matrices, embedded tissue samples, and cell culture supernatants.

The phrase "sample-surfactant complex" refers to a complex formed by a surfactant disclosed herein and a component of the sample.

The term "electrophoresis" refers to any of the various methods of analyzing molecules by their rate of movement in an electric field, i.e., based on the charge to mass ratio of the molecules. Examples include, but are not limited to, gel electrophoresis, polyacrylamide gel electrophoresis, including the tube, slab gel and capillary formats of polyacrylamide gel electrophoresis, free zone electrophoresis and capillary electrophoresis.

The terms "analysis" or "analyzing" refer to any of the various methods of solubilizing, separating, detecting, isolating, purifying, and/or characterizing molecules, such as, e.g., intact proteins, peptides, and fragments thereof. Examples include, but are not limited to, solid phase extraction; solid phase micro extraction; electrophoresis; mass spectrometry, e.g., Matrix Assisted Laser Desorption Ionization-Mass Spectrometry (MALDI-MS) or Electrospray Ionization (ESI); liquid chromatography, e.g., high performance, e.g., reverse phase, normal phase, or size exclusion chromatography; ion-pair liquid chromatography; liquid-liquid extraction, e.g., accelerated fluid extraction, supercritical fluid extraction, microwave-assisted extraction, membrane extraction, or Soxhlet extraction; precipitation; clarification; electrochemical detection; staining; elemental analysis; Edmund degradation; nuclear magnetic resonance; infrared analysis; flow injection analysis; capillary electrochromatography; ultraviolet detection; and combinations thereof.

The term "mass spectrometric detection" refers to any of the various methods of mass spectroscopy. Examples include, but are not limited to, electrospray ionization ("ESI") and Matrix Assisted Laser Desorption Ionization ("MALDI").

The terms "denature", "denaturing" or "denaturation" are used interchangeably and include the modification of the tertiary and/or secondary molecular structure of a biomolecule, such as a protein or DNA, by a surfactants compound described herein, heat, acid, alkali, or ultraviolet radiation, so as to destroy or diminish some of the original properties, for example, the original three-dimensional conformation, and a specific biological activity.

The term "digestion" and the phrase "chemical digestion" refers to a process of breaking down a molecule, for example, a biomolecule, e.g., a protein, into simpler chemical compounds (fragments). Chemical digestion is carried out using a digestion reagent, such as an enzyme, for example, a protease, or by a reaction with a chemical cleavage reagent, such as cyanogen bromide (CNBr), or hydroxylamine. Proteases include both specific, e.g., trypsin and chymotrypsin, and nonspecific, e.g. pepsin and papain, proteases. The chemical digestion can result in breaking of amide bonds. In certain instances, the chemical digestion can result in breaking designated or specific amide bonds.

Surfactant Compounds of the Invention

The invention provides a compound of formula I:

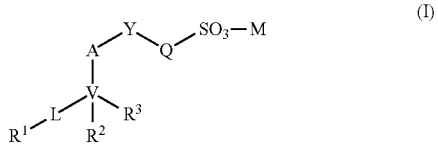

wherein:
Q is $(C_1\text{-}C_6)$alkyl, $(C_6\text{-}C_{10})$aryl, $(C_5\text{-}C_{10})$heteroaryl, or $(C_6\text{-}C_{10})$aryl-NH$(C_1\text{-}C_6)$alkyl;
Y is O, S, NH, —X—C(=O)—, —C=N—, carbonyl, or —O—C(=Z)—X—;
A is aryl, aryl$(C_1\text{-}C_6)$alkyl, heteroaryl, or a direct bond;
Z is O or S;
X is O, NH, or S;
V is C or N;
M is H, an alkali metal, or tetra$(C_1\text{-}C_{20})$alkylammonium;
L is —X—C(=Z)—X—, a direct bond, or absent when V is N;
$R^1$ is $(C_4\text{-}C_{20})$alkyl, $(C_2\text{-}C_{20})$alkenyl, $(C_6\text{-}C_{16})$aryl, $(C_5\text{-}C_{10})$heteroaryl, $(C_1\text{-}C_{20})$alkoxy$(C_1\text{-}C_{20})$alkyl, $(C_1\text{-}C_{12})$alkyl$(C_6\text{-}C_{20})$polyalkoxy, or $(C_6\text{-}C_{20})$(alkylthio)-$(C_1\text{-}C_6)$alkyl, or absent when V is N;
$R^2$ and $R^3$ are each independently H or $(C_1\text{-}C_{20})$alkyl; or $R^2$ and $R^3$ together form a 3-8 membered carbocycle ring, or a 3-8 membered heterocyclic ring comprising 1, 2, or 3 N($R^x$), S, or O; or
—V($R^2$)($R^3$)-L-$R^1$ is optionally —O—$R^1$ when A is aryl;
wherein any alkyl, alkenyl, aryl, or heteroaryl, carbocyclic ring, or heterocyclic ring, is optionally substituted with one or more (e.g., 1, 2, 3, 4, or 5) $(C_1\text{-}C_{20})$alkyl, $(C_2\text{-}C_{20})$alkenyl, $(C_2\text{-}C_{10})$alkynyl, $(C_3\text{-}C_{10})$cycloalkyl, $(C_1\text{-}C_{20})$alkoxy, $(C_1\text{-}C_{20})$alkylcarbonyl, $(C_1\text{-}C_{20})$alkylcarboxyl, halo, hydroxyl, —CO$_2R^x$, —SO$_2R^x$, —SO$_3R^x$, nitro, amino, N($R^x$)$_2$, mercapto, $(C_1\text{-}C_{20})$alkylthio, $(C_6\text{-}C_{16})$aryl, $(C_6\text{-}C_{30})$arylthio, trifluoromethyl, =O, heteroaryl, or heterocycle groups; provided that Q is not substituted with CO$_2$H; and each $R^x$ is independently H, $(C_1\text{-}C_6)$alkyl, $(C_6\text{-}C_{16})$aryl, or $(C_1\text{-}C_6)$alkyl-$(C_6\text{-}C_{16})$aryl;
or an anion or a salt thereof.

Specific values of Q include methyl, ethyl, propyl, butyl, pentyl, hexyl, and branched variations thereof. The group Q can be substituted. For example, in one embodiment, Q can be a hydroxy substituted alkyl, such as 2-propyl. In certain specific embodiments, Q can be $(C_2\text{-}C_3)$alkyl. In other embodiments, Q can be $(C_6\text{-}C_{10})$aryl, for example, phenyl or naphthyl; or $(C_5\text{-}C_{10})$heteroaryl, for example, furyl or pyridyl. In yet other embodiments, Q can be $(C_6\text{-}C_{10})$aryl-NH$(C_1\text{-}C_6)$alkyl, for example, phenyl-amino-ethyl or phenyl-amino-propyl. In certain embodiments, the hydrogen of the $(C_6\text{-}C_{10})$aryl-NH$(C_1\text{-}C_6)$alkyl can be replaced with a $(C_1\text{-}C_6)$alkyl-SO$_3$-M group, such as in formula IX.

Specific values of Y include O, S, NH, —O—C(=O)—, —NH—C(=O)—, —S—C(=O)—, —C=N—, carbonyl, —O—C(=O)—O—, —O—C(=O)—NH—, —O—C(=O)—S—, —O—C(=S)—O—, —O—C(=S)—NH—, and —O—C(=S)—S—.

Specific values of A include aryl, such as phenyl or naphthyl, heteroaryl, such as furyl or pyridyl. The group A can also be a direct bond linking Y to V.

A specific value for V is C. Another specific value for V is N. The group A can be unsubstituted, or substituted, for example, with a halo or nitro group.

A specific value for M is H. The group M can also be an alkali metal, such as lithium, sodium, or potassium. Other values for M include tetraalkyl ammonium groups, such as tetraethyl ammonium or tetrabutyl ammonium. The group M can also be other ammonium groups wherein the nitrogen substituents are alkyl, aryl, or a combination thereof, such as trimethylphenyl ammonium. Other cations known to those of skill in the art may also be used as suitable counterions for the sulfate group associated with the group M. As would be recognized by one skilled in the art, sodium salts of the compounds can be conveniently isolated, and these sodium salts work well in many embodiments of the invention.

Specific values for L include —X—C(=O)—X—, and —X—C(=S)—X—, wherein X is O, NH, or S; for example, carbonate, thiocarbonate, carbamate, thiocarbamate, and derivatives thereof.

Specific values of $R^1$ include alkyl chains of 4-20 carbon atoms in length, either substituted or unsubstituted. Certain specific values include pentyl, hexyl, heptyl, decyl, undecyl, dodecyl, tetradecyl, and the like. $R^1$ can also be other groups including $(C_2\text{-}C_{20})$alkenyl, for example, 1-octenyl, or 1-dodecenyl; $(C_6\text{-}C_{16})$aryl, for example, phenyl; $(C_5\text{-}C_{10})$heteroaryl, for example, furyl, or pyridyl; $(C_1\text{-}C_{20})$alkoxy$(C_1\text{-}C_{20})$alkyl, for example, nonoxylmethyl; $(C_1\text{-}C_{12})$alkyl$(C_6\text{-}C_{20})$polyalkoxy, or $(C_6\text{-}C_{20})$(alkylthio)-$(C_1\text{-}C_6)$alkyl, for example, nonylthiomethyl; or absent, for example, when V is N.

Values for $R^2$ include H and $(C_1\text{-}C_{20})$alkyl, for example, $(C_1\text{-}C_{16})$alkyl, $(C_1\text{-}C_{12})$alkyl, $(C_1\text{-}C_{10})$alkyl, $(C_1\text{-}C_8)$alkyl, $(C_2\text{-}C_8)$alkyl, or $(C_1\text{-}C_6)$alkyl. One specific value is H. Another specific value is methyl.

Values for $R^3$ include H and $(C_1\text{-}C_{20})$alkyl, for example, $(C_1\text{-}C_{16})$alkyl, $(C_1\text{-}C_{12})$alkyl, $(C_1\text{-}C_{10})$alkyl, $(C_1\text{-}C_8)$alkyl, $(C_2\text{-}C_8)$alkyl, or $(C_1\text{-}C_6)$alkyl. One specific value is H. Another specific value is methyl.

The groups $R^2$ and $R^3$ can also be combined together to form a 3-8 membered ring. The ring can be a carbocycle ring, or a heterocyclic ring. The heterocyclic ring can include one or more, e.g., 1, 2, or 3 heteroatoms, including N, S, O, or a combination thereof. A nitrogen of the heterocyclic ring can be substituted with an H, or an substituent, for example, a $(C_1\text{-}C_6)$alkyl, a $(C_6\text{-}C_{16})$aryl, or a $(C_1\text{-}C_6)$alkyl$(C_6\text{-}C_{16})$aryl group. Examples of heterocyclic rings include, but are not limited to, pyrrole, furan, thiophene, thiazole, isothiaozole, imidazole, triazole, tetrazole, pyrazole, oxazole, isooxazole, pyridine, pyrazine, pyridazine, and pyrimidine.

In certain embodiments, the group —V($R^2$)($R^3$)-L-$R^1$ can be —O—$R^1$ when A is an aryl group. For example, in certain embodiments, —V($R^2$)($R^3$)-L-$R^1$ can be —O—$R^1$ wherein $R^1$ is $(C_4\text{-}C_{20})$alkyl or $(C_1\text{-}C_{20})$alkoxy$(C_1\text{-}C_{20})$alkyl. In one embodiment, Q can be $(C_1\text{-}C_6)$alkyl, Y can be —C=N—, A can be phenyl, and —O—$R^1$ can be pentoxy, hexyloxy, decyloxy, or tetradecyloxy.

In various embodiments, the alkyl, alkenyl, aryl, or heteroaryl, carbocyclic ring, or heterocyclic ring, can be unsubstituted, or optionally substituted with one or more (e.g., 1, 2, 3, 4, or 5) substituents as defined herein. Various substituents include $(C_1\text{-}C_{20})$alkyl, $(C_2\text{-}C_{20})$alkenyl, $(C_2\text{-}C_{10})$alkynyl, $(C_3\text{-}C_{10})$cycloalkyl, $(C_1\text{-}C_{20})$alkoxy, $(C_1\text{-}C_{20})$alkylcarbonyl, $(C_1\text{-}C_{20})$alkylcarboxyl, halo, hydroxyl, —CO$_2R^x$, —SO$_2$R$^x$, —SO$_3$R$^x$, nitro, amino, N(R$^x$)$_2$, mercapto, (C$_1$-C$_{20}$)alkylthio, (C$_6$-C$_{16}$)aryl, (C$_6$-C$_{30}$)arylthio, trifluoromethyl, =O, heteroaryl, or heterocycle groups.

Each variable R$^x$ can independently be H, (C$_1$-C$_6$)alkyl, (C$_6$-C$_{16}$)aryl, or (C$_1$-C$_6$)alkyl-(C$_6$-C$_{16}$)aryl. For example, in one embodiment, R$^x$ can be H. In another embodiment, R$^x$ can be methyl, ethyl, propyl, butyl, pentyl, or hexyl, wherein each is optionally branched, optionally unsaturated, and/or optionally substituted with one of the groups described above. In another embodiment, R$^x$ can be phenyl, optionally substituted with one of the groups described above. In yet another embodiment, R$^x$ can be benzyl, phenylethyl, phenylpropyl, or the like, optionally substituted with one of the groups described above.

In certain embodiments, Q is not substituted with one of the aforementioned substituents. For example, in one embodiment, Q is not substituted with CO$_2$H.

In certain embodiments, a salt of an acid can be prepared. Suitable salts include, but are not limited to, mineral or organic acid salts of basic residues such as amines; alkali or organic salts of acidic residues such as carboxylic acids; and the like. The salts include conventional salts and quaternary ammonium salts of the parent compound formed, for example, from inorganic or organic acids. Salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can also form salts with various amino acids.

The compounds of the invention can also be certain compounds of formulas II-IX. For example, certain compounds formula I can also be certain compounds of formulas II-VIII. For certain specific compounds of the invention, i.e., compounds of formulas I-IX, see the compounds illustrated in the Examples section below.

In one embodiment, the compound of formula I is a compound of formula II:

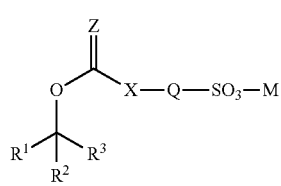

(II)

wherein the variables are as described above for formula I. In one embodiment, R$^1$ is heptyl or undecyl, R$^2$ and R$^3$ are both methyl, Z is O, X is NH, Q is (C$_1$-C$_6$)alkyl, for example, propyl, and M is H. In some embodiments, R$^1$ is substituted with any aryl or heteroaryl group. The aryl or heteroaryl group can be substituted. In certain embodiments, the aryl or heteroaryl substituent is located alpha (one carbon away) from the carbon to which R$^2$ and R$^3$ are attached. In one specific embodiment, R$^2$ and R$^3$ are both H and R$^1$ is methyl, substituted with phenyl, wherein the phenyl is substituted with hexyloxy.

In another embodiment, the compound of formula I is a compound of formula III:

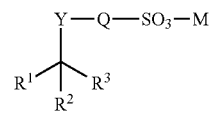

(III)

wherein the variables are as described above for formula I.

In another embodiment, the compound of formula I is a compound of formula IV:

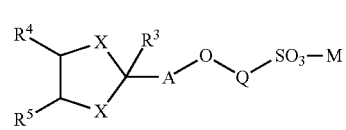

(IV)

wherein the variables are as described above for formula I, and R$^4$ and R$^5$ are each independently H or (C$_1$-C$_{20}$)alkyl.

In another embodiment, the compound of formula I is a compound of formula V:

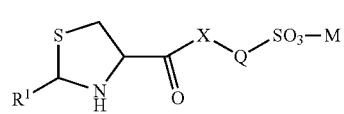

(V)

wherein the variables are as described above for formula I.

In another embodiment, the compound of formula I is a compound of formula VI:

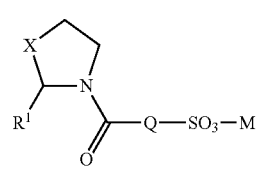

(VI)

wherein the variables are as described above for formula I.

In another embodiment, the compound of formula I is a compound of formula VII:

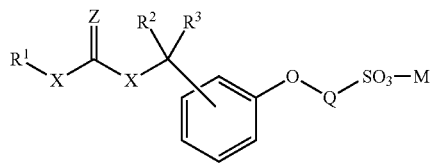

(VII)

wherein the variables are as described above for formula I, and the carbon attached to R$^2$ and R$^3$ can be in an ortho, meta, or para orientation with respect to the oxy substituent of the benzene ring shown in formula VII.

In another embodiment, the compound of formula I is a compound of formula VIII:

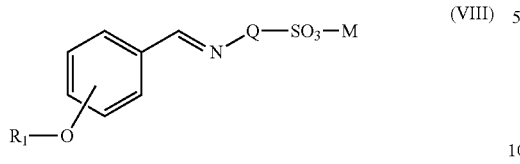

(VIII)

wherein the variables are as described above for formula I, and the R¹—O— substituent of the benzene ring in formula VIII can be in an ortho, meta, or para orientation with respect to the imine substituent of the benzene ring.

In another embodiment, the surfactant compound is a compound of formula IX:

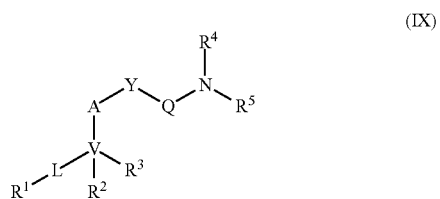

(IX)

wherein:

Q is $(C_1$-$C_6)$alkyl, $(C_6$-$C_{10})$aryl, or $(C_5$-$C_{10})$heteroaryl;

Y is O, S, NH, —X—C(═O)—, —C═N—, carbonyl, —O—C(═Z)—X—, or —O—$(CH_2)_{1-6}$—;

A is aryl, aryl$(C_1$-$C_6)$alkyl, heteroaryl, or a direct bond;

Z is O or S;

X is O, NH, or S;

V is C or N;

each M is independently H, an alkali metal, or tetra$(C_1$-$C_{20})$alkylammonium;

L is —X—C(═Z)—X— or a direct bond;

R¹ is $(C_4$-$C_{20})$alkyl, $(C_2$-$C_{20})$alkenyl, $(C_6$-$C_{16})$aryl, $(C_5$-$C_{10})$heteroaryl, $(C_1$-$C_{20})$alkoxy$(C_1$-$C_{20})$alkyl, $(C_1$-$C_{12})$alkyl$(C_6$-$C_{20})$polyalkoxy, or $(C_6$-$C_{20})$(alkylthio)-$(C_1$-$C_6)$alkyl, or absent when V is N, or optionally H when R² and R³ together form a ring;

R² and R³ are each independently H or $(C_1$-$C_{20})$alkyl; or

R² and R³ together form a 3-8 membered carbocycle ring, or a 3-8 membered heterocyclic ring comprising 1, 2, or 3 N(R$^x$), S, or O; or —V(R²)(R³)-L-R¹ is optionally —O—R¹ when A is aryl, or —C(aryl)₂(aryl)-OR¹;

R⁴ is —$(C_1$-$C_{12})$alkyl-$SO_3$-M;

R⁵ is H or —$(C_1$-$C_{12})$alkyl-$SO_3$-M;

wherein any alkyl, alkenyl, aryl, or heteroaryl, carbocyclic ring, or heterocyclic ring, is optionally substituted with one or more (e.g., 1, 2, 3, 4, or 5) $(C_1$-$C_{20})$alkyl, $(C_2$-$C_{20})$alkenyl, $(C_2$-$C_{10})$alkynyl, $(C_3$-$C_{10})$cycloalkyl, $(C_1$-$C_{20})$alkoxy, $(C_1$-$C_{20})$alkylcarbonyl, $(C_1$-$C_{20})$alkylcarboxyl, halo, hydroxyl, —$CO_2R^x$, —$SO_2R^x$, —$SO_3R^x$, nitro, amino, N(R$^x$)₂, mercapto, $(C_1$-$C_{20})$alkylthio, $(C_6$-$C_{16})$aryl, $(C_6$-$C_{30})$arylthio, trifluoromethyl, ═O, heteroaryl, or heterocycle groups; provided that Q is not substituted with $CO_2H$; and each R$^x$ is independently H, $(C_1$-$C_6)$alkyl, $(C_6$-$C_{16})$aryl, or $(C_1$-$C_6)$alkyl-$(C_6$-$C_{16})$aryl;

or a salt thereof.

In one specific embodiment, an acid-labile surfactant of formula I includes the compound 3116:

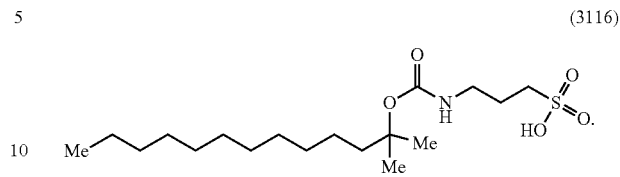

(3116)

Figure 2:
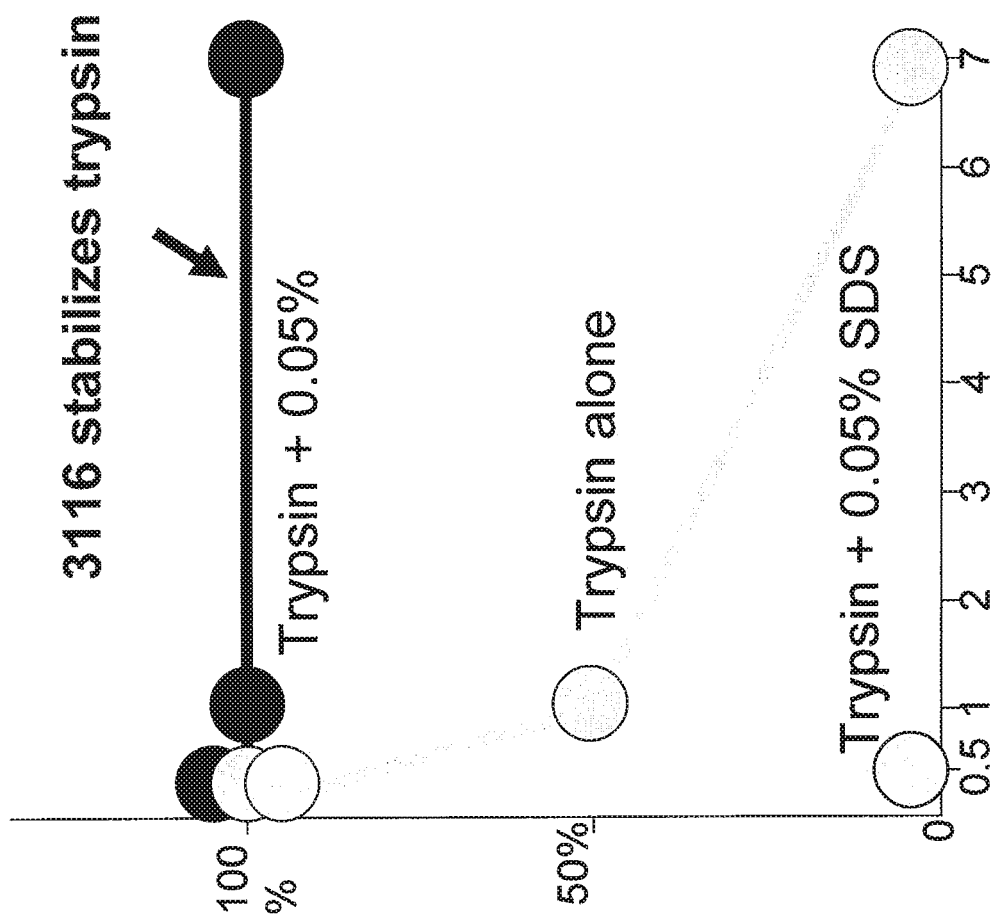
FIG. 2 illustrates the effect of compound 3116 on trypsin activity according to one embodiment, showing that compound 3116 stabilized trypsin activity while SDS inhibited trypsin activity within 30 minutes; trypsin activity was measured as a rate of N-α-benzoyl-L-arginine ethyl ester hydrochloride (BAEE) cleavage.

Compound 3116 can be used as an acid-labile surfactant to facilitate the solubilization and denaturation of a protein or peptide. Compound 3116 stabilizes proteases and enhances the proteolysis activity of trypsin. See FIG. 2, which illustrates the effect of compound 3116 on trypsin activity. Under standard digestion conditions, compound 3116 stabilized trypsin activity while SDS inhibited trypsin activity within 30 minutes. Additionally, after degradation, compound 3116 does not interfere with chromatographic separations and mass spectrometric analyses.

For example, digestion of myoglobin using standard protocol requires overnight digestion. In one experiment, myoglobin was largely digested within one hour in the presence of compound 3116. Horse myoglobin was digested with trypsin at a 50:1 ratio for one hour at 37° C., alone and separately in the presence of 0.01% compound 3116. FIG. 3A and FIG. 3B shows HPLC chromatograms of the myoglobin digests: FIG. 3A, standard protocol with no 3116, and FIG. 3B, digest in the presence of 3116. The peaks in FIG. 3A and FIG. 3B indicate peptides or partial digestion fragments. As can be observed from the chromatograms, the standard protocol resulted in insufficient digestion while the digestion in the presence of compound 3116 produced numerous (>15) identifiable peaks.

In another specific embodiment, an acid-labile and thermolabile surfactant of formula I includes compounds 3211 and 3212:

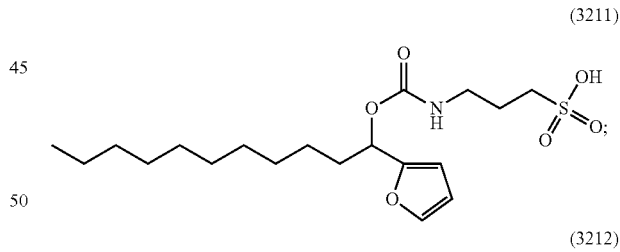

(3211)

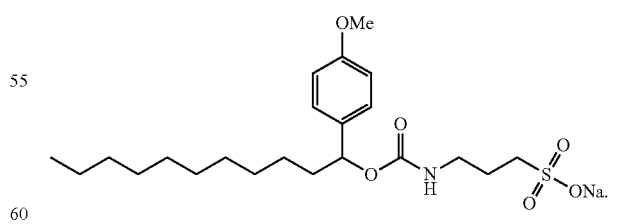

(3212)

Compounds 3211 and 3212 can be used as thermolabile and/or acid-labile surfactants to facilitate the solubilization and denaturation of a peptide. For any of the compounds described herein, the sulfonic acid form of the compound may be employed, or alternatively, a sulfonic acid salt may be employed, depending on the desired properties and the conditions employed. For example, in certain buffer solutions the compounds disclosed herein will convert to, or be in an equilibrium with, an alkali metal salt, such as a sodium salt.

In another specific embodiment, an acid-labile surfactant of formula I includes the compound 3266:

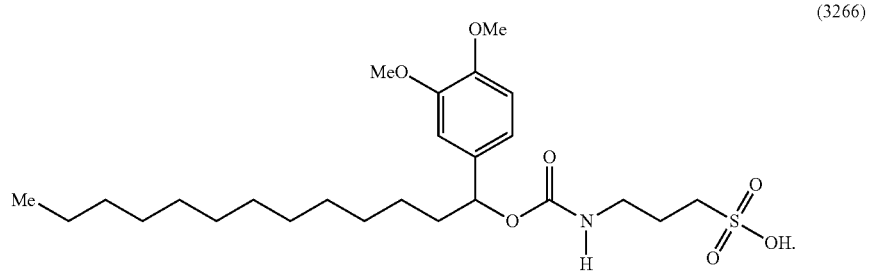 [SMILES: CCCCCCCCCCCCC(OC(=O)NCCCS(=O)(=O)O)c1ccc(OC)c(OC)c1]

(3266)

Compound 3266 is an acid-labile surfactant that can be used as an aid for deglycosylation of a biomaterial in conjunction with a glycosidase.

The surfactants described herein offer substantial improvement in protein sample preparation for mass spectrometric analysis. These surfactants therefore provide significant advantages for those involved in the use of digestion enzymes for the analysis and identification of peptide samples, including the ability to degrade the surfactant such that the degraded surfactant components do not interfere in the analytical procedure.

Methods of Using the Surfactants

Cellular protein extracts are typically too complex for immediate mass spectrometric analysis. Two major approaches to reducing protein complexity include fractionation in gel, and fractionation with liquid chromatography. The surfactant compounds disclosed herein can aid in both methods of reducing protein complexity, both prior to and after sample digestion. The surfactant compounds aid the solubilization and digestion of proteins, and can be used as a replacement for other agents that interfere with fractionation and chromatography, and other analytical techniques.

The invention provides methods of protein sample preparation and analysis. The method can include sample fractionation followed by gel electrophoresis, for example, using 1D or 2D SDS-PAGE. The separated proteins can be excised and then individually digested, for example, by chemical digestion agents or a protease, such as trypsin, in conjunction with a surfactant compound as described herein, to provide a mixture of peptide samples. These samples can then be analyzed and characterized by various techniques, for example, HPLC or mass spectrometry, such as MALDI-TOF mass spectrometry. The surfactants described herein bring an important advantage to existing in-gel digestion protocols. Acting as protein digestion aid and, simultaneously, as a peptide extracting agent, the surfactants allow for the combination of in-gel protein digestion and peptide extraction into a single and short step.

The methods of the invention also include protein digestion aided by a surfactant of the invention, followed by chromatographic separation. The separated peaks can then be analyzed by mass spectrometry, for example ESI. The LC/MS techniques can be conducted in a high through-put format. The mass to charge (m/z) ratios of the peptides can be recorded and selected for MS/MS analysis. The peptides can then be dissociated into fragments representative of the original peptide sequence.

In one aspect, the invention provides methods for analyzing a sample by contacting a sample with a surfactant compound of any one of formulas I-IX as defined above, and analyzing the sample. In certain embodiments, the sample may be heated either before or after contacting the sample with a surfactant of the invention.

In various embodiments, analyzing a sample includes electrophoresis. In certain embodiments, the electrophoresis is gel electrophoresis, free zone electrophoresis, or capillary electrophoresis. The electrophoresis can be polyacrylamide gel electrophoresis, including tube, slab gel, and capillary formats of polyacrylamide gel electrophoresis.

In other embodiments, the step of analyzing the sample includes mass spectrometric analysis, high performance liquid chromatography, ion-pair liquid chromatography, liquid-liquid extraction, ultraviolet detection, or a combination thereof.

In various embodiments, hydrolysable surfactants can be used to complex with protein mixtures for polyacrylamide gel electrophoresis. After the electrophoretic separation, the proteins can be freed from surfactants, optionally by treating the gel with acid solution, or by heating the gel. The protein mixtures may be further purified by conventional separation methods such as liquid-liquid extraction, solid-phase extraction or liquid chromatography.

The invention also provides a kit for performing analysis of a sample, where the kit includes a surfactant compound as described herein, instructions for use, and optionally a solution for degrading the surfactant, a gel, a molecular weight standard, and/or a staining reagent.

The invention provides a simplified, yet more efficient method of extracting gel-trapped peptides. The surfactants of the invention greatly improve the overall yield of peptides in an in-gel digestion protocol. They also offer a important advantage over standard peptide extraction protocols, wherein the surfactants allow for extraction of long and/or very hydrophobic peptides that regularly remain in a gel after standard peptide extraction (i.e., with TFA and/or acetonitrile). The method can also increase peptide yield by other mechanisms, such as by preventing peptide loss due to absorption of peptides by labware (i.e., plastic tips and reaction tubes, glass pipettes, and the like) or by precipitation of the peptides. Both in-gel and in-solution digestion protocols benefit from these advantageous properties of the methods described herein.

In certain embodiments, a chemical reaction using surfactants of the invention is chemical digestion. In one embodiment, the chemical digestion occurs by contacting a molecule, e.g., a biomolecule, with a protease. Exemplary proteases include, but are not limited to specific proteases such as Trypsin, Chymotrypsin Lys-C, Glu-C (V8 protease), AspN, Arg-C, S. Aureus, and Clostripain, and non-specific proteases, such as, Pepsin, and Papain. In certain embodiments the protease is immobilized, e.g., immobilized enzymatic reactor. Alternatively, digestion may be accomplished by reaction with CNBr or reaction with hydroxylamine. Additionally, in certain embodiments, the digestion can occur in an electrophoretic gel in the presence or absence of one or more surfactants that are different from the surfactants of the invention, e.g., SDS.

Solubilization of insoluble samples by surfactants of the present invention allows digestion of samples that are typically insoluble and therefore difficult to digest by known methodology. In addition, the surfactants enable the use of lower amounts of trypsin to digest a protein. For example, the ratio of trypsin to total protein is typically 1:50 to 1:20. However, in some embodiments, in the presence of the surfactants described herein, the ratio of trypsin to total protein can be 1:100 or lower. Furthermore, use of the surfactants described herein can increase the digestion rate of trypsin and result in fewer incomplete cleavages than observed for known methodologies, such as the addition of organic solvents or use of excessive heat.

Additionally, it is known that if digestion, in which urea has been utilized as a solubilizing agent, is allowed to proceed for too long, the urea will act upon and modify the protein, making analysis of peptide fragments more difficult. In this regard, the surfactants of the invention will not modify the protein, regardless of the length of time allowed for digestion.

The invention offers an advantageous improvement to standard in-solution digestion protocol involving urea as a solubilizing agent. A user has the option to mix urea and a surfactant as described herein, and digest proteins in such a mixture. The surfactants retain their useful properties (solubilization, denaturing activity, and peptide preservation) in the presence of urea. Protein digestion in a urea/surfactant mixture can lead to a higher number of identified proteins, higher number of generated peptides per protein, and higher peptide recovery, than in the presence of urea or surfactant alone. One particularly attractive feature of the methods described herein is that there is no need to alter the digestion protocol. The surfactants are fully compatible with standard in-solution digestion protocols.

In certain embodiments, use of the surfactants described herein can enhance a chemical reaction or enhance a chemical property of another agent. Such chemical reactions and properties include a more complete reaction or digestion, increased digestion efficiency, increased digestion yield, increased digestion rate, and increased utility, such as reduced interference in spectrometric or chromatographic analysis techniques.

After a chemical reaction, a sample can be separated from the surfactants by various methods, including degradation with acidic solution. The sample may be further purified by conventional separation methods such as liquid-liquid extraction, solid-phase extraction or liquid chromatography. This ability to separate a sample from surfactants easily after a chemical reaction may be used in various applications, with significant benefits to separation science.

An additional embodiment provides a method for enhancing chemical digestion of a biomolecule comprising contacting the molecule with a digestive enzyme, e.g., a protease, and a surfactant of the present invention, to thereby enhance the chemical digestion of the molecule. In an additional embodiment, the invention provides a kit for enhancing chemical digestion of a biomolecule comprising a surfactant of the present invention, and instructions for use. In certain embodiments, the biomolecule is a protein.

In some embodiments, the kit for enhancing chemical digestion of a biomolecule further includes a digestive enzyme, e.g., a protease and/or a glycosidase. Suitable proteases include, without limitation, Trypsin, Chymotrypsin Lys-C, Glu-C (V8 protease), AspN, Arg-C, S. Aureus, Clostripain, Pepsin, and Papain. A suitable glycosidase can be PNGase F.

In various embodiments, the products of surfactant degradation are compatible with mass spectrometric detection, high performance liquid chromatography analysis, and with protease activity. In certain embodiments, a protein fragment is generated by chemical digestion or a combination of chemical alteration and chemical digestion. In certain specific embodiments, a protein fragment or a peptide is the product of a protein that has been digested by contact with a protease and a surfactant as described herein.

In an additional embodiment, compounds of the invention may be used in one dimensional and two dimensional polyacrylamide gel electrophoresis. Two dimensional polyacrylamide gel electrophoresis (2D-PAGE) is a technique commonly used for the analysis of mixtures of proteins. (U. K Laemmli, Nature 227, 680-685, 1970). Proteins are separated first by an electrophoretic such as isoelectric focusing followed by a second dimension separation based on protein size.

Sodium dodecyl sulfate (SDS), the detergent most often used with 2D-PAGE, forms stable non-covalent complexes with proteins. The SDS complexed proteins have identical charge density, therefore, they separate in an electrical field according to their size. This technique is capable of separating a complex protein mixture into several hundred individual components that can be excised from the gel and further identified by other techniques. One such technique is mass spectrometry.

The direct analysis of proteins removed from electrophoresis gels is often difficult. Commonly, the samples contain detergent concentrations that hinder analysis by mass spectrometry. In MALDI analysis for example, this problem is the result of the tendency of the detergent to aggregate or associate with the protein or peptide preventing proper incorporation into the matrix crystal. Special steps must be taken to remove the interference prior to analysis by MALDI-MS. Examples of such measures include, but are not limited to electroblotting of PAGE gels and detergent exchange of SDS with a more MALDI tolerant detergent like n-octyl-glucoside, for example. An alternative approach is to use acid-labile surfactants disclosed herein in place of commonly used detergents in SDS-PAGE, for example, the surfactants disclosed in the Examples below.

Furthermore, the ability to estimate the size and amount of a protein has led to various applications of SDS-PAGE. However, there are some drawbacks to the technology. For example, it is very difficult to use mass spectrometry to monitor and analyze samples from SDS-PAGE separations because SDS interferes with the sensitivity of mass spectrometry detection. Furthermore, it is very difficult to separate SDS from SDS/protein complex since SDS is a surfactant that forms emulsions. The compounds of the instant invention provide a solution to the problems associated with using SDS prior to mass spectrometry analysis.

The surfactants of the invention may be used in applications which benefit from the initial presence and ultimate removal of a surfactant. In particular, the surfactants described herein are useful for the solubilization, degradation, digestion, separation, purification, analysis, and/or characterization of peptides and proteins.

The surfactants of the invention are particularly advantageous for in-gel protein digestion. The in-gel digestion method based on use of the surfactants is fully compatible with SDS-based gel electrophoresis. After resolving proteins in SDS-PAGE, a gel slice with a protein of interest is cut out of the gel and SDS is removed by standard washing techniques. The gel slice is soaked in a solution containing the surfactant, or the surfactant and trypsin, or other protease. The surfactants can then act in three ways. First, they can solubilize proteins precipitated within a gel during the fixation step. Second, they can unfold the proteins, allowing for easy access to protein cleavage sites for proteases. Third, they can allow for efficient extraction of generated peptides from the gel.

One particular advantage is that the surfactants allow for extraction of long and/or very hydrophobic peptides that typically remain in a gel that is treated with a standard peptide extraction protocol (i.e., with TFA and acetonitrile). Additionally, use of the surfactants ensures full peptide recovery after extraction by preventing peptide absorption by labware (i.e., pipette tips and reaction tubes), or by preventing peptide precipitation due to poor solubility.

The surfactants of the invention can provide an important advantage to existing in-gel digestion protocol. Acting as protein digestion aids and, simultaneously, as peptide extracting agents, the surfactants allow one to combine in-gel protein digestion and peptide extraction into a single efficient step. The step can be completed in one hour.

These advantages make the surfactants ideal universal agents for aiding in-gel sample preparation. Their use results in a reduction in the time and labor required for the sample preparation, as well as an increase in sequence coverage and probability scores. In several embodiments, no separate degradation step is required for the surfactants because they self-degrade during a digestion reaction or during downstream sample preparation steps (i.e., during decreasing of pH by TFA before clean-up on C18 clean-up tips). The degraded surfactants do not interfere with liquid chromatography and mass spectrometric analysis, further establishing the surfactants' compatibility with comprehensive protein analytical techniques.

The surfactants are also suitable with in-solution digestion protocols. First, the surfactants efficiently solubilize proteins. Solubilization is required for efficient protein digestion. Second, the surfactants unfold proteins, allowing for easy access to protein cleavage sites for the proteases. Third, they stabilize the protease, leading to an additional increase in protein digestion efficiency over standard techniques. Additionally, and potentially of most significance, the surfactants ensure robust recovery of peptides generated in the digestion step. The surfactants achieve this result by preventing peptide absorption by labware. Peptide loss is a commonly observed effect found in in-solution digestion protocol s and potentially leads to a decrease in the number of identified proteins, individual protein sequence coverage, and data from mass spectrometric analysis.

Additional advantages of the surfactants described herein include that precipitation of peptides can be avoided by adjusting the surfactant concentration, thereby reducing or eliminating losses of peptides during recovery steps. Currently used acid-labile surfactants such as RapiGest™ have several disadvantages, such as the formation of cloudy solutions or suspensions, which result in peptide loss through precipitation. Also, some currently used acid-labile surfactants require boiling for complete protein solubilization, especially for membrane proteins. The surfactants described herein can solubilize even the problematic membrane proteins. Additionally, currently used surfactants provide less enhancement of enzyme activity under mild conditions (i.e., at room temperature). Other currently used acid-labile surfactants demonstrate low-efficient enhancement of protein digestion. For example, under conditions where surfactant 3211 afforded complete digestion of myoglobin in one hour, PPS Silent™ Surfactant (obtainable from Protein Discovery, Knoxville, Tenn.) provided only 5% digestion. Finally, currently used commercial reagents require an additional degradation step after protease digestion, while the surfactants described herein can degrade under the digest conditions by the end of the digestion, greatly simplifying sample preparation.

General Preparatory Methods

Several methods exist for the preparation of urethanes (or carbamates). The method used to prepare the compounds described herein involves the conversion of an alcohol to a reactive p-nitrophenyl carbonate, followed by the addition of an amine, to provide the urethane. One skilled in the art will readily recognize that there are other ways in which the compounds may be prepared. For example, an alcohol could be treated with 1,1'-carbonyldiimidazole to provide an imidazolide, followed by addition of an amine. The amine can be, for example, a sulfonic acid sodium salt linked to the amine through an organic group. An alcohol can also be treated with phosgene or a phosgene equivalent (e.g., diphosgene or triphosgene) to provide a chloroformate, followed by addition of an amine. Alternatively, an alcohol can be combined with a carbamoyl chloride to afford the urethane. It should be understood that many variations and modifications may be made while remaining within the scope of the invention.

One method for the preparation of compounds of the invention can be represented by the procedure of Scheme 1.

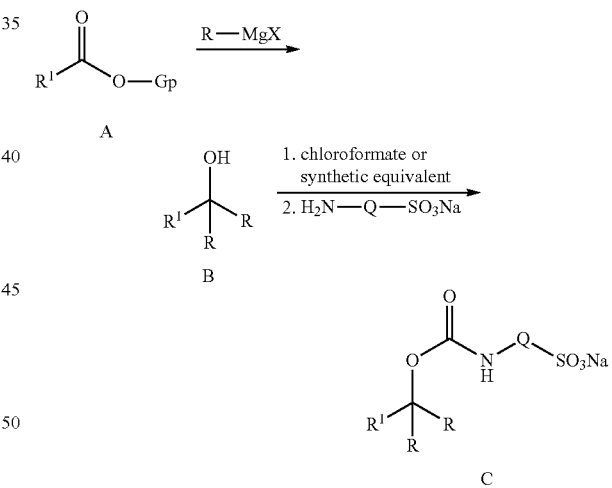

wherein Gp of compound A can be any group that can be the oxy-substituent of an ester, such as an alkyl, aryl, heteroaryl, or the like; R is any organic group that forms a suitable Grignard reagent, for example an $R^2$ group as defined for formula I; and $R^1$ and Q are as defined for formula I. Many aspects of Scheme 1 can be varied to prepare the compounds of formulas I-IX, depending on the desired product, the reactivity of the intermediates, and the necessity or convenience of protecting groups. Many other approaches to the preparation of carbamates can be taken, as discussed above.

The methods of synthesis of the invention can produce isomers in certain instances. Although the methods of using surfactants of the invention do not always require separation of these isomers, such separation may be accomplished, if desired, by methods known in the art. For example, preparative high performance liquid chromatography methods may be used for isomer purification, for example, by using a column with a chiral packing.

Additional background information may be found in the following publications: Kyte et al., J. Mol. Biol. (1982) 157(1):105-32; March's Advanced Organic Chemistry Reactions, Mechanisms, and Structure, 5.sup.th Ed. by Michael B. Smith and Jerry March, John Wiley & Sons, Publishers; Wuts et al. (1999) Protective Groups in Organic Synthesis, 3.sup.rd Ed., John Wiley & Sons, Publishers; Behforouz, M.; Kerwood, J. E. Alkyl and Aryl Sulfenimides. J. Org. Chem., 34 (1), 51-55 (1969); and Harpp, D. N.; Ash, D. K.; Back, T. G.; Gleason, J. G.; Orwig, B. A.; VanHorn, W. F. A New Synthesis of Unsymmetrical Disulifdes. Tetrahedron Letters, 41, 3551-3554 (1970).

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Example 1. Preparation of Compound 3116

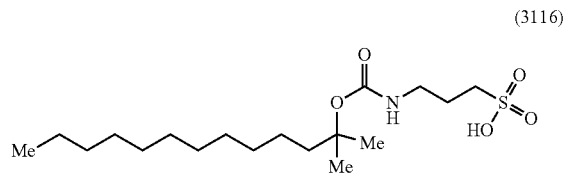 [SMILES: CCCCCCCCCCCC(C)(C)OC(=O)NCCCS(=O)(=O)O]
(3116)

Methyl laurate (2.0 g, 9.33 mmol) was dissolved in 20 mL of anhydrous THF and the solution was cooled in an ice-water bath. A solution of 3M methylmagnesium chloride in THF (6.5 mL, 19.6 mmol) was added dropwise via syringe and the stirred reaction mixture was allowed to warm to ambient temperature and react for 4 hours. The reaction mixture was poured into 50 mL of 2M aqueous sulfuric acid solution and was extracted with ethyl acetate. The organic extracts were dried over anhydrous sodium sulfate and concentrated to give 2.0 g (99% yield) of 2-methyl-2-tridecanol as a colorless oil.

MS (ESI+): m/z 215.4 (MH+).

The 2-methyl-2-tridecanol (0.36 g, 1.68 mmol) was dissolved in 1 mL of pyridine and 2 mL of THF. The solution was cooled in an ice-water bath and p-nitrophenyl chloroformate (340 mg, 1.68 mmol) was added and the reaction was allowed to warm to ambient temperature and react overnight. The reaction mixture was roto-evaporated and the residue was partitioned between dichloromethane and water. The aqueous phase was extracted twice with dichloromethane and the combined organic extracts were then dried over anhydrous sodium sulfate and roto-evaporated to provide a thick oil. The crude product was chromatographed on silica gel using dichloromethane to afford 0.13 g (20% yield) of 2-methyl-2-tridecanol p-nitrophenyl carbonate.

To a solution of 2-methyl-2-tridecanol p-nitrophenyl carbonate (0.11 g, 0.29 mmol) in 5 mL of THF was added a solution of 3-aminopropane sulfonic acid, sodium salt (0.15 g, 0.93 mmol) in 2 mL of water. The reaction mixture was heated at 50° C. for 12 hours. The reaction mixture was concentrated to a crude solid residue which was purified by chromatography on silica gel using a 4:1 mixture of dichloromethane-methanol to afford 70 mg (60% yield) of compound 3116 as an off-white solid.

MS (ESI−): m/z 378.6 (M-H)−.

A synthetic route to compound 3116 is shown in Scheme 2.

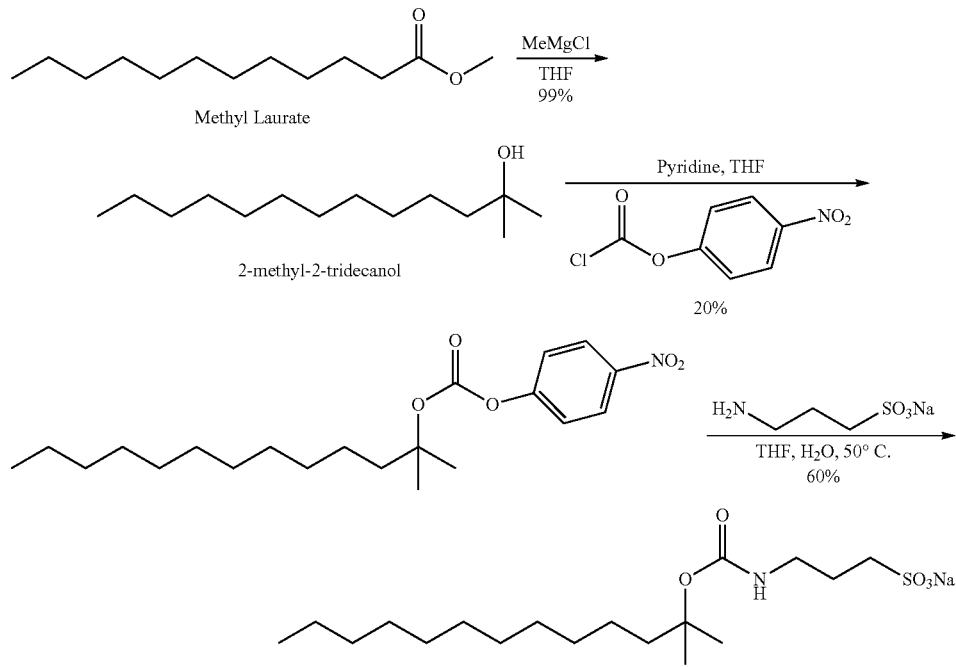

Example 2. Preparation of Compounds 3211 and 3212

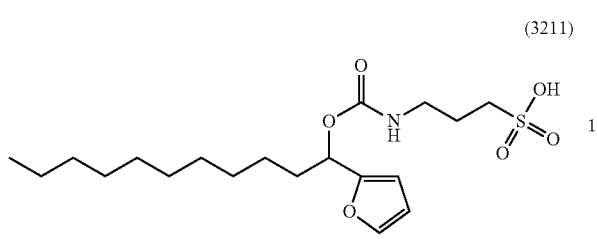
(3211)

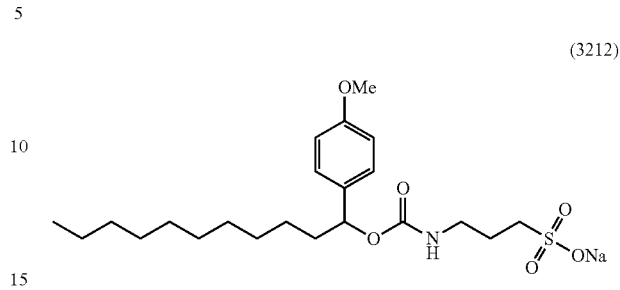
(3212)

2-Furaldehyde (13.4 g, 0.14 mol) was dissolved in 500 mL dry THF and the solution was cooled to 0° C. Decyl magnesium bromide (150 mL of a 1.0 M solution in diethyl ether, 0.15 mol) was added dropwise to the cooled solution, and the reaction allowed to stir overnight. TLC analysis (4:1 ethyl acetate-heptane) indicated the reaction was complete. The reaction mixture was quenched with butanol, followed by water and the mixture was filtered through a sintered-glass funnel and concentrated. The crude product was purified by chromatography on silica gel using a mixture of 4:1 heptane-ethyl acetate to provide 29.7 g (89% yield) of 1-(furan-2-yl)undec-1-ol.

1-(Furan-2-yl)undec-1-ol (4.0 g, 16.8 mmol) was dissolved in 150 mL dry THF and cooled to 0° C. p-Nitrophenyl chloroformate (6.76 g, 33.5 mmol) was added and stirred to dissolve. Pyridine (15 mL) was added dropwise over 20 minutes and the reaction was allowed to stir 1 hour, then analyzed by TLC (7:3 heptane-ethyl acetate). The reaction mixture was filtered to remove pyridine HCl salts. The reaction mixture was evaporated to an oil, co-evaporated twice with acetonitrile, triturated with 100 mL of heptane, and filtered to remove precipitate. The heptane filtrate was evaporated to provide a crude oil. 3-Amino propane sulfonic acid, tetrabutylammonium salt was dissolved in 100 mL of THF and added to the crude oil. The reaction was allowed to stir 1 hour and then analyzed by TLC (9:1 dichloromethane-methanol). The reaction mixture was evaporated to a crude oil and dissolved in 80 mL of water, then filtered to remove precipitate. The resulting solution was passed through 160 grams of cation exchange resin (Diaion® UBK 550, Mitsubishi Chemical Corporation) to convert the product to the sodium salt. The appropriate fractions were combined and lyophilized on a freeze dryer. The fluffy yellow solid was then chromatographed on silica gel using dichloromethane, then 85:15 dichloromethane-methanol to afford a 5.6 g (78% yield) of compound 3211 as a white solid.

p-Anisaldehyde (6.12 g, 45.0 mmol) was dissolved in 250 mL dry THF and the solution was cooled to 0° C. Decyl magnesium bromide (50 mL of a 1.0 M solution in diethyl ether, 50 mmol) was added dropwise to the cooled solution, and the reaction allowed to stir overnight. TLC analysis (4:1 ethyl acetate-heptane) indicated the reaction was complete. The reaction mixture was quenched with butanol, followed by water and the mixture was filtered through a sintered-glass funnel and then evaporated. The crude product was purified by chromatography on silica gel using a mixture of 4:1 heptane-ethyl acetate to provide 10.8 g (86% yield) of 1-(4-methoxyphenyl)undecan-1-ol. 1-(4-Methoxyphenyl) undecan-1-ol (2.0 g, 7.2 mmol) was dissolved in 40 mL dry THF and cooled to 0° C. p-Nitrophenyl chloroformate (2.17 g, 10.8 mmol) was added and stirred to dissolve. Pyridine (5 mL) was added dropwise over 20 minutes and the reaction was allowed to stir 2 hours, then analyzed by TLC (7:3 heptane-ethyl acetate). The reaction mixture was filtered to remove pyridine HCl salts. The reaction mixture was evaporated to a crude oil that was chromatographed on silica gel using 4:1 heptane-ethyl acetate. The resulting 1-(4-methoxyphenyl)undecan-1-ol p-nitrophenyl carbonate was dissolved in 50 mL of THF and treated with 3-aminopropanesulfonic acid, sodium salt (1.35 g, 8.38 mmol). A few drops of water were added to dissolve the reactants. The reaction was allowed to stir overnight, and then analyzed by TLC (9:1 dichloromethane-methanol). The reaction mixture was evaporated to a crude oil that was then chromatographed on silica gel using dichloromethane, then 4:1 dichloromethane-methanol. Appropriate fractions were combined, filtered and evaporated to afford 2.0 g (60% yield) of compound 3212 as a white solid.

Example 3. Preparation of Compound 3266

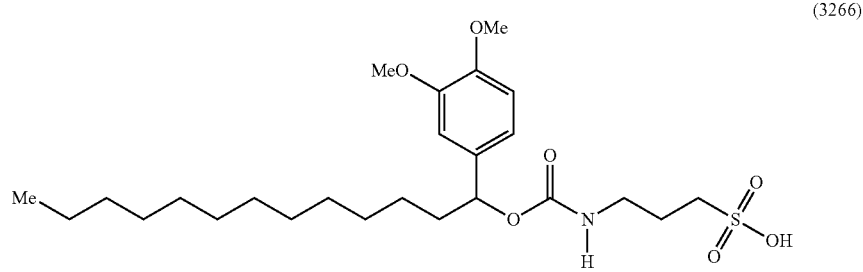 [SMILES: CCCCCCCCCCCCC(OC(=O)NCCCS(=O)(=O)O)c1ccc(OC)c(OC)c1]
(3266)

3, 4-Dimethoxybenzaldehyde (3.15 g, 19.0 mmol) was dissolved in 100 mL dry THF and the solution was cooled to 0° C. Dodecyl magnesium bromide (20 mL of a 1.0 M solution in diethyl ether, 20 mmol) was added dropwise to the cooled solution, and the reaction allowed to stir overnight. TLC analysis (4:1 ethyl acetate-heptane) indicated the reaction was complete. The reaction mixture was quenched with water and the mixture was filtered through a bed of Celite (diatomaceous earth) with heptane-ethyl acetate washes and then evaporated. The crude product was purified by chromatography on silica gel using a mixture of 3:1 heptane-ethyl acetate to provide 5.1 g (80% yield) of 1-(3, 4-dimethoxyphenyl)undecan-1-ol.

1-(3, 4-Dimethoxyphenyl)undecan-1-ol (2.3 g, 6.8 mmol) was dissolved in 20 mL dry THF and to the solution was added p-Nitrophenyl chloroformate (1.64 g, 8.2 mmol), followed by pyridine (2.0 mL). The reaction was allowed to stir 3 hours, then analyzed by TLC (4:1 heptane-ethyl acetate). The reaction mixture was filtered through Celite with heptane-ethyl acetate washings. The filtrate was evaporated to a crude oil that was chromatographed on silica gel using 85:15 heptane-ethyl acetate. The resulting 1-(3, 4-dimethoxyphenyl)undecan-1-ol p-nitrophenyl carbonate 1.54 g, 3.1 mmol) was dissolved in 15 mL of THF and treated with a solution of 3-aminopropanesulfonic acid, sodium salt (0.64 g, 4.0 mmol) in 2 mL of water. The reaction was allowed to stir overnight, and then analyzed by TLC (4:1 dichloromethane-methanol). The reaction mixture was evaporated to a crude oil that was then chromatographed on silica gel using 85:15 dichloromethane-methanol. Appropriate fractions were combined and evaporated to afford 0.48 g (30% yield) of compound 3266 as a white solid.

Example 4. Protocol for Trypsin-Assisted Protein Digestion for Proteins in Solution A surfactant-assisted in-solution digestion protocol was compared with a urea-assisted protocol and both were used to identify a proteome (set of proteins) of membrane proteins from mouse heart. Mouse membrane proteins were digested separately, using urea and surfactant compound 3211, respectively.

Surfactant-Aided Protocol:
Protein from a 50 µg sample of mouse heart membrane extract was precipitated with 4 volumes of ice-cold acetone at −80° C. for 20 minutes. The precipitated membrane protein mixture was collected by centrifugation and the protein pellet was washed with 300 µL of cold acetone. The pellet was solubilized in 20 µL of 0.2% surfactant 3211 (in 50 mM ammonium bicarbonate), then diluted to a volume of 93.6 µL with 50 mM ammonium bicarbonate. After dilution, 1 µL of 0.45M DTT was added and the sample was incubated for 20 minutes at 56° C. DTT reduction was followed by alkylation with 2 µL of 0.7M iodoacetamide for 15 minutes at room temperature.

After alkylation, an additional 1 µL of 1% surfactant 3211 was added followed by 3.5 µL of trypsin (0.5 µg/µL in 50 mM ammonium bicarbonate) and the mixture was digested for 3 hours at 37° C.

Urea-Aided Protocol:
Protein from a 50 µg sample of mouse heart membrane extract was precipitated with 4 volumes of ice-cold acetone at −80° C. for 20 minutes. The precipitated membrane protein mixture was collected by centrifugation and the protein pellet was washed with 300 µL of cold acetone. The pellet was solubilized in 15 µL of 8M urea, and then diluted to a volume of 93.6 µL with 50 mM ammonium bicarbonate. After dilution, 1 µL of 0.45M DTT was added and the sample was incubated for 20 minutes at 56° C. DTT reduction was followed by alkylation with 2 µL of 0.7M iodoacetamide for 15 minutes at room temperature.

After alkylation, 3.5 µL of trypsin (0.5 µg/µL in 50 mM ammonium bicarbonate) was added and the mixture was digested overnight at 37° C.

Surfactant and Urea-Aided Post Digestion Clean-Up and Analysis.

After digestion, 6 µL of 10% TFA was added and the mixture was incubated for 15 minutes at 37° C. Following this acid degradation step the sample was extracted on a 100 µL C18 OMIX tip (Varian, Inc.) following the manufacturer's instructions, eluting with 20 µL of 70% acetonitrile, 0.1% TFA. Each digest mixture was analyzed by 1D nanoLC-MS/MS.

Figure 4A:
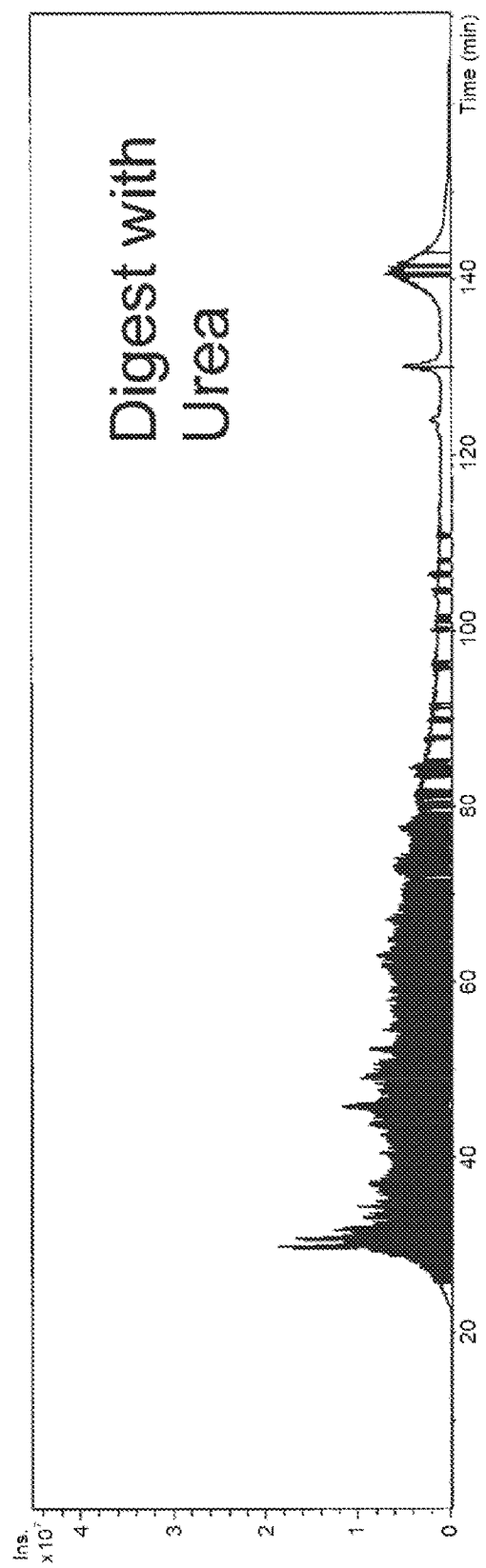
FIG. 4A shows a total ion chromatogram for digests of mouse membrane proteins using urea.
Figure 4B:
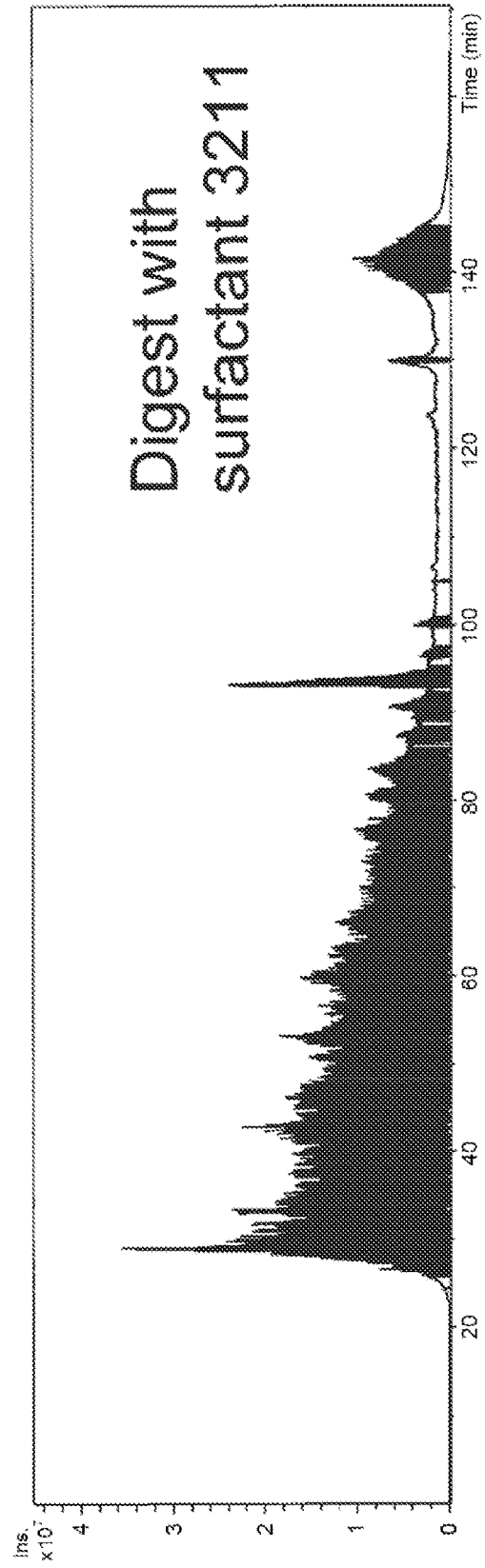
FIG. 4B shows a total ion chromatogram for digests of mouse membrane proteins using surfactant compound 3211.
Figure 5:
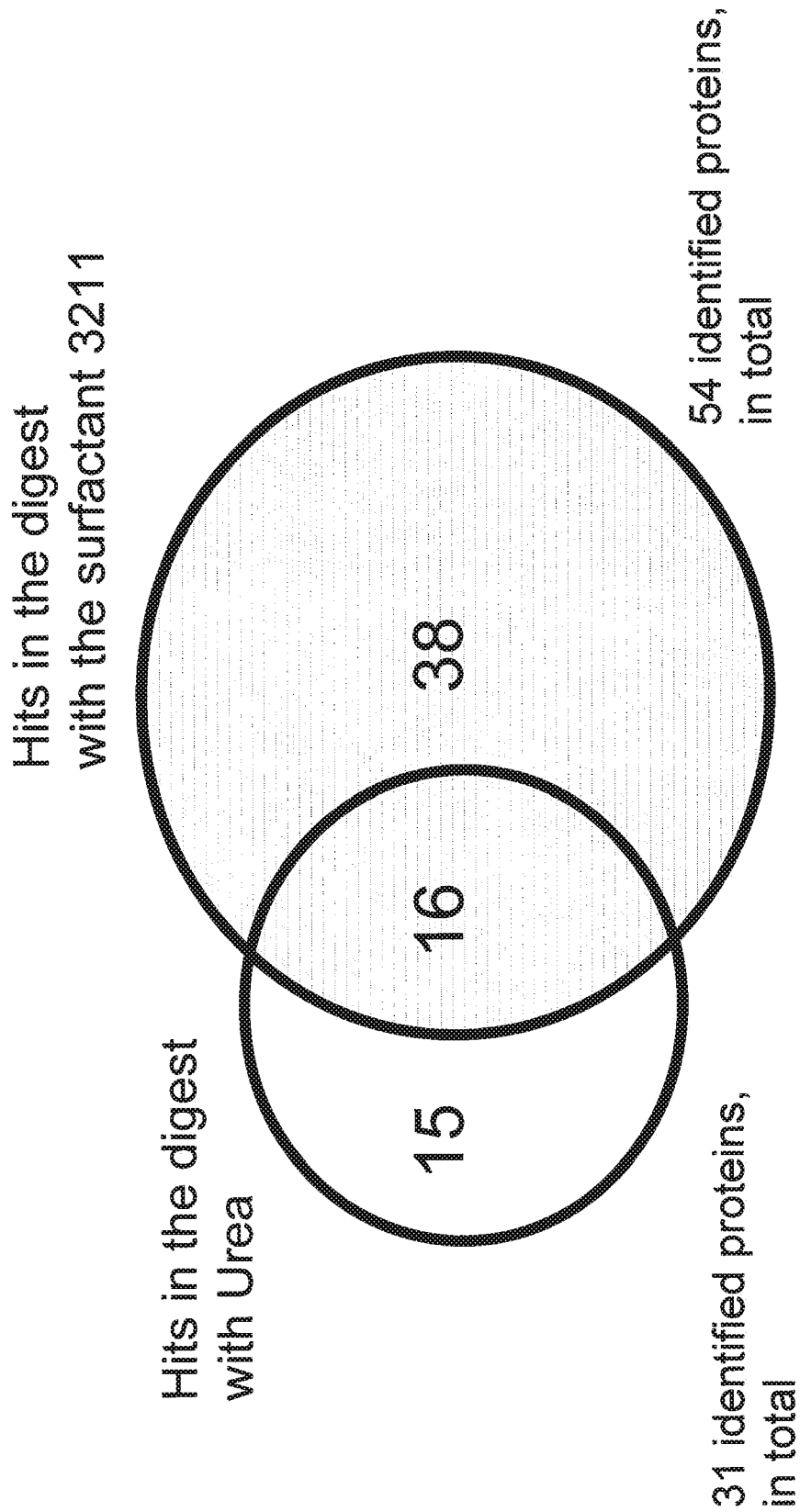
FIG. 5 illustrates the Mascot search results for digests of mouse membrane proteins, using urea and surfactant compound 3211 separately; the count of identified proteins specific to urea and compound 3211 digests, and overlapping identified proteins are illustrated.

FIG. 4A and FIG. 4B show the total ion chromatogram (TIC) for each digestion. As can be observed from the figures, peptide yield and number of identified peptides were higher in the digest using surfactant compound 3211. FIG. 5 shows that the surfactant-assisted protocol allowed for ~70% increase in proteome coverage versus urea (standard solubilizer for membrane proteins)-assisted protocol.

While 31 proteins were identified in the membrane protein digest with urea, 54 proteins were identified in the membrane protein digest using surfactant compound 3211. A higher individual protein coverage was also obtained using surfactant compound 3211. The score and coverage for Atp5b was almost double of that obtained using urea. Atp5b protein from digest with urea resulted in a score of 384 and 8 peptides (22.5% coverage), while Atp5b protein from digest with compound 3211 resulted in a score of 707 and 15 peptides (42.4% coverage).

It was found that only a portion of identified proteins were common in both digests, while the remaining digests were specific for either digest, as illustrated in FIG. 5. The use of surfactants of the invention therefore allow for larger proteome coverage when used in conjunction with a separate urea digest. A digest using a combination of urea and a surfactant disclosed herein can also be employed. In such a protocol, each of the proteins identifiable by either reagent, both urea- and surfactant-specific, can be identified in one digest.

Example 5. Protocol for Trypsin-Assisted Protein Digestion for Proteins 'in Gel'

The following is a standard 'in-gel' digestion sample preparation protocol, followed by a description of a sample preparation protocol using surfactant of the invention.

Materials: Gel staining solution (for example, with Coomassie Blue); Gel destaining solution (for example, 40% Ethanol/10% Acetic acid); Highly pure distilled water; 50 mM Ammonium Bicarbonate (AmBic); 25 mM Dithiothreitol (DTT); 55 mM Iodoacetamide (IAA); Acetonitrile (ACN); Trypsin; and Trifluoroacetic acid (TFA).

Standard Protocol:
1. Resolve proteins in polyacrylamide gel and stain proteins with Staining solution.
2. Destain the gel with Destaining solution to remove nonspecifically bound stain.
3. Excise protein band of interest, cut the gel slice onto 1 mm³ pieces and transfer into 0.5 or 1.5 mL microcentrifuge polypropylene tube.
4. Wash the pieces with water.
5. Destain the pieces twice with Methanol: 50 mM AmBic=1:1 (v/v).

6. Dehydrate for 5 minutes with ACN: 50 mM AmBic=1:1 (v/v), then for 30 seconds in 100% ACN.

7. Dry in Speed Vac for 5 minutes.

8. Rehydrate in freshly prepared 25 mM DTT and incubate at 56° C. for 20 minutes.

9. Discard DTT solution and add freshly prepared 55 mM IAA. Incubate in the dark at room temperature for 20 minutes.

10. Wash twice with water.

11. Dehydrate for 5 minutes with ACN: 50 mM AmBic=1:1 (v/v), then for 30 seconds in 100% ACN.

12. Dry in Speed Vac for 5 minutes.

13. Rehydrate for 5 minutes in 20 uL 12 ng/uL Trypsin Gold (in 50 mM ACN M AmBic). Overlay with minimal amount of 50 mM AmBic to cover gel pieces. Incubate overnight at 37° C.

14. Mix the slices with 50 uL 2.5% TFA on Vortex or orbital shaker for 15 min. Save the extract.

15. Add 80 uL 70% ACN/5% TFA and mix on Vortex or orbital shaker for 15 minutes.

16. Combined both extracts and dry with Speed Vac for 1.5-2 hours.

17. Redissolve peptides in 30 uL 0.1% TFA by mixing on Vortex for 5 minutes and clean-up peptides with $C_{18}$ tips. Analyze with MALDI-TOF.

Sample Preparation with an Enzyme Surfactant as Disclosed Herein.

Materials: Gel staining solution (for example, with Coomassie Blue); Gel destaining solution (for example, 40% Ethanol/10% Acetic acid); Highly pure distilled water; 50 mM Ammonium Bicarbonate (AmBic); 25 mM Dithiothreitol (DTT); 55 mM Iodoacetamide (IAA); Acetonitrile (ACN); Trypsin; Trifluoroacetic acid (TFA); an enzyme (e.g., trypsin) surfactant A. Surfactant A refers to an acid-labile and/or thermolabile surfactant as disclosed herein.

Improved Protocol:

1.-12. Steps as above.

13. Rehydrate for 5 minutes in 20 μL 12 ng/μL Trypsin Gold (in 0.025% surfactant A/50 mM ACN M AmBic). Overlay with 30 μL of 0.01% surfactant A/50 mM AmBic to cover gel pieces. Incubate 1 hour at 50° C.

14. Transfer the digestion reaction into a new tube and analyze the digestion reaction with mass spectrometry.

Figure 6:
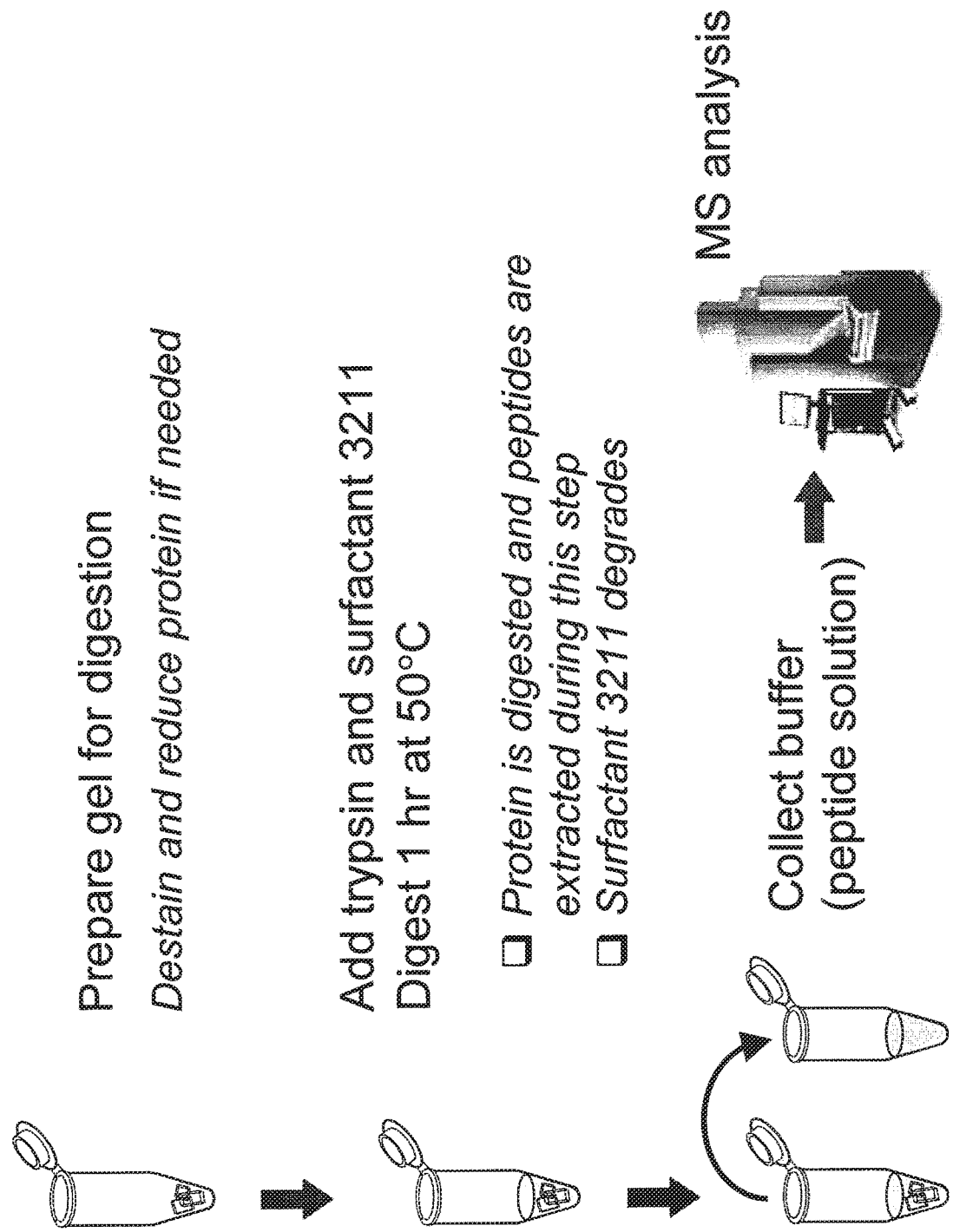
FIG. 6 illustrates a 1 hour in-gel digestion protocol with the aid of a surfactant (compound 3211), according to one embodiment of the invention.

The surfactant-assisted protocol illustrated in FIG. 6 demonstrates a significant innovation to in-gel protein digestion. Typical in-gel digestion protocol includes two steps: protein digestion that generally takes overnight (8-24 hours) and peptide extraction, which typically includes two extractions, including TFA and a TFA/acetonitrile mixture, followed by peptide concentration with 1.5-2 hours of drying in a Speed-Vac® concentrator, and reconstitution in a small volume of TFA. In the surfactant-assisted protocol, both steps are combined into a single one hour step leading to dramatic increases in efficiency, including reduced time and labor required to complete the protocol.

Figure 7A:
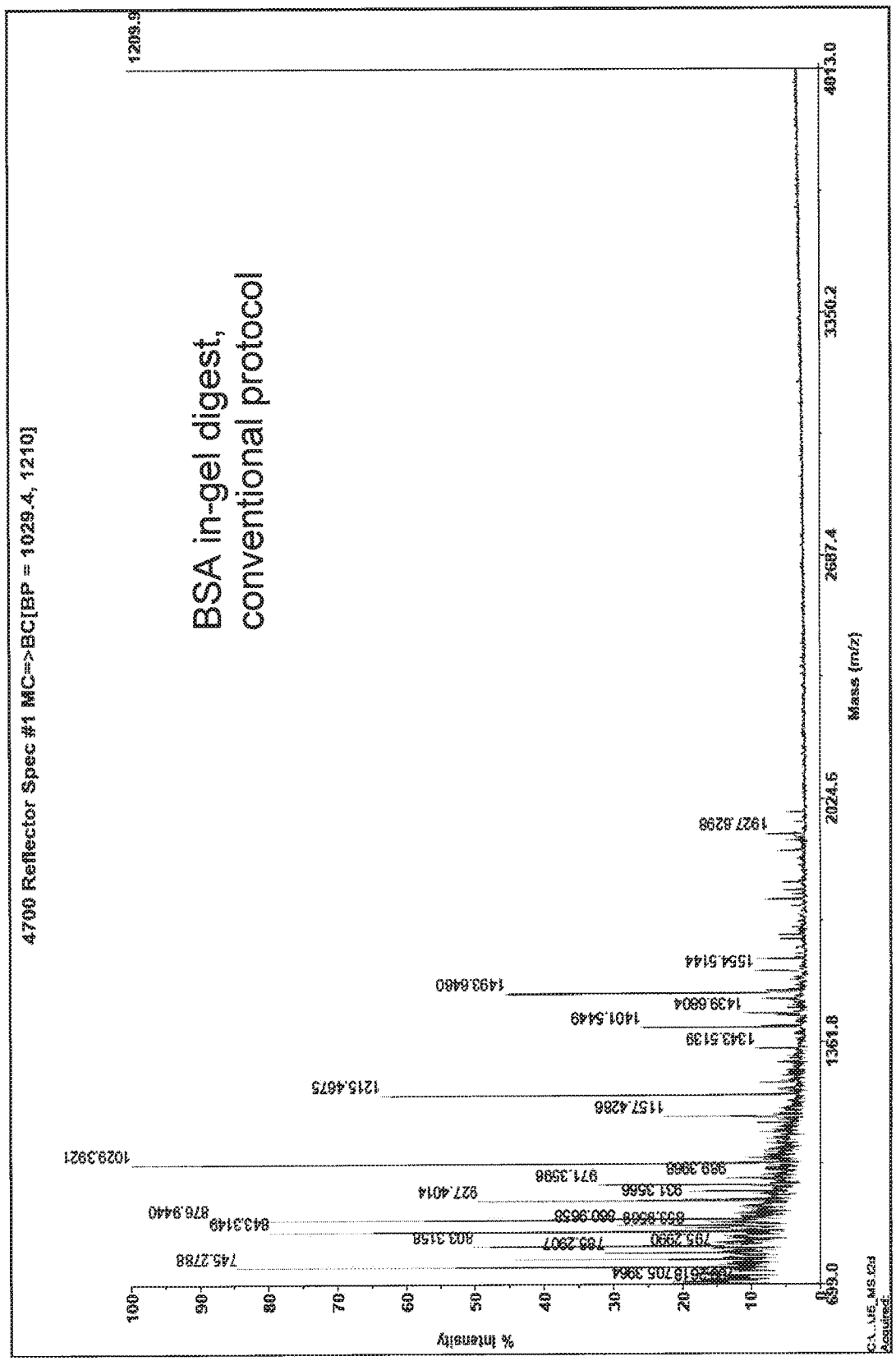
FIG. 7A and FIG. 7B illustrate peptide extraction with the aid of a surfactant, according to an embodiment of the invention.
Figure 7B:
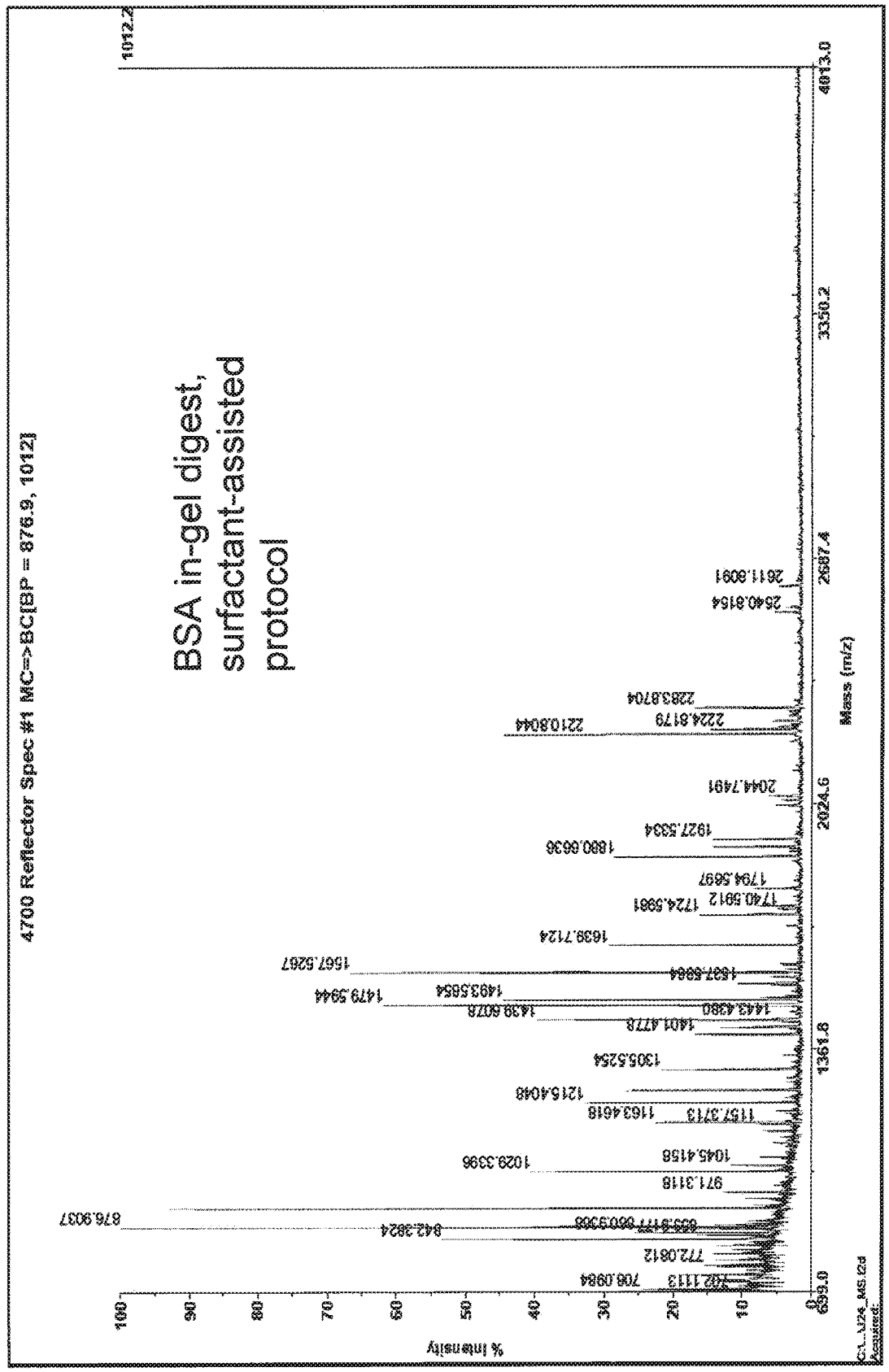

FIG. 7A and FIG. 7B illustrate experimental evidence showing that the surfactants of the invention extract more peptides, and higher molecular weight peptides, from the gel. The figures show spectra of peptides present in a digestion mix, as discussed in the two protocol above. FIG. 7A illustrates peptides present in a digestion reaction after overnight digestion of BSA (50 ng) without the aid of a surfactant of the invention. FIG. 7B shows the digestion reaction results after one hour digestion with the aid of a surfactant of the invention. The surfactant dramatically increases peptide recovery, leading to increases in protein coverage to 36%, up from 8% in a conventional protocol.

Use of surfactant 3211 instead of organic solvent in extraction step allows one to avoid a time-consuming vacuum drying step (1.5-2 hours) that is required to remove the solvent that, otherwise, interferes with the peptide clean-up step. In addition, the vacuum drying step can lead to loss of substantial amount of peptides due to strong absorption to tube walls. The use of surfactant 3211 ensures high recovery of peptides by preventing this absorption.

The surfactant offers several improvements over regular protocols for in-gel protein digestion, including improved protein digestion, improved trypsin stability, and an innovative surfactant-facilitated peptide extraction as described herein. Combination of these improvements lead to a 2.2 fold improvement in protein coverage and 6.8 fold improvement in Mascot score in experiments conducted using the above protocol.

The surfactants of the invention offer additional innovations to protein digestion for both 'in-solution' and 'in-gel' techniques. Earlier developed trypsin surfactants, such as RapiGest™ and PPS Silent Surfactant™, require incubation of protein digestion mixture with acid to degrade surfactant that can otherwise interfere with downstream applications, such as liquid chromatography and mass spectrometry analysis. An important advantage of the surfactants of the invention is that they degrade by end of the recommended digestion incubation time (3 hours) or during preparation of extracted peptides for clean-up step to such an extent that no additional degradation is required.

If the surfactant of the invention still remains intact (for example, if protein digestion was shorter than 3 hours) and further degradation is required, the surfactant can be degraded by elevated temperature as an option to acid degradation. Currently used products (e.g., RapiGest™ surfactant and PPS Silent Surfactant™) require acid degradation. No evidence that those surfactants can be degraded by elevated temperature is available. Thermodegradation allows for more flexibility with downstream treatment of digested peptides. For example, a researcher has option to add formic acid instead of TFA to peptide solution and directly proceed to peptide separation by liquid chromatography. Thermodegradation can lead to a better recovery of acid labile post-translational modifications (such as acid labile glycans). Additionally, thermodegradation will be preferred by researchers over acid degradation to avoid the necessity of handling any hazardous chemical material such as strong acids (e.g., TFA) in the protocol.

The protocol can also be aided by use of a urea/surfactant combination. A more diverse population of identified proteins can be observed in digests performed in the presence of urea/surfactant mixtures that in the presence of either agent alone.

Example 6. Trypsin-Assisted Protein Digestion for Proteins 'in Gel'

Total membrane protein from mouse heart was resolved in SDS-polyacrylamide gel and a single protein band was digested with a conventional digestion protocol (control) and separately with a compound 3211-assisted protocol.

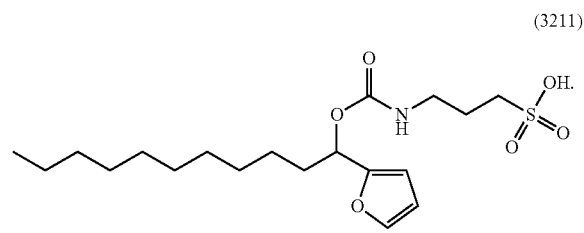 [SMILES: CCCCCCCCCCC(OC(=O)NCCCS(=O)(=O)O)c1ccco1]

Figure 8A:
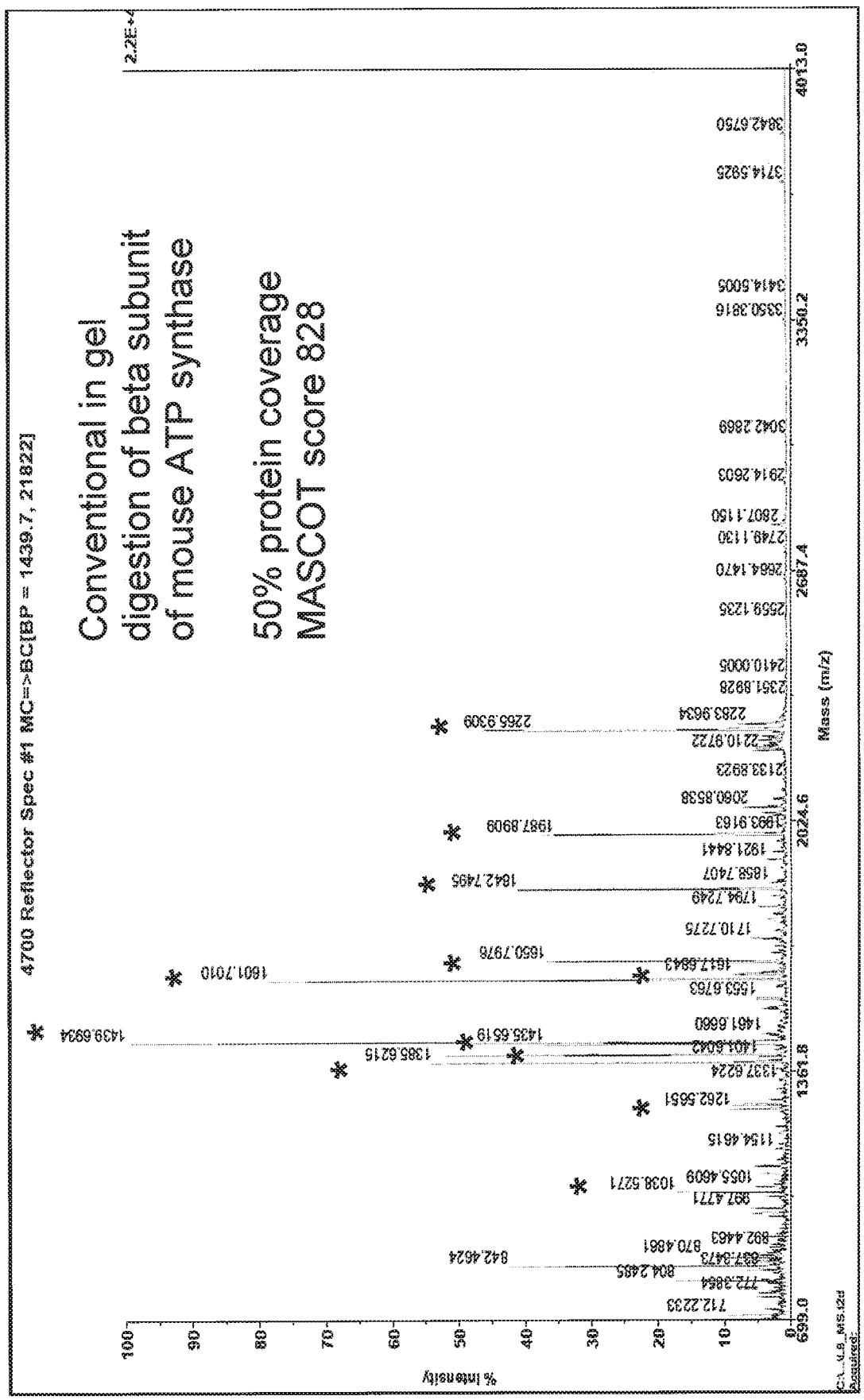
FIG. 8A and FIG. 8B illustrate mass spectra of an in-gel digest of an approximately 56 kD band from mouse membrane protein extract.
Figure 8B:
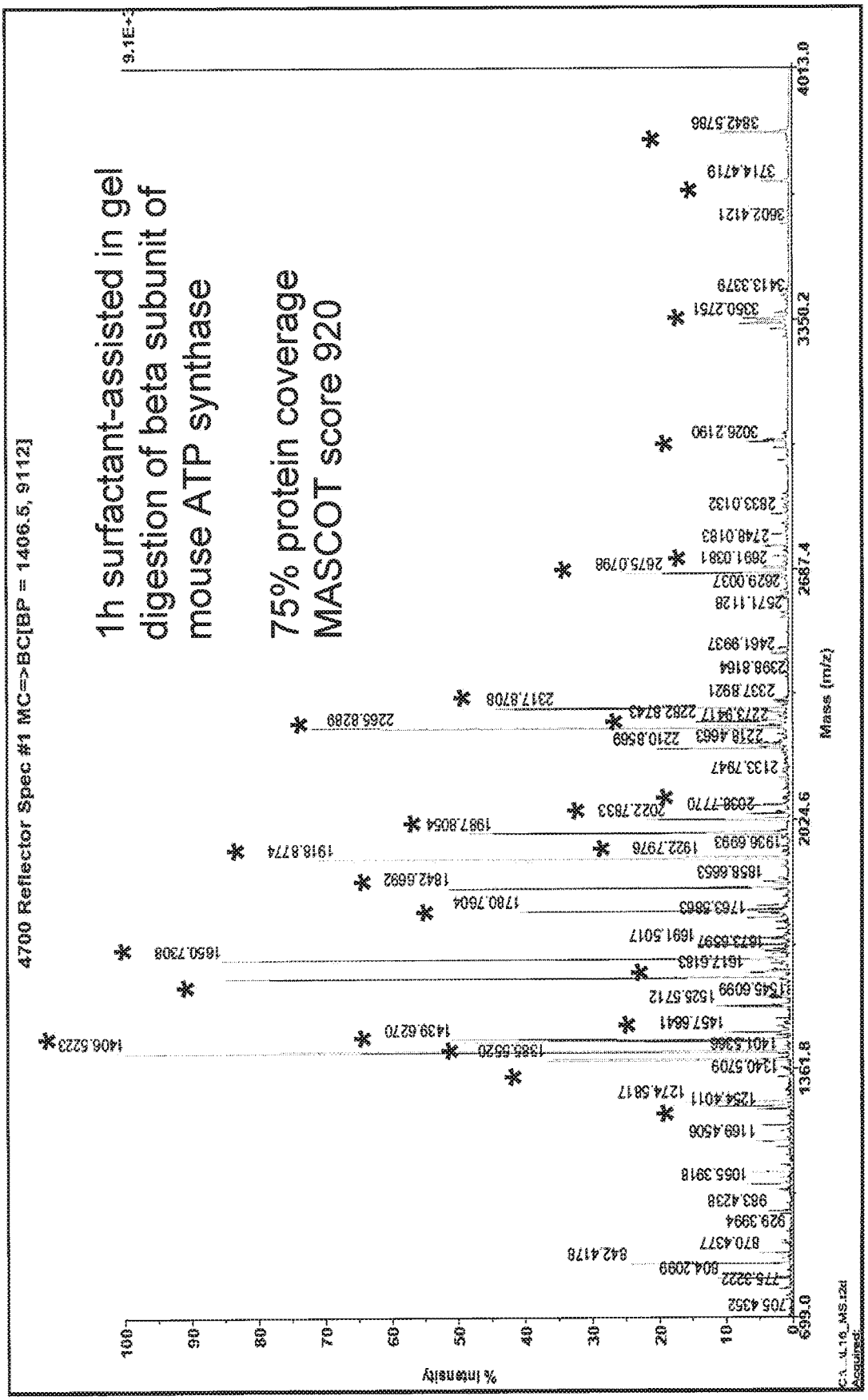

A band of the protein with an approximate MW of 56 kD was excised and digested with trypsin. The digested samples were analyzed by mass spectrometry. FIG. 8A and FIG. 8B show the mass spectra of the two analyses; FIG. 8A shows the spectrum obtained from the conventional overnight protocol without surfactant 3211; FIG. 8B shows the spectrum obtained from the protocol that employed surfactant 3211 and only 1 hour of digestion. Asterisks indicate identified peptides for beta subunit of mouse ATP synthase (the major protein in 56 kD band).

FIG. 8B shows a dramatic increase in the number, and yield, of peptides obtained using the surfactant of the invention protocol. The protocol without surfactant provided sequence coverage for beta subunit of ATP synthase of 50% and a MASCOT score of 828, while the surfactant aided protocol provided a 75% sequence coverage (a 50% increase) and a MASCOT score of 920. Use of a surfactant of the invention, such as compound 3211, substantially improves mass spectrometry protein identification and simplifies in-gel digestion protocol by combining lengthy protein digestion and peptide extraction steps into a single one hour step.

One dimensional (1D) gel techniques are frequently used to fractionate complex protein mixtures. A protein mixture is resolved in-gel and the gel line is cut onto gel slices. Each gel slice represents a protein fraction. The fractions are then in-gel digested and digested peptides are then identified using LC-MS/MS. Use of the surfactants of the invention afford significant savings in terms of time and labor in preparing gel-fractionated proteins for mass spec analysis.

Figure 9:
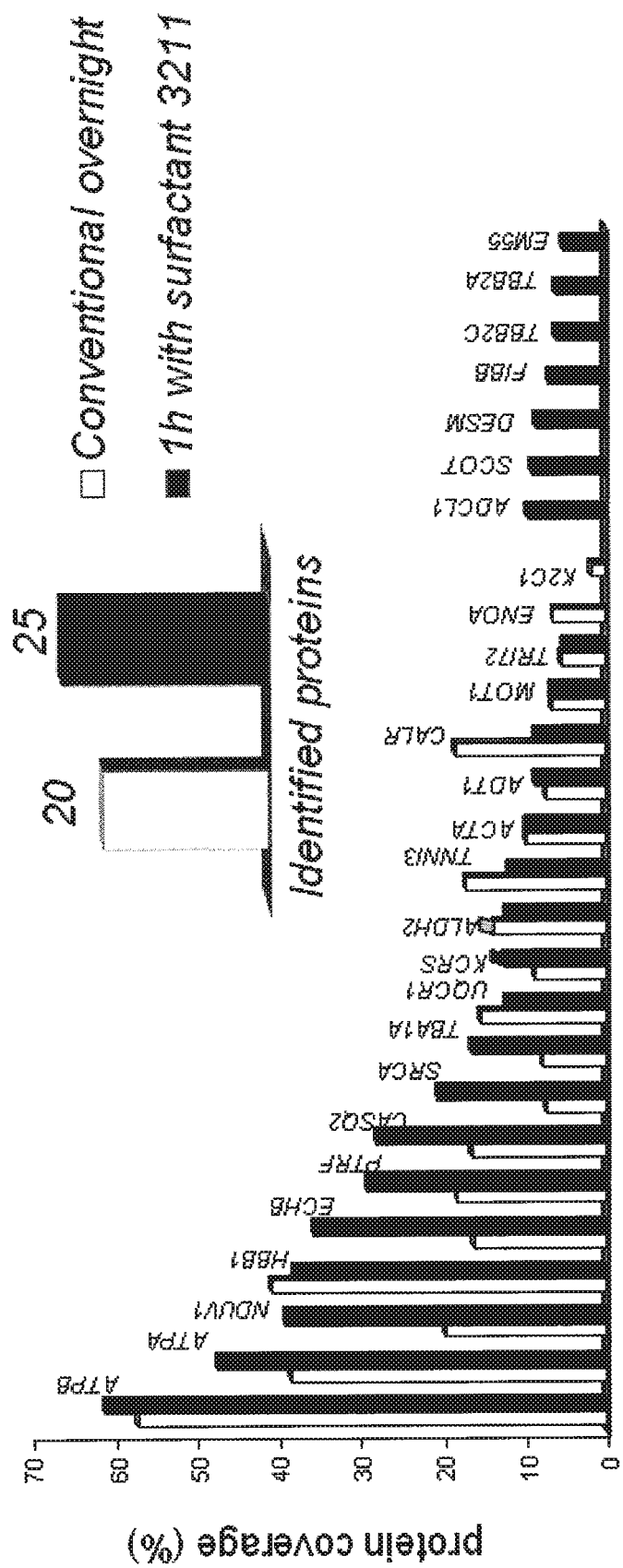
FIG. 9 illustrates analysis of the protein band of FIG. 8 with LC-MS/MS. The graph shows the number of proteins identified with overnight digestion without the aid of compound 3211. It also shows protein coverage for each identified protein achieved with either protocol.
Figure 10:
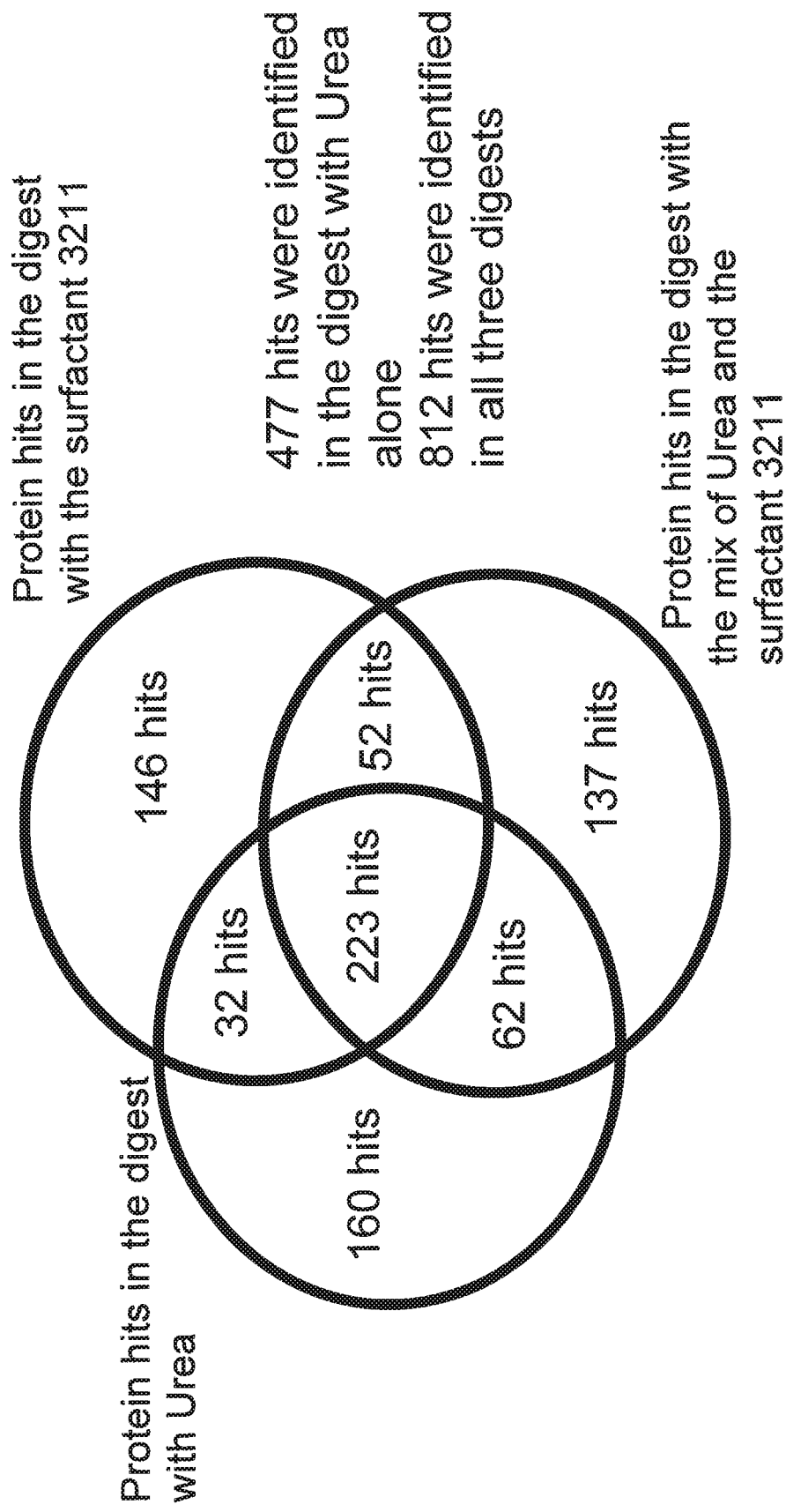
FIG. 10 illustrates results of 2D LC-MS/MS analysis of mouse heart membrane proteome. The membrane protein was solubilized under three different conditions: urea, surfactant or urea/surfactant mix. Each condition was digested with trypsin and analyzed with off-line 2D LC-MS/MS with an Agilent 1100 series LC/MSD Trap SL spectrometer.
Figure 11A:
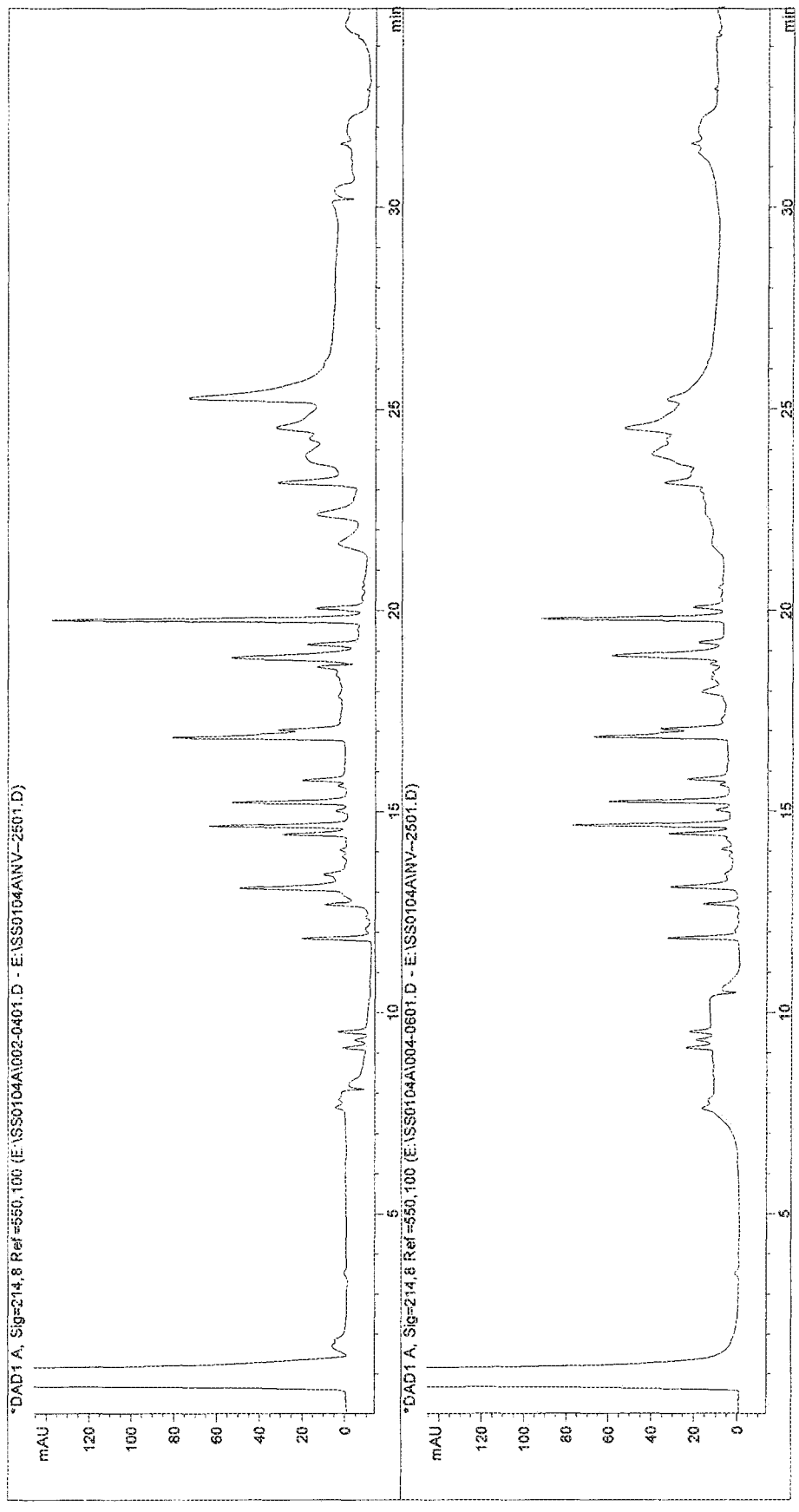
FIG. 11A illustrates the comparative effect of compound 3116 to aid in the digestion of Myoglobin with Trypsin as compared with the commercially available surfactant RapiGest™ (Waters, Inc).
Figure 11B:
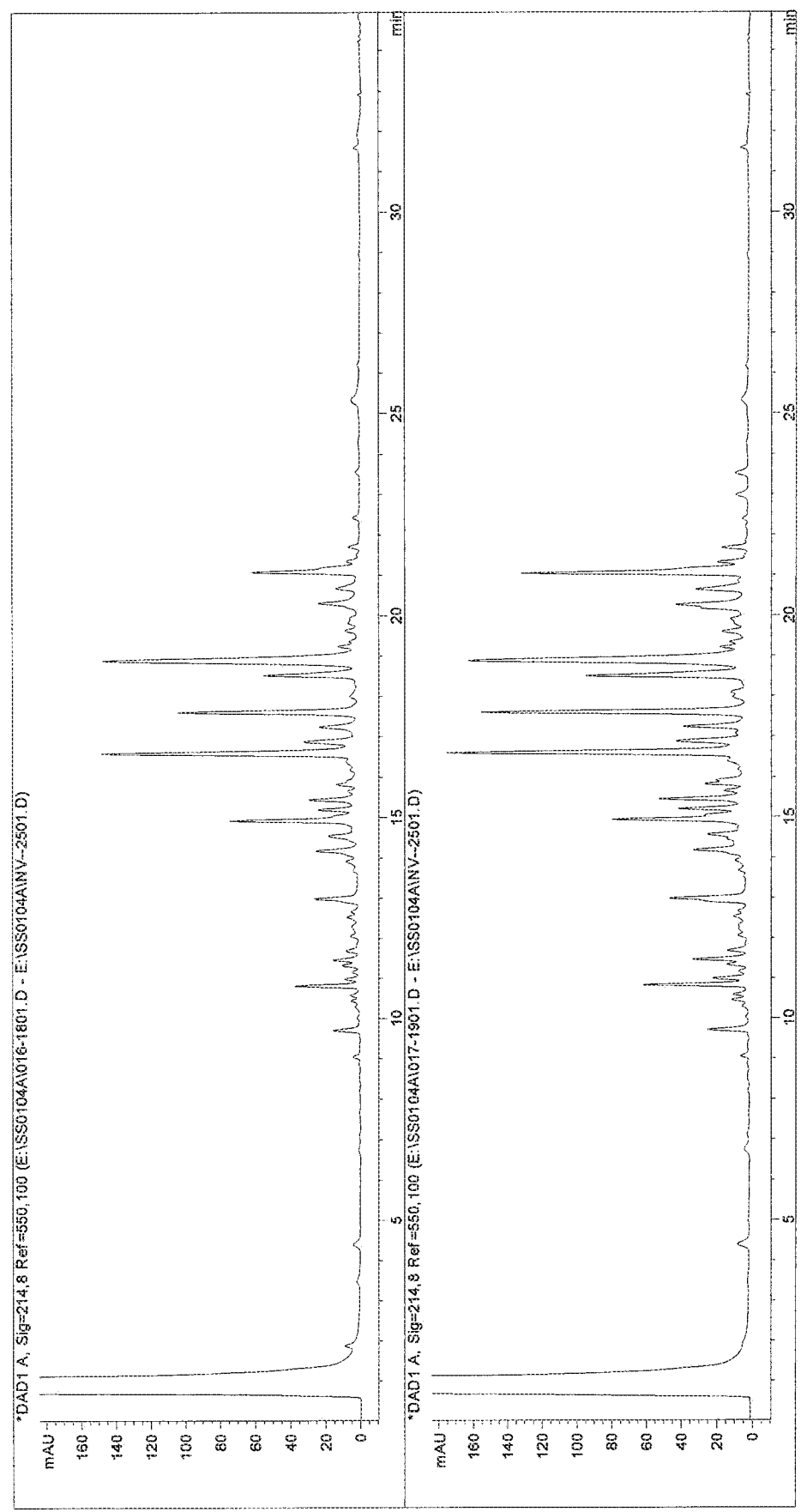
FIG. 11B illustrates the effect of compound 3116 to aid in the solubilization and digestion of Bacteriorhodopsin with Chymotrypsin as compared with the commercially available surfactant RapiGest™ (Waters, Inc). In both FIG. 11A and FIG. 11B, the upper chromatogram is the RapiGest™ surfactant assisted digestion reaction (control) and the lower chromatogram is the result obtained with compound 3116. Typical reaction and HPLC conditions are described in Example 12.
Figure 12A:
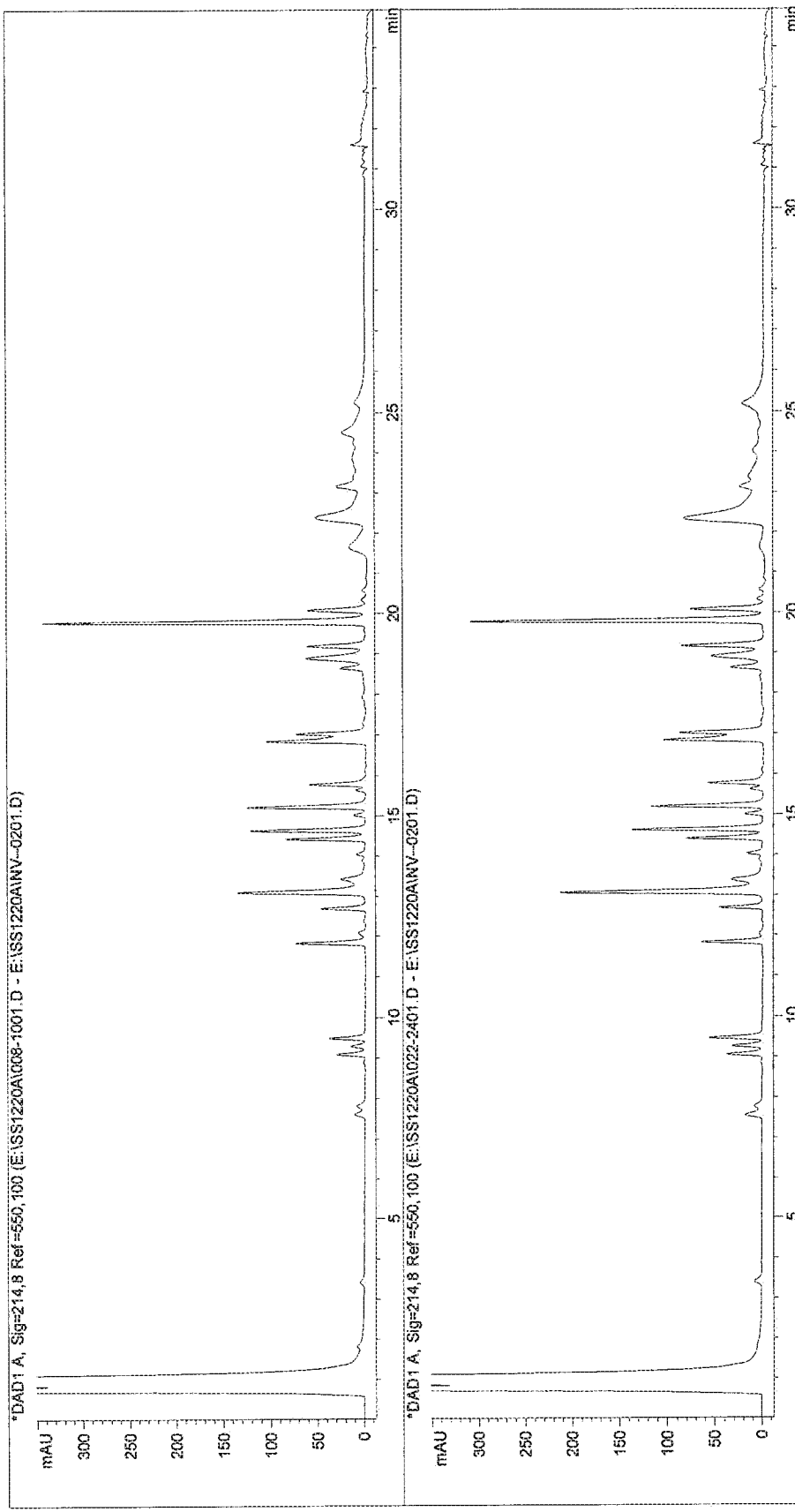
FIG. 12A illustrates the comparative effect of compound 3202 to aid in the digestion of Myoglobin with Trypsin as compared with the commercially available surfactant RapiGest™.
Figure 12B:
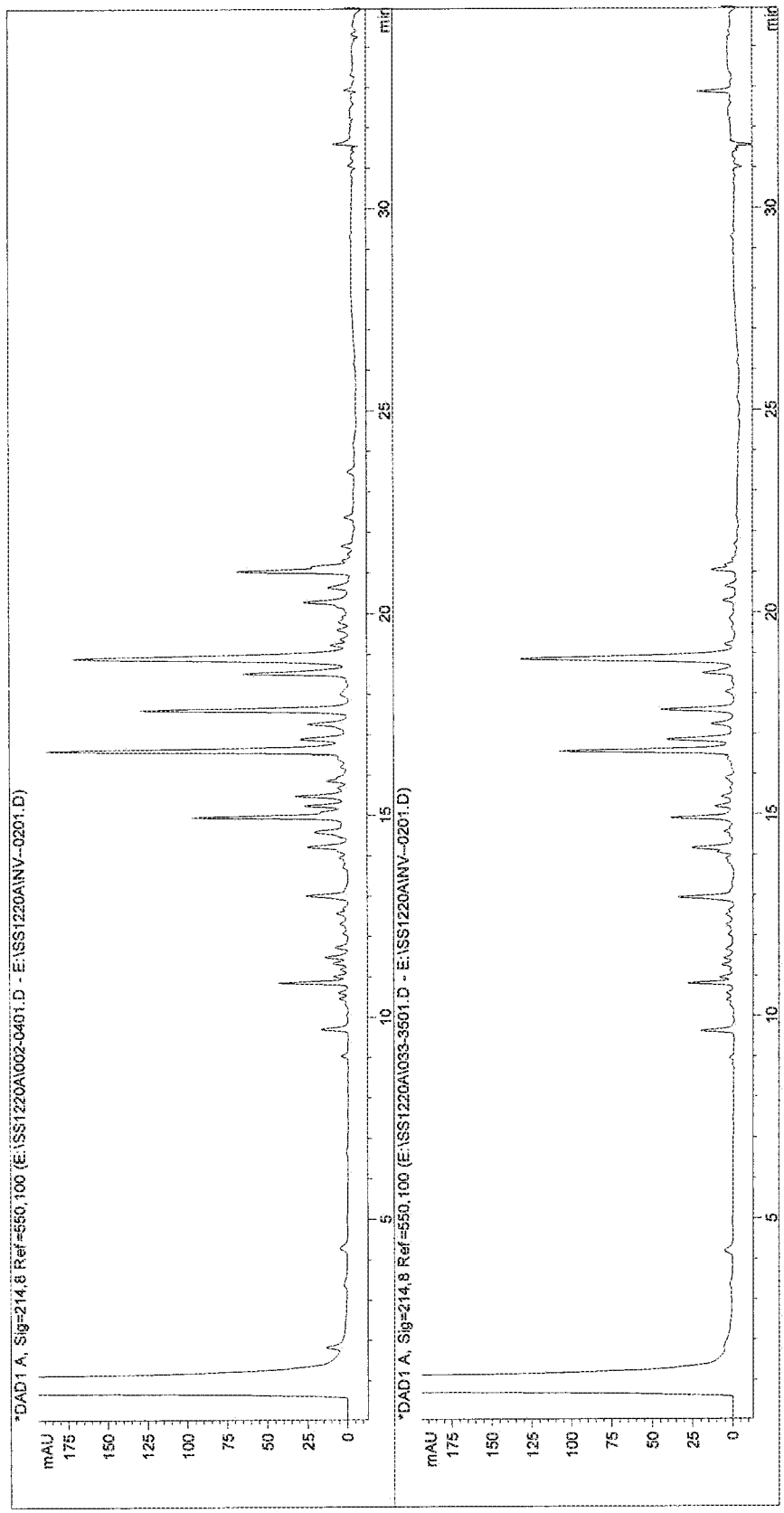
FIG. 12B illustrates the effect of compound 3202 to aid in the solubilization and digestion of Bacteriorhodopsin with Chymotrypsin as compared with the commercially available surfactant RapiGest™. In both FIG. 12A and FIG. 12B, the upper chromatogram is the RapiGest™ surfactant assisted digestion reaction (control) and the lower chromatogram is the result obtained with compound 3202. Typical reaction and HPLC conditions are described in Example 12.

FIG. 9 illustrates how the surfactant-assisted one hour protocol provides a satisfactory or superior method for identification of complex protein mixtures in gel. In the experiment, a membrane protein extract from mouse heart was resolved in 4-20% SDS-PAGE and the fraction containing proteins with approximate MW of 54-56 kD was analyzed with LC-MS/MS. The number of proteins identified after a one hour digestion with the surfactant was greater than number of proteins identified with a conventional overnight digestion protocol. Additionally, higher protein coverage was achieved for one third of the identified proteins in the surfactant-assisted protocol.

Example 7. Trypsin-Assisted Protein Digestion for Proteins 'in Gel'

A surfactant of the invention can improve in-sodium dodecyl sulfate polyacrylamide gel protein digestion for matrix-assisted laser desorption/ionization mass spectrometric peptide mapping. Mass spectrometry, in conjunction with genome database searches, is a tool for the identification of proteins. In proteome analysis, mixtures of cellular proteins are often separated by sodium dodecyl sulfate (SDS) polyacrylamide gel-based one-dimensional gel electrophoresis (1-DE) or two-dimensional gel electrophoresis (2-DE), and in-gel digested by a specific protease. In-gel protein digestion is an important step for sensitive protein identification by these procedures. Efficient protein digestion is helpful for obtaining the peptide peaks necessary for clear protein identification by mass spectrometry.

A significant improvement of protein digestion in SDS polyacrylamide gels using an surfactant of the invention can be obtained. The surfactants described herein can also dramatically improve peptide yields by making peptide extraction more efficient (for example, see the techniques described by Nomura et al., J. Mass Spec. 2004, 39(2), 202-207, and specifically page 203 for 'in-gel' digestion and extraction of peptides with a surfactant, incorporated by reference herein), and by preventing absorption of peptides by labware, or by preventing peptide loss due to precipitation. This provides a useful strategy for sensitive protein identification by mass spectrometry. The surfactants described herein also offer a dramatic simplification to in-gel protein digestion by combining lengthy protein digestion and peptide extraction into a single one hour step.

Example 8. Trypsin-Assisted Protein Digestion for Proteins 'in Solution'

Standard biochemical techniques used for protein isolation, such as affinity isolation and density gradient centrifugation, can provide nanogram to low-microgram quantities of protein material with a significant amount of labor and time. The effectiveness of mass spectrometry characterization of isolated protein by a "shotgun" approach is often reduced by a lack of effective and efficient in-solution proteolysis protocols for these small quantities of proteins. Proteolytic peptides can be analyzed by one-dimensional liquid chromatography-tandem mass spectrometry (LC-MS/MS). The effectiveness of a digestion protocol can be assessed on the basis of, for example, three parameters: number of peptide identifications, number of protein identifications, and sequence coverage. Use of 80% acetonitrile for trypsin digestions can be advantageous, and is often better than protocols employing other solvents and chaotropes in various protein isolates. A primary advantage of the 80% $CH_3CN$ protocol is that it can require fewer sample manipulation steps. See for example, the methods used to denature proteins prior to digestion with trypsin for 'in-solution' reactions discussed by Hervey et al., J. Proteome Res. 2007; 6(8); 3054-3061, in particular, the discussion at page 3055, incorporated by reference herein.

Example 9. Surfactant-Assisted Protein Digestion for Proteins 'in Solution'

An optimization and comparison of trypsin digestion strategies for peptide/protein identifications by LC-MS/MS with or without mass spectrometry compatible detergents in mixed organic-aqueous and aqueous systems can be carried out using the acid- and thermolabile compounds disclosed herein. It can be shown that adding mass spectrometry-compatible surfactants to proteolytic digestion protocols dramatically increases peptide and protein identifications in complex protein mixtures by shotgun proteomics. Protein solubilization and proteolytic efficiency can be increased by including mass spectrometry-compatible detergents in trypsin digestion buffers.

A modified trypsin digestion protocol incorporating the mass spectrometry-compatible surfactants can aid in the identification of proteins from, for example, pancreatic cell lysates, and can generate a greater number of peptide identifications than trypsin digestion with urea when using LC-MS/MS. Additionally, proteins can be identified by merging protein identifications from trypsin digestion with various mass spectrometry-compatible surfactants. It can also be observed that the use of mixed aqueous and organic solvent systems can influence protein identifications in combinations with different mass spectrometry-compatible surfactants.

Peptide mixtures generated from different mass spectrometry-compatible surfactants and buffer combinations can show a significant difference in hydrophobicity. Experimental results show that protein digestion schemes incorporating mass spectrometry-compatible surfactants can generate quantitative as well as qualitative changes in observed peptide identifications, leading to increased protein identifications overall and increased identification of low-abundance proteins. See for example, the techniques described by Chen et al., *J. Proteome Res.* 2007; 6(7); 2529-2538, and in particular at page 2531 for a discussion of the ability of acid-labile surfactants to improve proteolysis of complex protein mixtures with trypsin, incorporated by reference herein.

The surfactants described herein not only improve protein solubilization and digestion, they also substantially increase peptide yield by preventing peptide loss due to absorption by labware or precipitation. This three-way benefit makes the surfactants an ideal means for in-solution digestion protocol. Initial evidence indicates that the surfactants can be also used in combination with urea, a standard solubilizing agents for in-solution digestion protocol. The surfactants can retain all of their beneficial properties in the presence of urea. Digestion in urea/surfactant mixture can provide a larger number of identified proteins, larger individual protein coverage, and improved mass spectrometric analysis data than with the use of these the agents individually.

Example 10. Cyanogen Bromide Protein Digestion

In protein digestion, cyanogen bromide (CNBr) acts by cleavage of a protein at methionine residues resulting in a homoserine lactone on the carboxyl fragment. Cyanogen bromide is useful for analysis of membrane proteins because methionine residues are often located in hydrophobic regions of a protein and cleavage advantageously reduces the size of the hydrophobic fragment, which increases the efficiency and effectiveness of analysis. Cyanogen bromide can be used by itself to produce large fragments, or in series prior to a protease such as trypsin or chymotrypsin. Typical protocols require some type of surfactant to aid in solubilization of the protein mixture of interest before reacting the protein with an excess of CNBr in the dark for 24 hours. The digest reaction requires low pH so it is often run in 50-80% TFA of HCl solutions. Typical solubilizing agents may need to be removed from the reaction before analysis while excess CNBr is volatized.

The surfactant compounds of formula I-IX can be used to aid in the solubilization of a membrane protein mixture, followed by adjustment of the reaction conditions to low pH, thereby degrading the surfactant prior to addition of CNBr. Following digestion the sample can be analyzed directly by MALDI with no need to remove the denaturing agents that would otherwise interfere in ionization.

Example 11. Deglycosylation Techniques Using Surfactants

Glycosylation is important post-translational protein modification implicated in many key cellular mechanisms and disorders. In fact, about 60% of human proteins are glycosylated. A protein can be glycosylated at various sites with different types of carbohydrates. The function of a protein is affected in different ways, depending on which site of a protein is glycosylated, and what type of carbohydrate is attached. Accordingly, glycosylation analysis presents significant challenges, and improved techniques for conducting the analyses are needed.

Mass spectrometry is a major analytical tool for study of glycosylation. This powerful technique allows for localizing sites of glycosylation and identifying carbohydrate structures. One significant challenge is that the protein and carbohydrate moieties of a glycoprotein should be physically separated for efficient and effective analysis, i.e., each moiety must be analyzed separately to obtain appropriate data. The separation of these moieties can be achieved by enzymatic deglycosylation. Enzymatic deglycosylation is often time-consuming and/or inefficient because glycosylated sites of glycoproteins are often obstructed by a protein's structure.

To allow glycosidases easy access to glycosylated sites of a protein, researchers frequently use SDS. SDS greatly improves deglycosylation, however it interferes with mass spectrometric analysis. Researchers studying cancer, cellular mechanisms, and other biological problems routinely treat protein samples with glycosidases prior to mass spectrometric analysis. The information commonly sought includes which sites of a protein of interest carry carbohydrates. These sites can be localized after deglycosylation because glycosidases leave behind a small portion of carbohydrates after cleavage. This remaining portion acts as marker of glycosylated site in mass spectrometric analysis. Some researchers are also interested in analyzing the cleaved carbohydrates.

Surfactants described herein were evaluated as replacements for SDS in deglycosylation protocols. Ovalbumin (albumin from chicken egg white) was selected as a model protein. Ovalbumin is a 44.3 kD glycoprotein with 1.4 kD carbohydrate units linked to the protein. Ovalbumin deglycosylation is inefficient under standard conditions, even after overnight incubation with PNGase F. The ovalbumin was treated with glycosidase PNGase F. It was found that, in the presence of surfactant compound 3266, PNGase F rapidly removed carbohydrate from ovalbumin. Surfactant compound 3266 is acid-labile and it can be easily degraded, allowing for analysis of the protein and carbohydrate using mass spectrometric analysis.

Detailed Protocol:

Ovalbumin (Sigma) (45 μg) was dissolved in 0.025% 3266/5 mM DTT/25 mM ammonium bicarbonate (pH ~8) and incubated at 95° C. for 5 minutes. In the control reaction, 3266 was replaced with SDS. Deglycosylation was initiated by adding 1.5 μunits PNGase F (Sigma). After 1 hour and 20 minutes of incubation at 37° C., the reactions were terminated by incubation at 95° C. for 5 minutes and an aliquot from each reaction was resolved with SDS-PAGE. The electrophoresis showed that 44.3 kD glycosylated form of ovalbumin was transformed into a deglycosylated 42.9 kD form in both reactions. The analyses indicate that compound 3266 is equivalent to the deglycosylation enhancement found using SDS, while eliminating the deleterious effects of SDS in concomitant spectrometric and chromatographic analysis.

Example 12. Cleavable Surfactants

The following are surfactant compounds of the invention, useful for the methods described herein.

FIGS. 11A-18B show HPLC chromatograms resulting from a control digest (RapiGest™ surfactant) and a surfactant compound of the invention, as noted below. In each set of chromatograms of FIGS. 11A-18B, the top chromatogram is the control and the bottom chromatogram is the test using a compound of the invention.

Experimental Conditions: Myoglobin/Trypsin Digest:

Myoglobin from horse heart (typically 25 μg) was digested with trypsin (Promega) at a 50:1 ratio in a volume of 125 μL (typical) of 50 mM Ammonium bicarbonate for 20 minutes at 37° C. with 0.01% RapiGest™ surfactant or 0.01% of the indicated compound of the invention (upper and lower chromatograms, respectively). TFA was added to 0.5-2% and the mixtures were incubated at 37° C. or 65° C. for 20 or 30 minutes. Degraded surfactant was removed by centrifugation at 14,000×g for 5 minutes. HPLC analysis was performed on a 25-50 µL reaction sample using an HP1050 LC system with an Agilent Sorbax SB-C18 column (3.0×100 mm, 3.5 micron) and a gradient of 0.1% TFA (97.5% initial) and Acetonitrile, 0.01% TFA (55% final condition followed by a 100% wash step) and a flow rate of 0.75 mL/min. Peptides were detected at 214 and 280 nm.

Experimental Conditions: Bacteriorhodopsin/Chymotrypsin Digest for Compounds 3116-3210, 3213-3223 and 3225-3275:

Bacteriorhodopsin (25 µg) was heated with 0.025% Rapigest™ surfactant or the indicated compound of the invention for 5 minutes at 95° C., then digested with chymotrypsin (Sigma) at a 10:1 ratio in 125 µL 50 mM Ammonium bicarbonate for 1 hour at 37° C. After one hour TFA was added to 0.5-2% and the mixtures were incubated at 37° C. or 65° C. for 20 or 30 minutes. Degraded surfactant was removed by centrifugation at 14,000×g for 5 minutes. An aliquot of 50-100 µL of digested protein was analyzed by HPLC as described above.

Experimental Conditions: Bacteriorhodopsin/Chymotrypsin Digest for Compounds 3211, 3212 and 3224:

Rapigest™ surfactant (control) reaction: As described above.

Figure 13A:
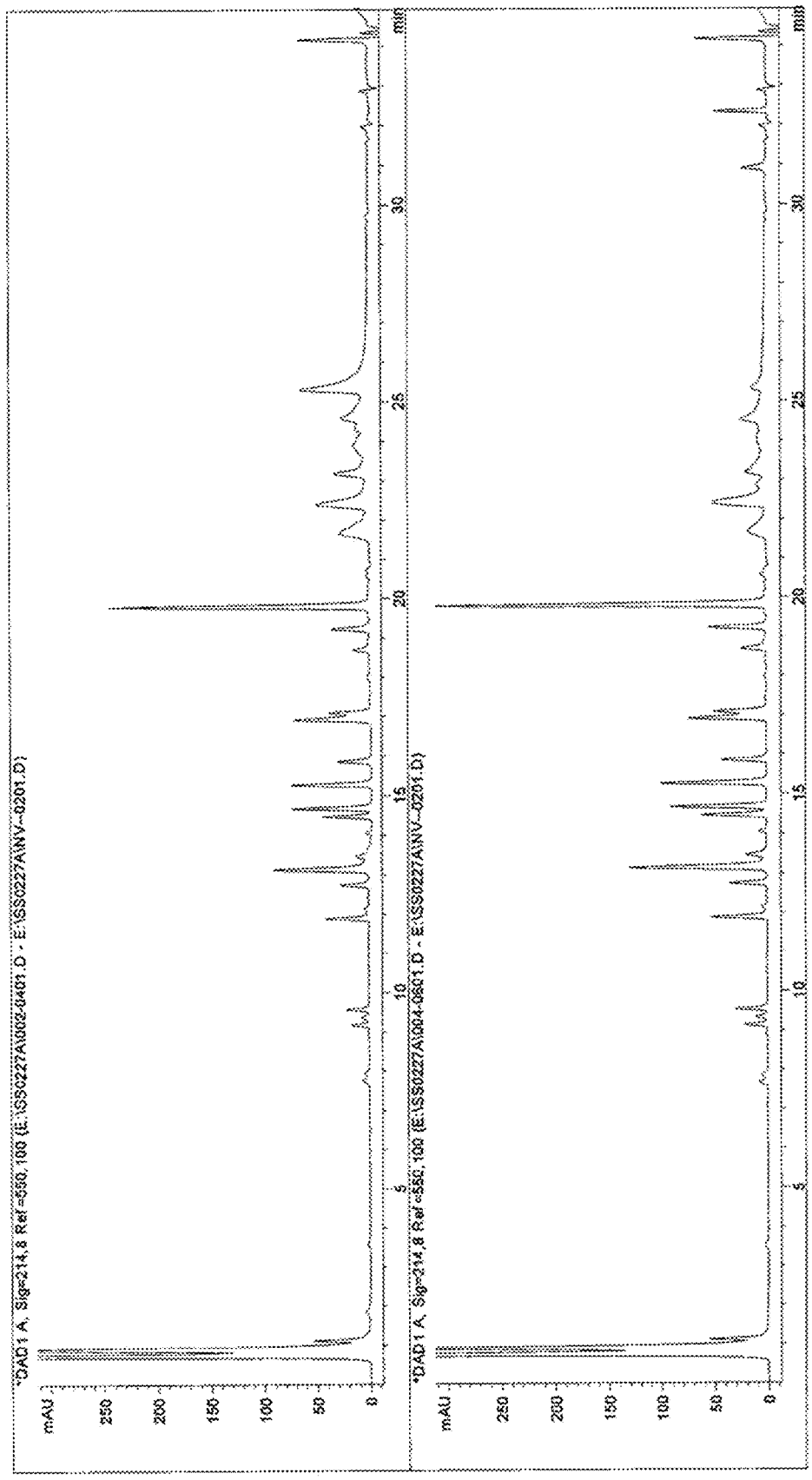
FIG. 13A illustrates the comparative effect of compound 3211 to aid in the digestion of Myoglobin with Trypsin as compared with the commercially available surfactant RapiGest™.
Figure 13B:
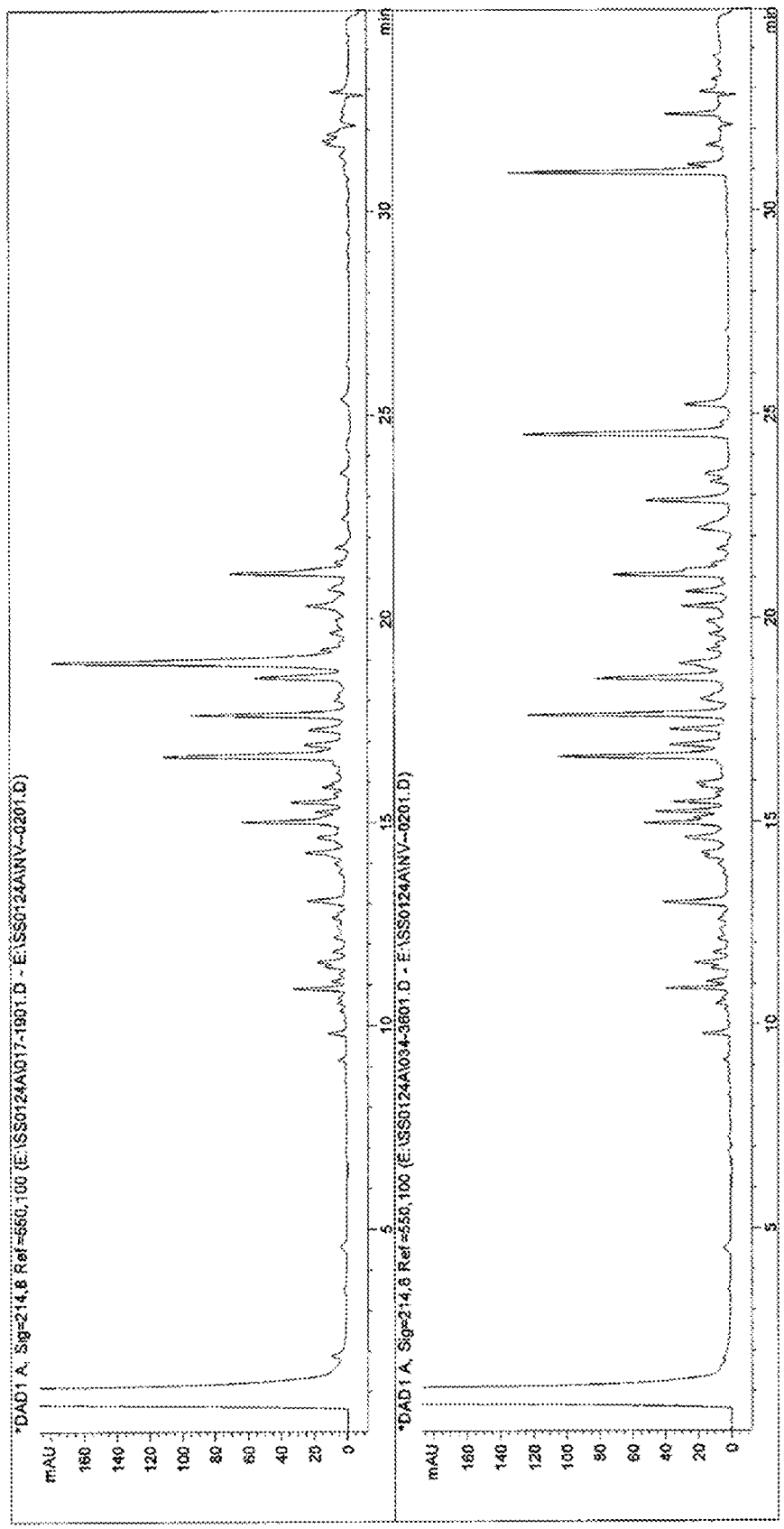
FIG. 13B illustrates the comparative effect of compound 3211 to aid in the solubilization and digestion of Bacteriorhodopsin with Chymotrypsin as compared with the commercially available surfactant RapiGest™, where Bacteriorhodopsin was solubilized with RapiGest™ surfactant at 95° C. while solubilization with compound 3211 was accomplished at room temperature (approximately 23° C.). In contrast.
Figure 13C:
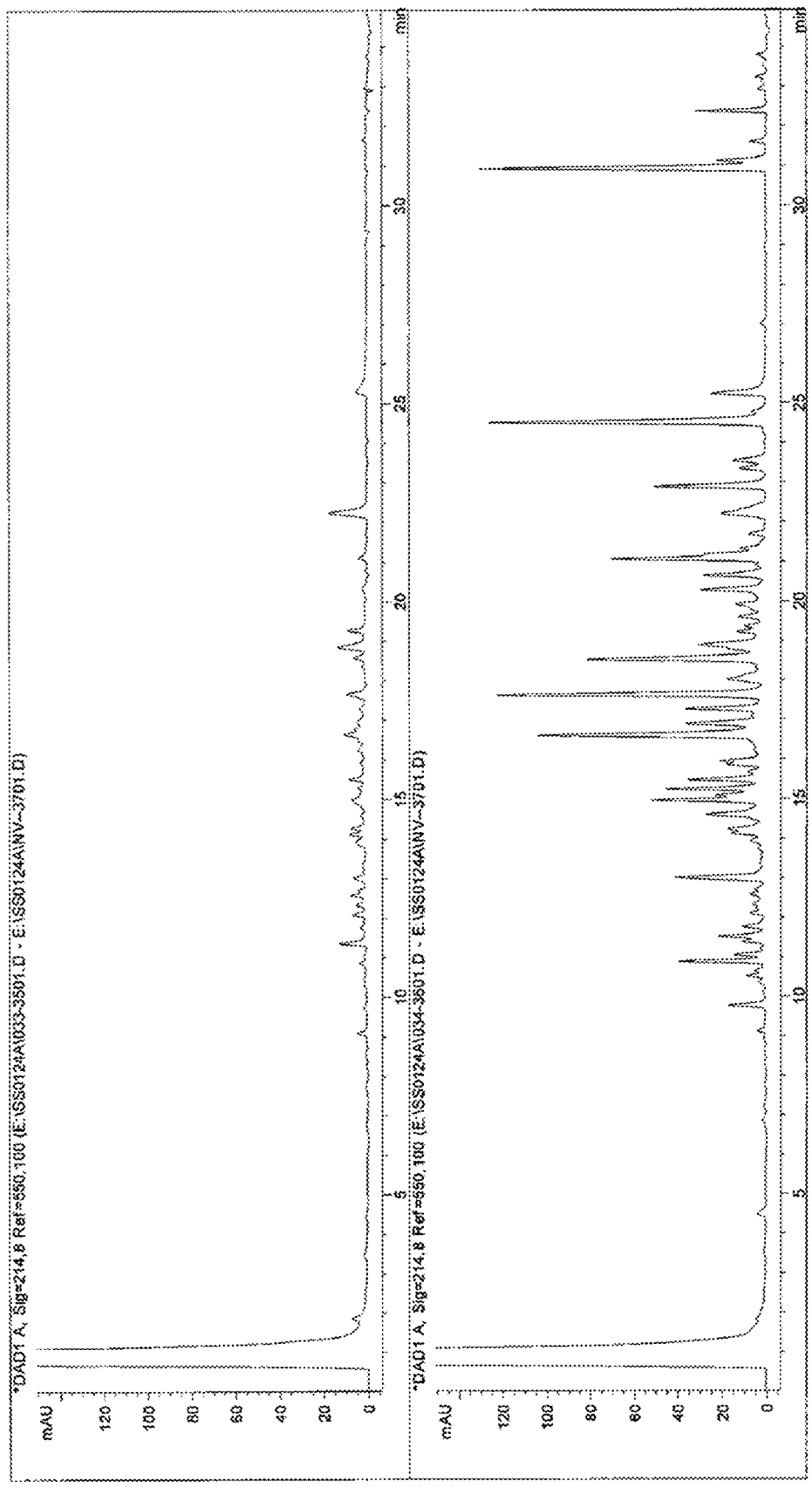
FIG. 13C illustrates the comparative effect of compound 3211 to aid in the solubilization and digestion of Bacteriorhodopsin with Chymotrypsin as compared with the commercially available surfactant RapiGest™, where solubilization was performed at room temperature for both RapiGest™ surfactant and compound 3211.
Figure 14A:
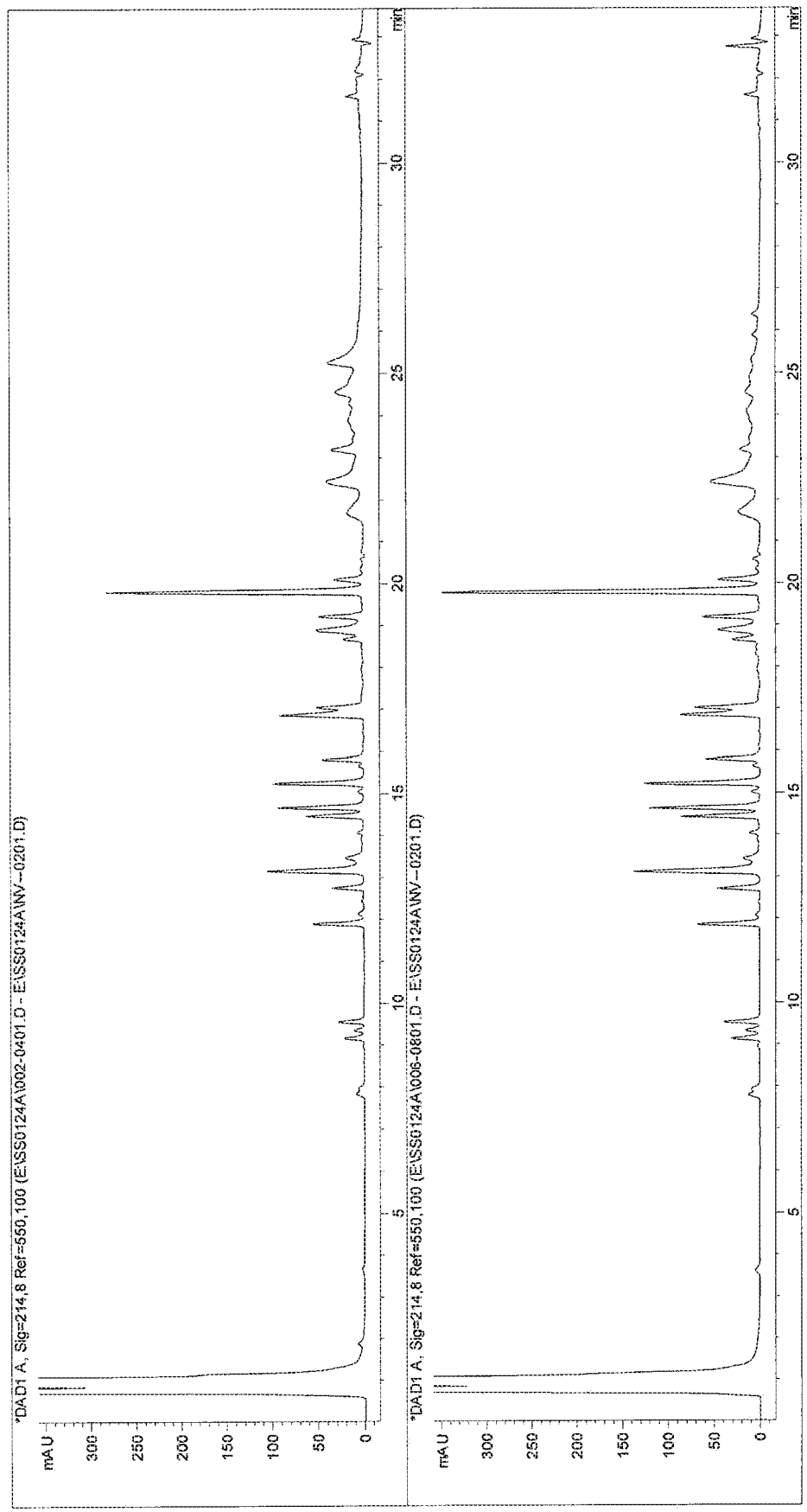
FIG. 14A illustrates the comparative effect of compound 3212 to aid in the digestion of Myoglobin with Trypsin as compared with the commercially available surfactant RapiGest™.
Figure 14B:
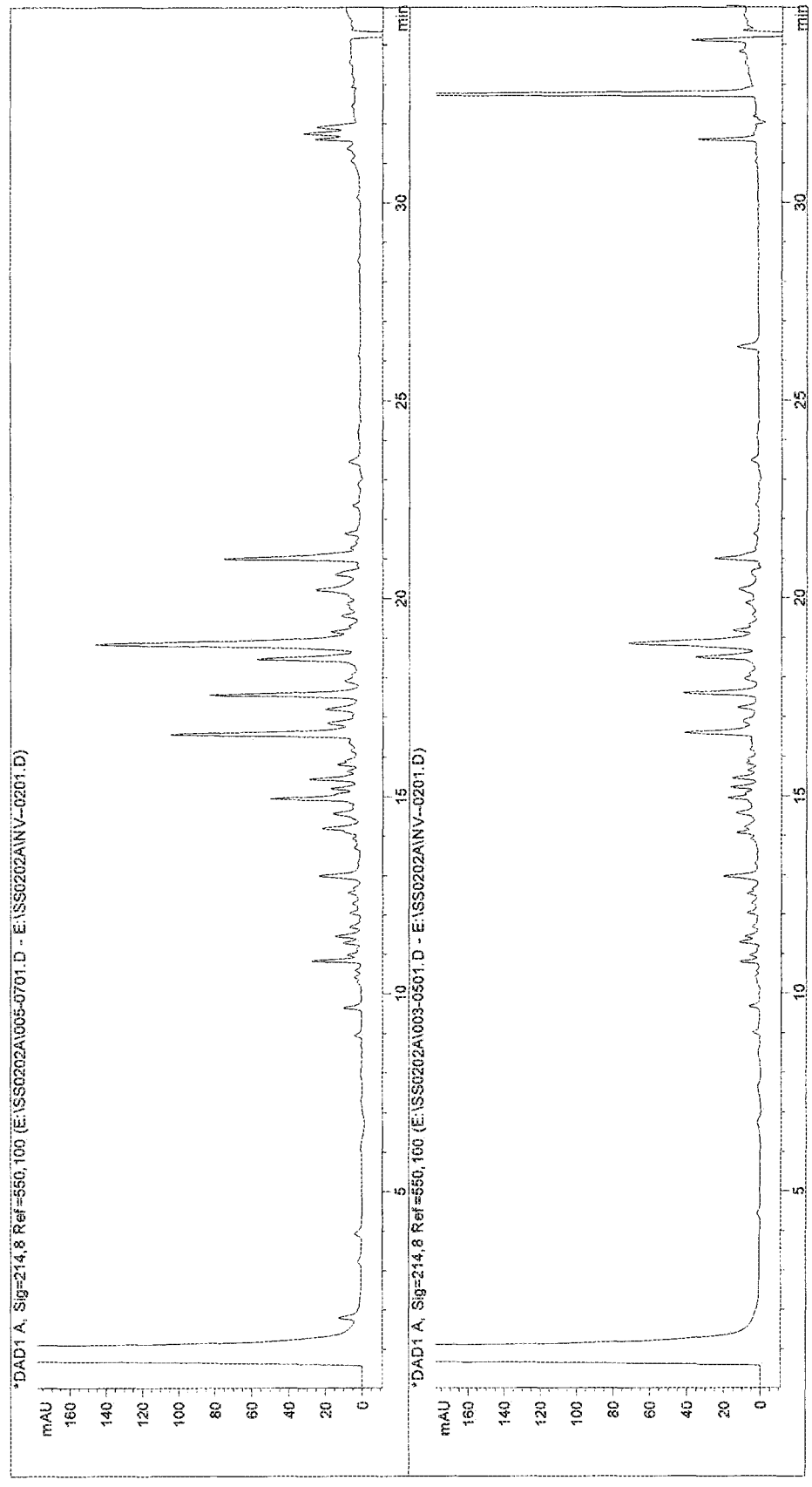
FIG. 14B illustrates the comparative effect of compound 3212 to aid in the solubilization and digestion of Bacteriorhodopsin with Chymotrypsin as compared with the commercially available surfactant RapiGest™. In both FIG. 14A and FIG. 14B, the upper chromatogram is the RapiGest™ surfactant assisted digestion reaction (control) and the lower chromatogram is the result obtained with compound 3212. Typical reaction and HPLC conditions are described in Example 12.
Figure 15A:
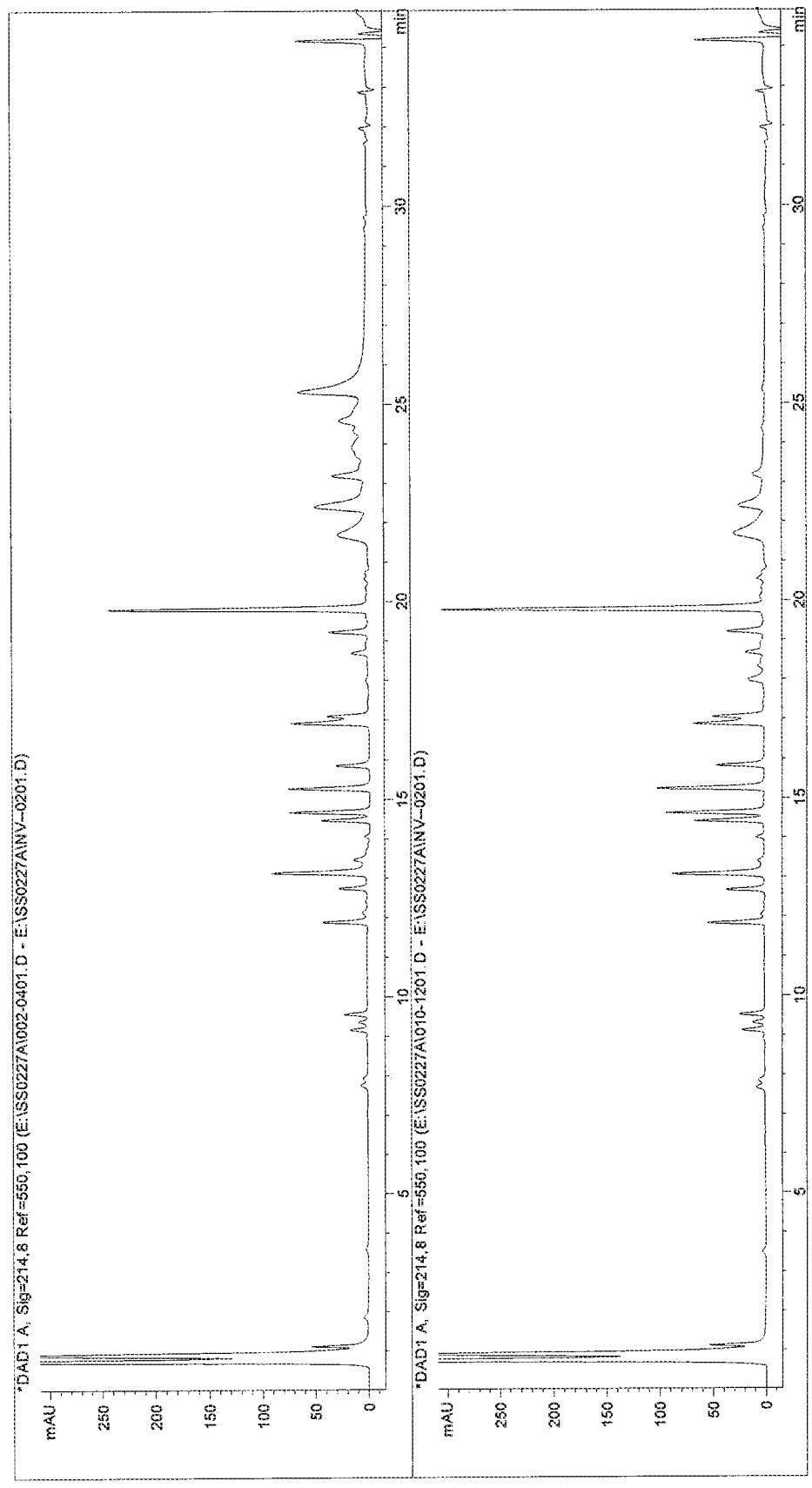
FIG. 15A illustrates the comparative effect of compound 3224 to aid in the digestion of Myoglobin with Trypsin as compared with the commercially available surfactant RapiGest™.
Figure 15B:
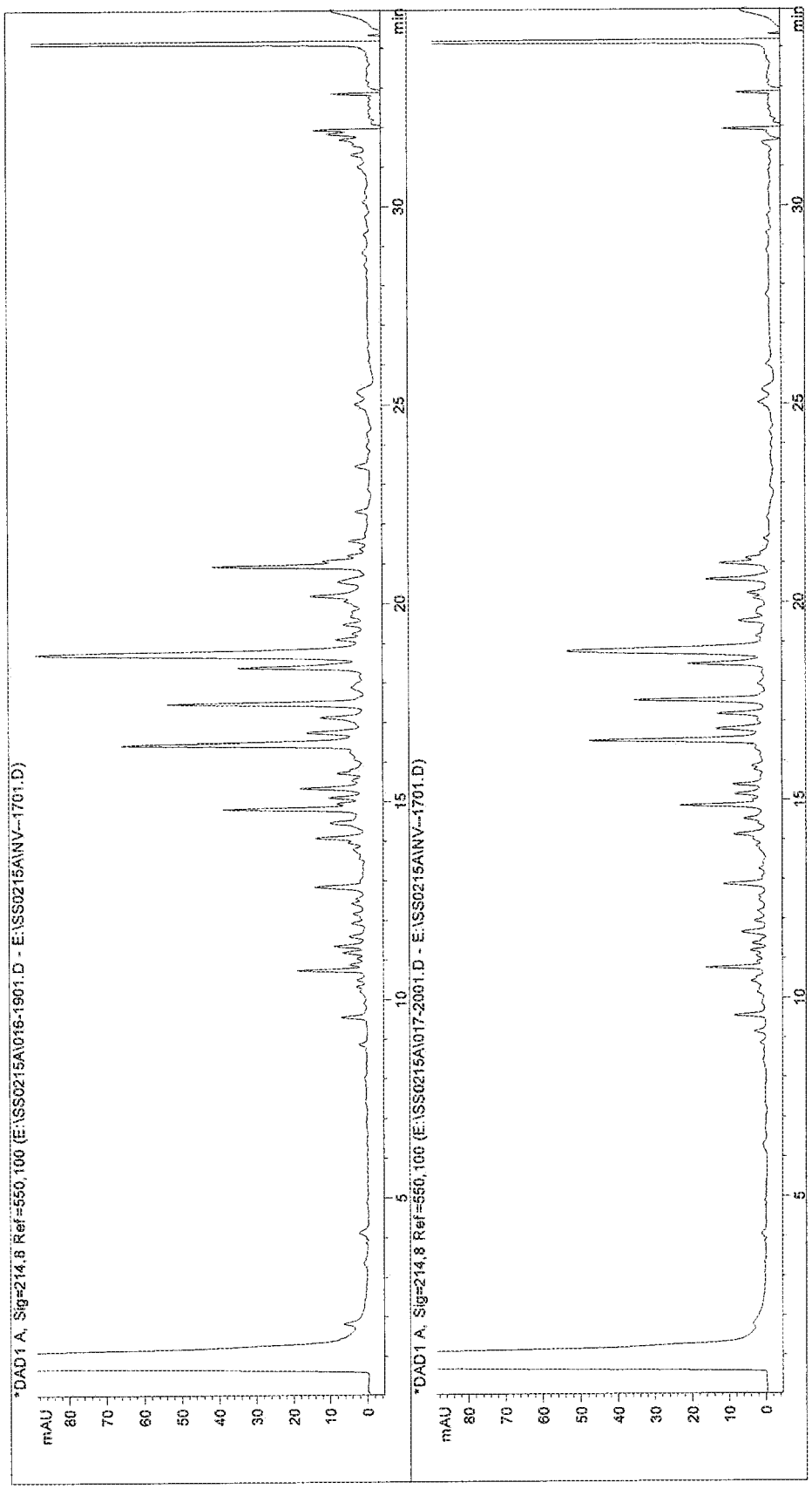
FIG. 15B illustrates the comparative effect of compound 3224 to aid in the solubilization and digestion of Bacteriorhodopsin with Chymotrypsin as compared with the commercially available surfactant RapiGest™. In both FIG. 15A and FIG. 15B, the upper chromatogram is the RapiGest™ surfactant assisted digestion reaction (control) and the lower chromatogram is the result obtained with compound 3224. Typical reaction and HPLC conditions are described in Example 12.
Figure 16A:
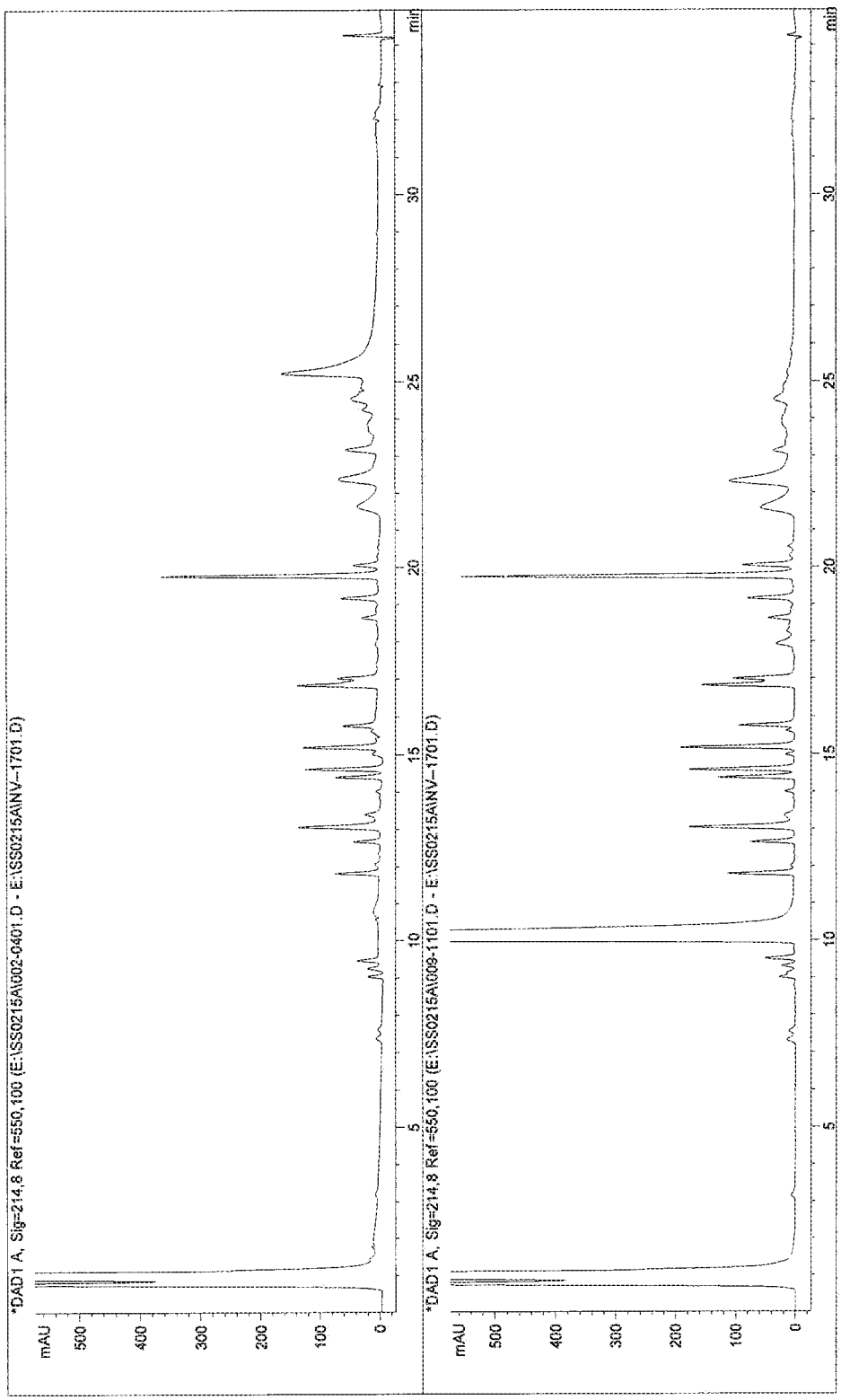
FIG. 16A illustrates the comparative effect of compound 3228 to aid in the digestion of Myoglobin with Trypsin as compared with the commercially available surfactant RapiGest™.
Figure 16B:
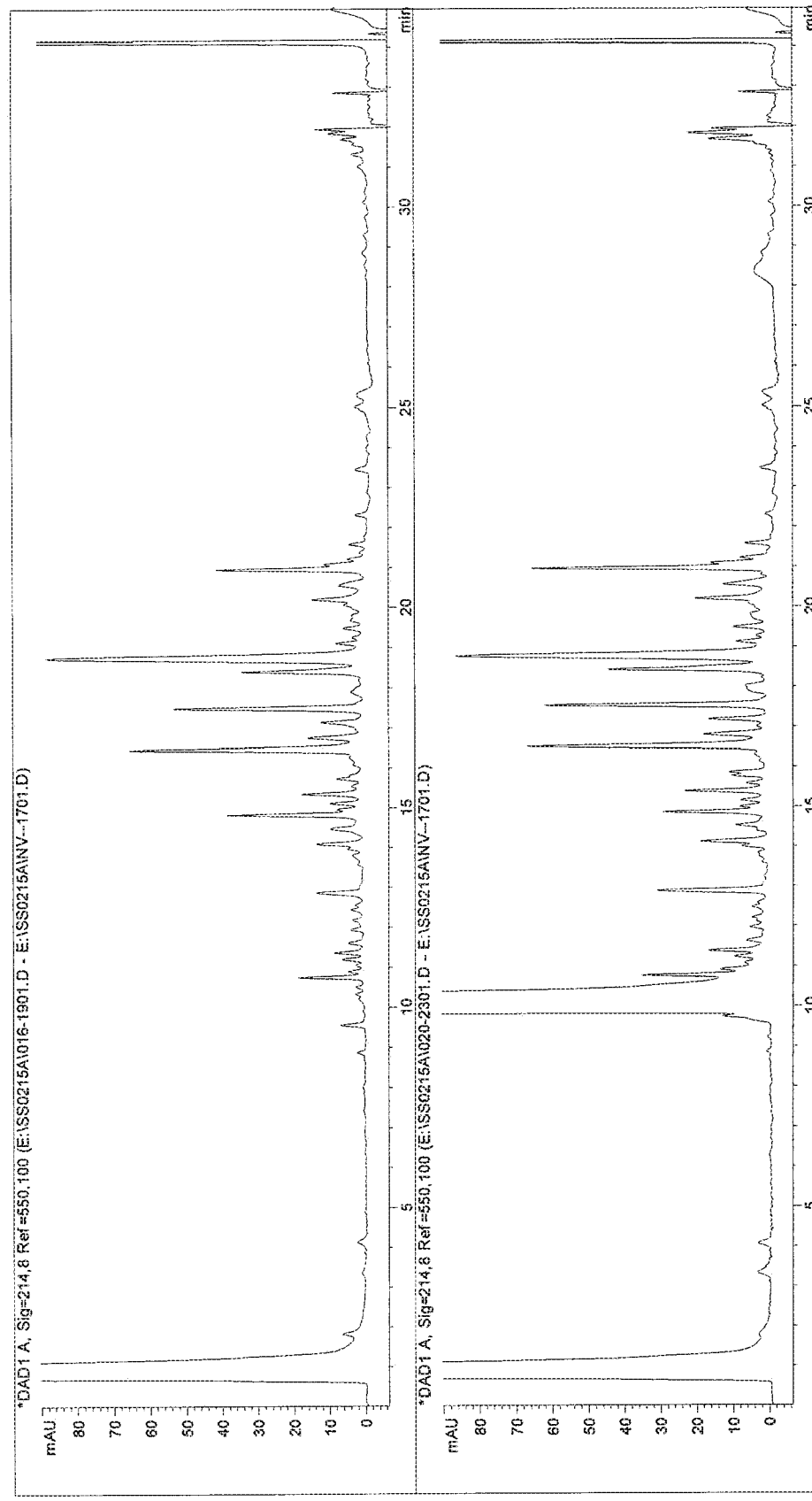
FIG. 16B illustrates the comparative effect of compound 3228 to aid in the solubilization and digestion of Bacteriorhodopsin with Chymotrypsin as compared with the commercially available surfactant RapiGest™. In both FIG. 16A and FIG. 16B, the upper chromatogram is the RapiGest™ surfactant assisted digestion reaction (control) and the lower chromatogram is the result obtained with compound 3228. Typical reaction and HPLC conditions are described in Example 12.
Figure 17A:
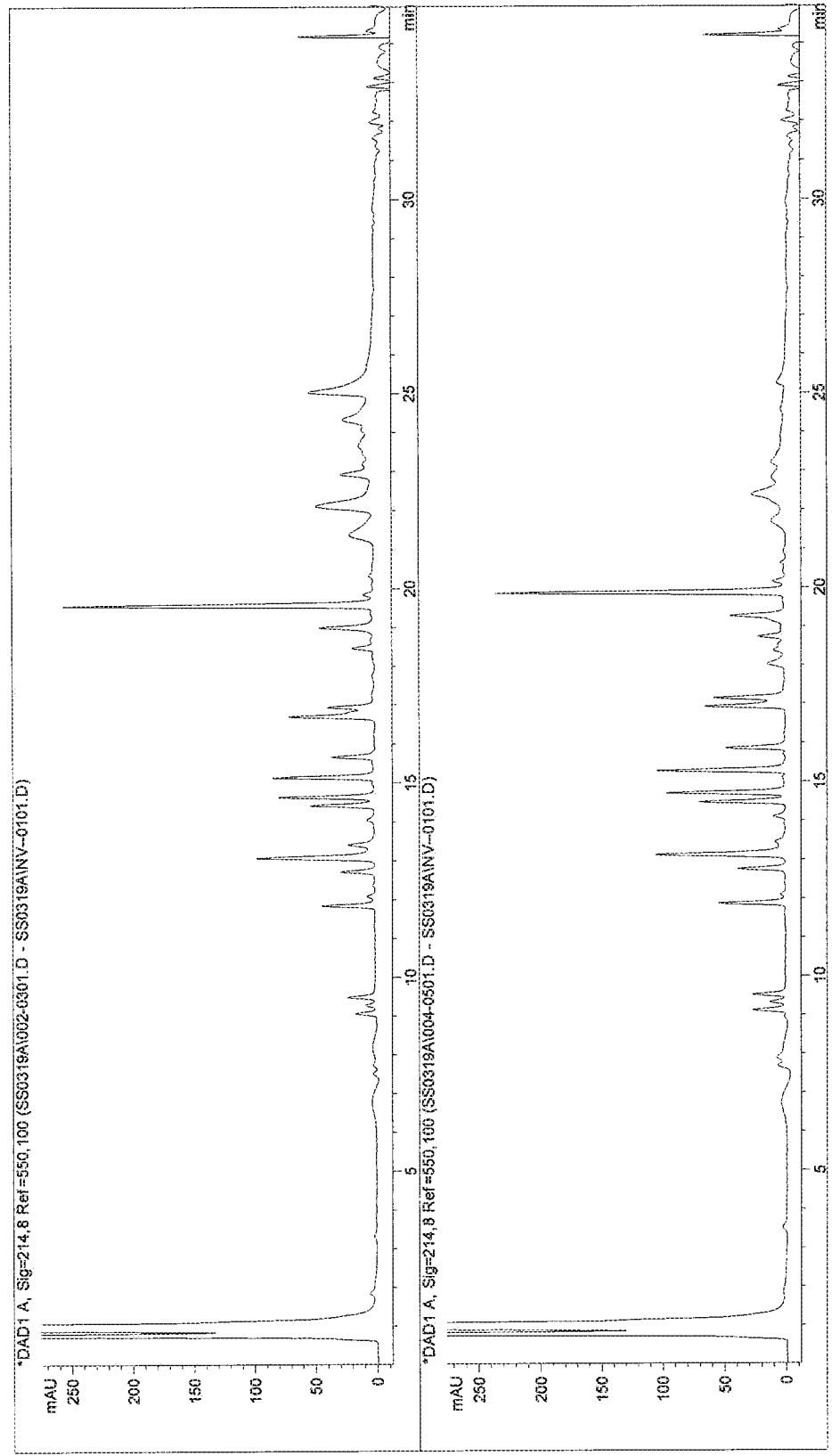
FIG. 17A illustrates the comparative effect of compound 3266 to aid in the digestion of Myoglobin with Trypsin as compared with the commercially available surfactant RapiGest™.
Figure 18A:
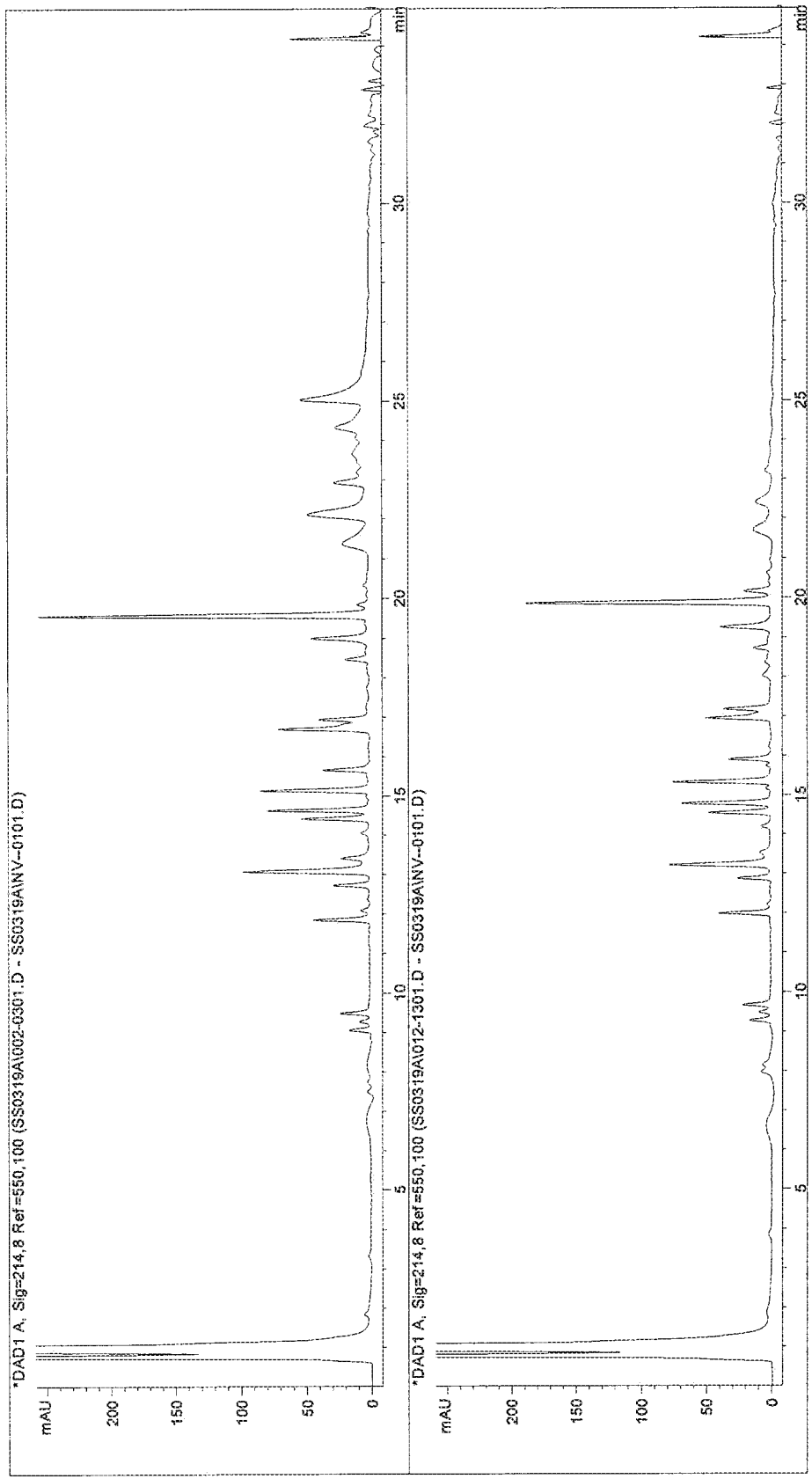
FIG. 18A illustrates the comparative effect of compound 3271 to aid in the digestion of Myoglobin with Trypsin as compared with the commercially available surfactant RapiGest™.
Figure 18B:
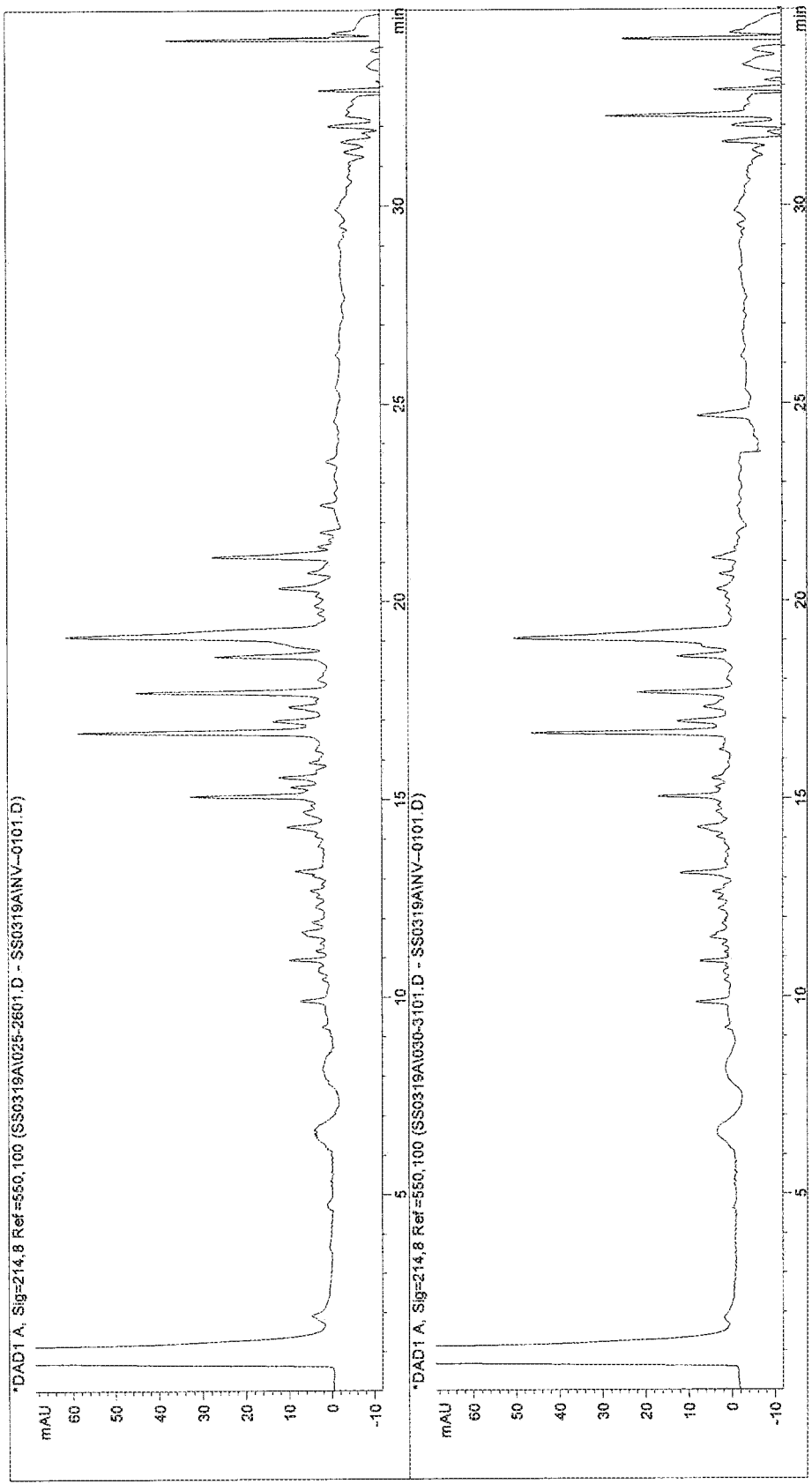
FIG. 18B illustrates the comparative effect of compound 3271 to aid in the solubilization and digestion of Bacteriorhodopsin with Chymotrypsin as compared with the commercially available surfactant RapiGest™. In both FIG. 18A and FIG. 18B, the upper chromatogram is the RapiGest™ surfactant assisted digestion reaction (control) and the lower chromatogram is the result obtained with compound 3271. Typical reaction and HPLC conditions are described in Example 12.

Compound 3211, 3212, 3224 and Rapigest™ surfactant control for FIG. 13C reactions: Bacteriorhodopsin (25 µg) was solubilized with 0.025% compound of interest for 1-2 minutes at room temperature, then digested with chymotrypsin (Sigma) at a 10:1 ratio in 125 µL 50 mM Ammonium bicarbonate for 1 hour at 37° C. After one hour TFA was added to 0.5-2% and the mixtures were incubated at 37° C. or 65° C. for 20 or 30 minutes. Degraded surfactant was removed by centrifugation at 14,000×g for 5 minutes. An aliquot of 50-100 µL of digested protein was analyzed by HPLC as described above.

For each compound numbered below in Example 12, the rate of enhanced digestion was determined from the ratio of the surfactant peak area (surfactant #Pk. Area) to the Rapigest™ surfactant peak area (RG Pk area). Peak area was determined as the sum of all peaks integrated from 8-22 minutes. A ratio greater than one indicates more digestion was observed for the surfactant reaction than the Rapigest™ surfactant control reaction.

Compound 3116

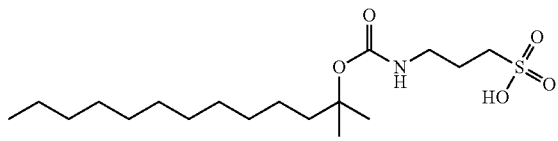

Myoglobin/Trypsin digest: 3116 Pk area/RG Pk area=0.6.
Bacteriorhodopsin/Chymotrypsin digest: 3116 Pk area/RG Pk area=1.5.

Compound 3116 has an acceptable solubility in aqueous solutions: 0.5% or more and showed acid-lability: 0.01% 3116 was degraded within 2 hours at 37° C. See FIG. 11A and FIG. 11B.

Compound 3186

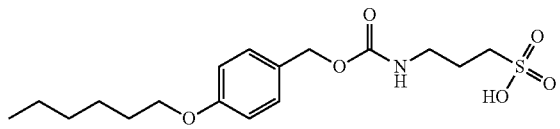

Myoglobin/Trypsin digest: 3186 Pk area/RG Pk area=N.D.
Bacteriorhodopsin/Chymotrypsin digest: BR was boiled with 3186 for 5 minutes before adding chymotrypsin; 3186 Pk area/RG Pk area=0.45.

Compound 3186 shows some solubility in aqueous solution and degradation of a 0.01% solution was complete within 30 minutes at 37° C.

Compound 3189

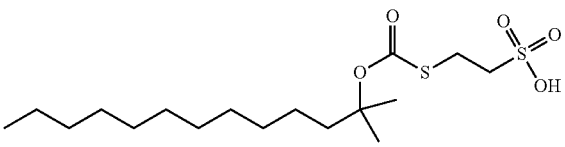

Myoglobin/Trypsin digest: 3189 Pk area/RG Pk area=1.1
Bacteriorhodopsin/Chymotrypsin digest: BR was boiled with 3189 before adding chymotrypsin; 3189 Pk area/RG Pk area=0.6.

Compound 3189 has a good solubility in aqueous solution; it was easily dissolved to 0.5%. Acid-lability was poor: 0.01% 3189 degraded only after overnight incubation at 37° C.

Compound 3190

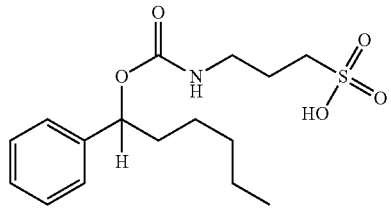

Myoglobin/Trypsin digest: 3190 Pk area/RG Pk area=N.D.
Bacteriorhodopsin/Chymotrypsin digest: BR was boiled with 3190 before adding chymotrypsin; 3190Pk area/RG Pk area=0.34.

Compound 3190 has a good solubility in aqueous solutions (easily dissolved to 0.5%). Moderate degradation rate: 30 minutes for 0.01% solution, overnight—for 0.1% solution.

Compound: 3192

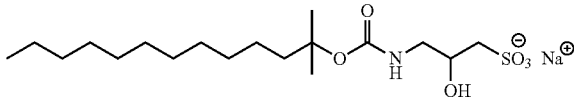

Myoglobin/Trypsin digest: 3192 Pk area/RG Pk area=1.3
Bacteriorhodopsin/Chymotrypsin digest: BR was boiled with 3192 before adding chymotrypsin; 3192 Pk area/RG Pk area=1.1.

Compound 3192 has a good solubility in aqueous solutions (easily dissolved to 0.5%). Degradation rate was very low: 0.01% solution degraded only after overnight incubation.

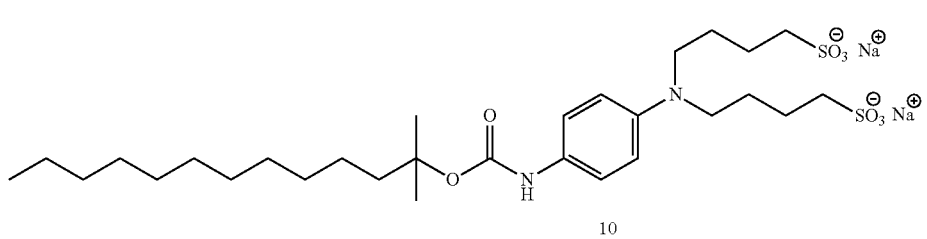
Compound: 3194

Myoglobin/Trypsin digest: 3194 Pk area/RG Pk area=0.72
Bacteriorhodopsin/Chymotrypsin digest: BR was boiled with 3194 before adding chymotrypsin; 3194 Pk area/RG Pk area=1.1.
Good solubility in aqueous solutions (easily dissolved to 0.5%). No degradation was observed even after overnight incubation.

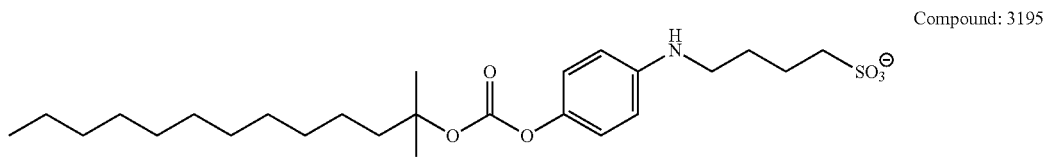
Compound: 3195

Myoglobin/Trypsin digest: 3195 Pk area/RG Pk area=0.5
Bacteriorhodopsin/Chymotrypsin digest: BR was boiled with 3195 before adding chymotrypsin; 3195 Pk area/RG Pk area=N.D.
Moderate solubility in aqueous solutions: not more than 0.2%. No degradation was observed even after overnight incubation.

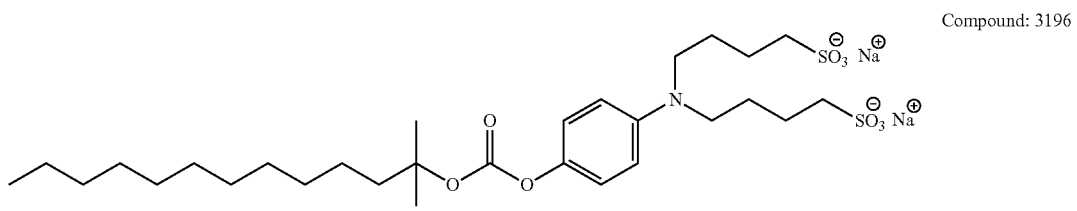
Compound: 3196

Myoglobin/Trypsin digest: 3196 Pk area/RG Pk area=0.65
Bacteriorhodopsin/Chymotrypsin digest: BR was boiled with 3196 before adding chymotrypsin; 3196 Pk area/RG Pk area=N.D.
Good solubility in aqueous solutions: easily dissolved to 0.5%. Moderate degradation rate: 30 minutes for 0.01% solution, overnight—for 0.1% solution.

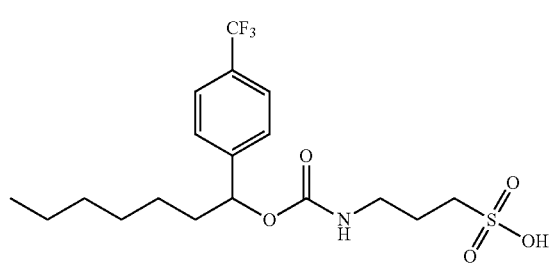
Compound: 3199

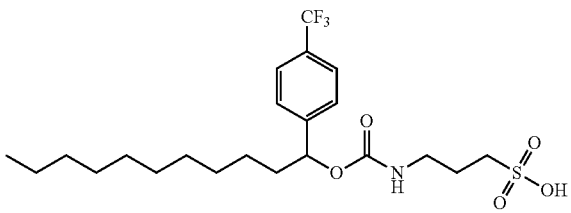
Compound: 3200

Myoglobin/Trypsin digest: 3199 Pk area/RG Pk area=0.37
Bacteriorhodopsin/Chymotrypsin digest: BR was boiled with 3199 before adding chymotrypsin; 3199 Pk area/RG Pk area=N.D.
Good solubility in aqueous solutions: easily dissolved to 0.5%. No degradation was observed even after overnight incubation.

Myoglobin/Trypsin digest: 3200 Pk area/RG Pk area=0.7
Bacteriorhodopsin/Chymotrypsin digest: BR was boiled with 3200 before adding chymotrypsin; 3200 Pk area/RG Pk area=0.8.

Low solubility in aqueous solutions: ~0.01%. No degradation was observed even after overnight incubation.

Compound: 3201

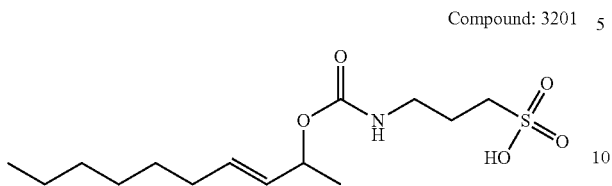

Myoglobin/Trypsin digest: 3201 Pk area/RG Pk area=0.3
Bacteriorhodopsin/Chymotrypsin digest: BR was boiled with 3201 before adding chymotrypsin; 3201 Pk area/RG Pk area=0.4.
Good solubility in aqueous solutions: easily dissolved to 0.5%.

Compound 3202

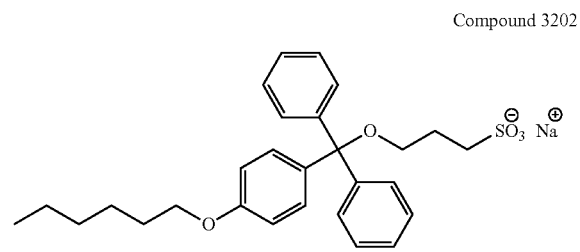

Myoglobin/Trypsin digest: 3202 Pk area/RG Pk area=1.1.
Bacteriorhodopsin/Chymotrypsin digest: BR was boiled with 3202 before adding chymotrypsin; 3202 Pk area/RG Pk area=0.6.
Somewhat low solubility: ~0.01%. Degradation rate was variable because of lower surfactant solubility: 0.01% 3202 degraded within 30 minutes. See FIG. 12A and FIG. 12B.

Compound: 3203

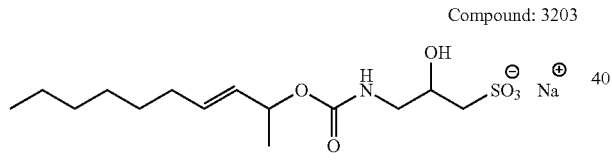

Myoglobin/Trypsin digest: 3203 Pk area/RG Pk area=N.D.
Bacteriorhodopsin/Chymotrypsin digest: BR was boiled with 3203 before adding chymotrypsin; 3203 Pk area/RG Pk area=0.4.
Good solubility: easily dissolved to 0.5%. Degradation rate is moderate: 0.1% 3203 was degraded after overnight incubation.

Compound: 3204

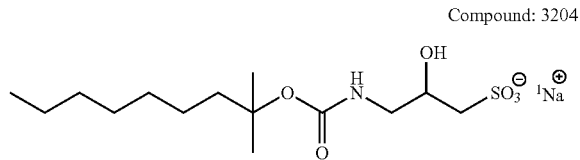

Myoglobin/Trypsin digest: 3204 Pk area/RG Pk area=0.87.
Bacteriorhodopsin/Chymotrypsin digest: BR was boiled with 3204 before adding chymotrypsin; 3204 Pk area/RG Pk area=0.55.
Good solubility: easily dissolved to 0.5%. Degradation rate is moderate: 0.1% 3203 was degraded after overnight incubation.

Compound: 3205

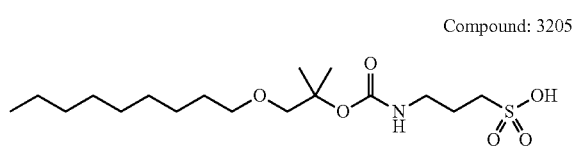 [SMILES: CCCCCCCCCOCC(C)(C)OC(=O)NCCCS(=O)(=O)O]

Myoglobin/Trypsin digest: 3205 Pk area/RG Pk area=0.3.
Bacteriorhodopsin/Chymotrypsin digest: BR was boiled with 3205 before adding chymotrypsin; 3205 Pk area/RG Pk area=0.45.
Good solubility: easily dissolved to 0.5%. No degradation was observed even after overnight incubation.

Compound: 3206

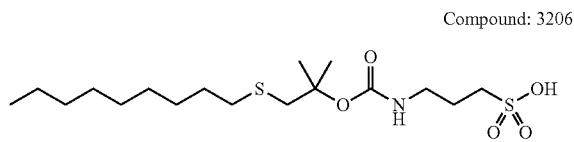 [SMILES: CCCCCCCCCSCC(C)(C)OC(=O)NCCCS(=O)(=O)O]

Myoglobin/Trypsin digest: 3206 Pk area/RG Pk area=0.26.
Bacteriorhodopsin/Chymotrypsin digest: BR was boiled with 3206 before adding chymotrypsin; 3206 Pk area/RG Pk area=0.8.
Good solubility: easily dissolved to 0.5%. Degradation rate is moderate: 0.1% 3203 was degraded after overnight incubation.

Compound: 3207

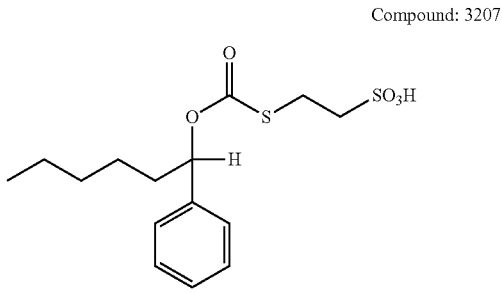 [SMILES: CCCCCC(OC(=O)SCCS(=O)(=O)O)c1ccccc1]

Myoglobin/Trypsin digest: 3207 Pk area/RG Pk area=N.D.
Bacteriorhodopsin/Chymotrypsin digest: BR was boiled with 3207 before adding chymotrypsin; 3207 Pk area/RG Pk area=N.D.
Good solubility: easily dissolved to 0.5%. Degradation rate is low: 0.01% 3207 degraded within 1 hour).

Compound: 3209

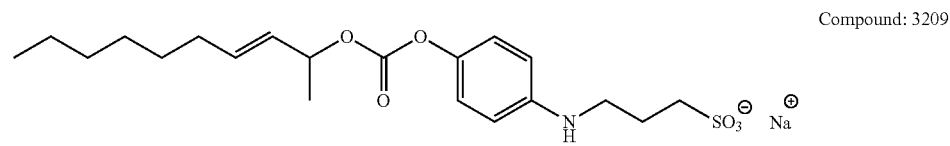

Myoglobin/Trypsin digest: 3209 Pk area/RG Pk area=2.1.
Bacteriorhodopsin/Chymotrypsin digest: BR was boiled with 3209 before adding chymotrypsin; 3209 Pk area/RG Pk area=N.D.

Good solubility: easily dissolved to 0.5%. No degradation was observed even after overnight incubation.

Compound: 3210

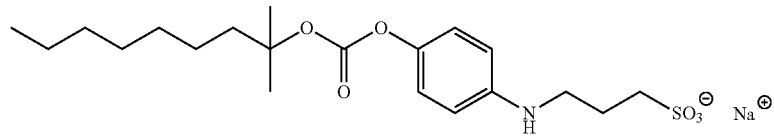

Myoglobin/Trypsin digest: 3210 Pk area/RG Pk area=0.3.
Bacteriorhodopsin/Chymotrypsin digest: BR was boiled with 3210 before adding chymotrypsin; 3210 Pk area/RG Pk area=N.D.

Good solubility: easily dissolved to 0.5%. Degradation rate is moderate: 0.1% 3203 was degraded after overnight incubation.

Compound: 3211

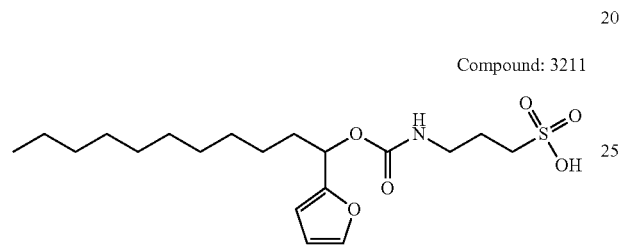

Myoglobin/Trypsin digest: 3211 Pk area/RG Pk area=1.3.
Bacteriorhodopsin/Chymotrypsin digest: BR was boiled with Rapigest™ surfactant but not with 3211 before adding chymotrypsin; 3211 Pk area/RG Pk area=0.9

Good solubility: easily dissolved to 1% in 50 mM ammonium bicarbonate. Excellent degradation rate: 15 minutes in 0.5% TFA at 37° C. or 5 minutes of boiling without TFA. Excellent solubilization properties: rapidly solubilized BR at room temperature. Compound 3211 degrades even at room temperature at a substantial rate.

Also see FIG. 13A, FIG. 13B and FIG. 13C.

| Hydrolytic stability in 50 mM Ammonium Bicarbonate | |
|---|---|
| Surfactant conc. | ½-life (hr) |
| 0.0025% | 0.5 |
| 0.025% | 1.1 |
| 0.025%/20% AcN | 6 |
| 0.025%/40% AcN | 52 |
| 0.025%/60% AcN | >100 |
| 0.025%/80% AcN | >> |
| 0.10% | 4.8 |
| 1% | 21 |
| 1%/50% AcN | >100 |

>> = compound 100% stable over course of experiment.

Hydrolytic stability was measured by monitoring the change in retention time of the intact surfactant by reverse-phase HPLC. The ½-life is defined as the time required to reach 50% degradation.

Compound: 3212

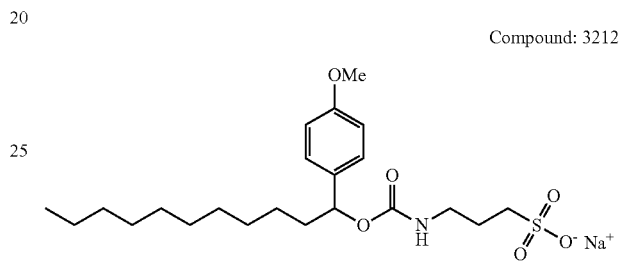

Myoglobin/Trypsin digest: 3212 Pk area/RG Pk area=1.4.

Bacteriorhodopsin/Chymotrypsin digest BR was boiled with Rapigest™ surfactant but not with 3212 before adding chymotrypsin; 3212 Pk area/RG Pk area=N.D.

Good solubility: easily dissolved to 1% in 50 mM ammonium bicarbonate. Excellent degradation rate: 15 minutes in 0.5% TFA at 37° C. or 5 minutes of boiling without TFA. Excellent solubilization properties: rapidly solubilized BR at room temperature. Also see FIG. 14A and FIG. 14B.

| Hydrolytic stability in 50 mM Ammonium Bicarbonate Surfactant conc. ½-life (hr) | |
|---|---|
| 0.0025% | 3.7 |
| 0.025% | 21 |
| 0.10% | 38 |
| 1% | >> |

>> = compound 100% stable over course of experiment.

Compound: 3213

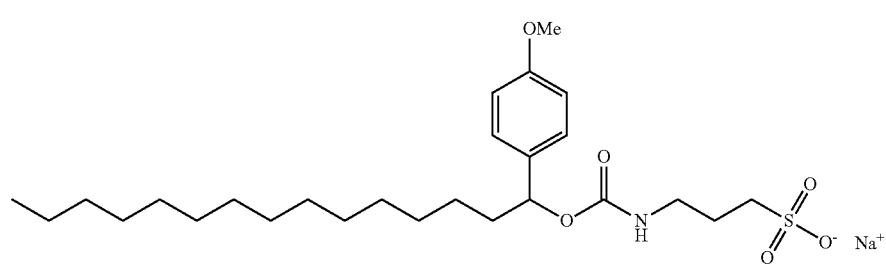

Myoglobin/Trypsin digest: 3213 Pk area/RG Pk area=0.8
Bacteriorhodopsin/Chymotrypsin digest: BR was boiled with 3213 before adding chymotrypsin; 3213 Pk area/RG Pk area=1.3

Moderate solubility: 0.025% after 10 minutes.

| Hydrolytic stability in 50 mM Ammonium Bicarbonate | |
|---|---|
| Surfactant conc. | ½-life (hr) |
| 0.0025% | 62 |
| 0.025% | 128 |

Compound: 3214

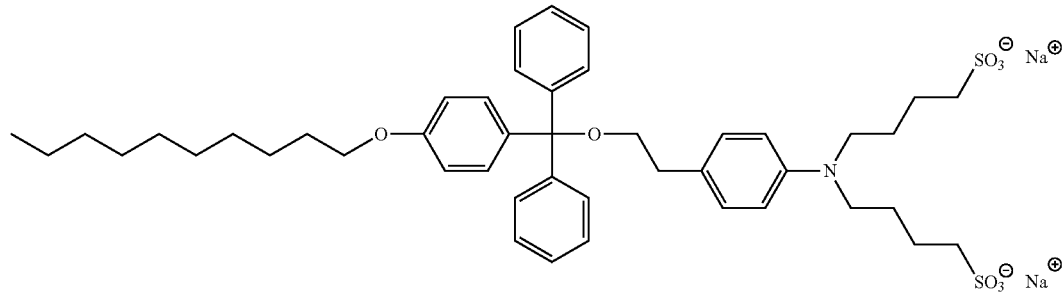

Myoglobin/Trypsin digest: 3214 Pk area/RG Pk area=N.D.
Bacteriorhodopsin/Chymotrypsin digest 10:1 ratio: at 0.1%; BR was boiled with 3214 before adding chymotrypsin; 3214 Pk area/RG Pk area=0.6

Good solubility in aqueous solutions: easily dissolved to 1%.

Compound: 3215

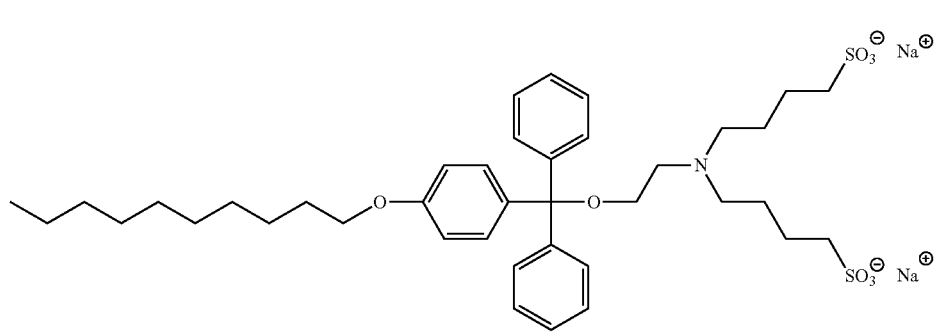

Myoglobin/Trypsin digest: 3215 Pk area/RG Pk area=0.56.
Bacteriorhodopsin/Chymotrypsin digest: BR was boiled with 3215 before adding chymotrypsin; 3215 Pk area/RG Pk area=1.2.

Good solubility in aqueous solutions: easily dissolved to 1%. Degradation rate: 0.1% solution degrades after 1 hour incubation in 0.5% TFA. Analysis of compound 3215 indicated moderate thermolability.

Compound: 3216

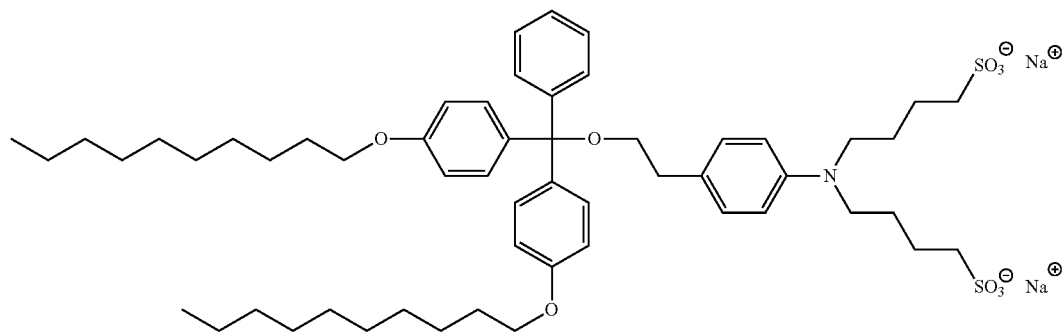

Myoglobin/Trypsin digest: 3216 area/RG Pk area=N.D.
Bacteriorhodopsin/Chymotrypsin digest: BR was boiled with 3216 before adding chymotrypsin; 3216 Pk area/RG Pk area=0.7.
  Insoluble in aqueous solutions. Solubilized to 10% in 100% DMSO.

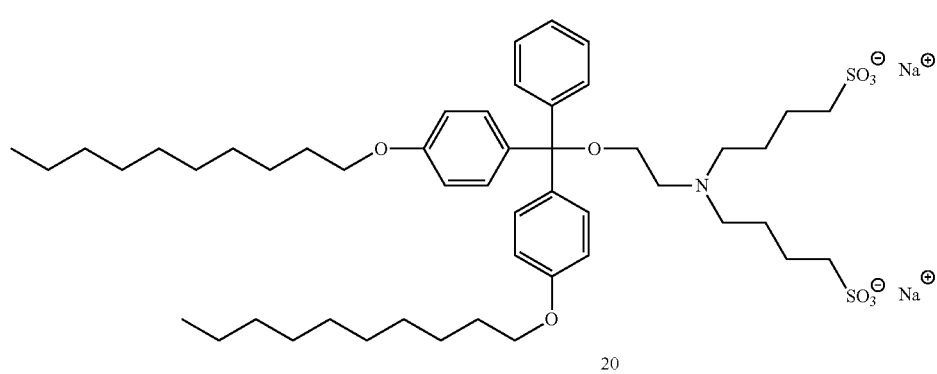

Compound: 3218

Myoglobin/Trypsin digest: 3218 Pk area/RG Pk area=0.3.
Bacteriorhodopsin/Chymotrypsin digest: BR was boiled with 3218 before adding chymotrypsin; 3218 Pk area/RG Pk area=0.65.
  Insoluble in aqueous solutions. Solubilized to 10% in DMSO.

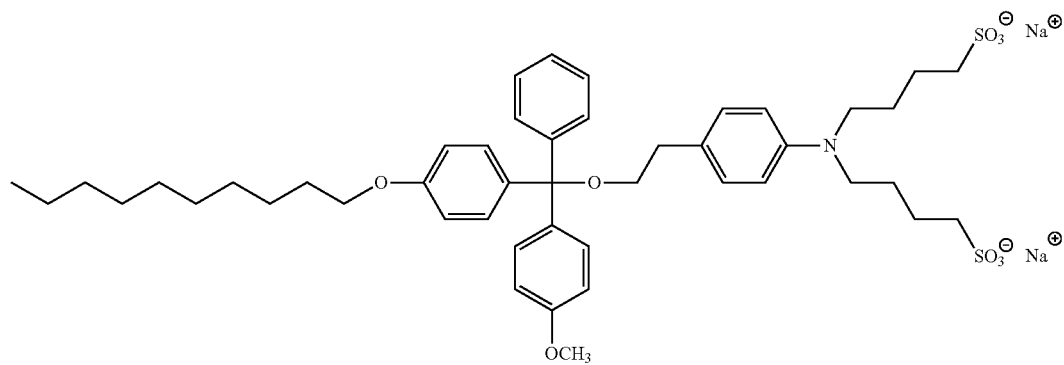

Compound: 3219

Myoglobin/Trypsin digest: 3219 Pk area/RG Pk area=N.D.
Bacteriorhodopsin/Chymotrypsin digest: BR was boiled with 3219 before adding chymotrypsin; 3219 Pk area/RG Pk area=N.D.
  Good solubility in aqueous solutions: easily dissolved to 1%.

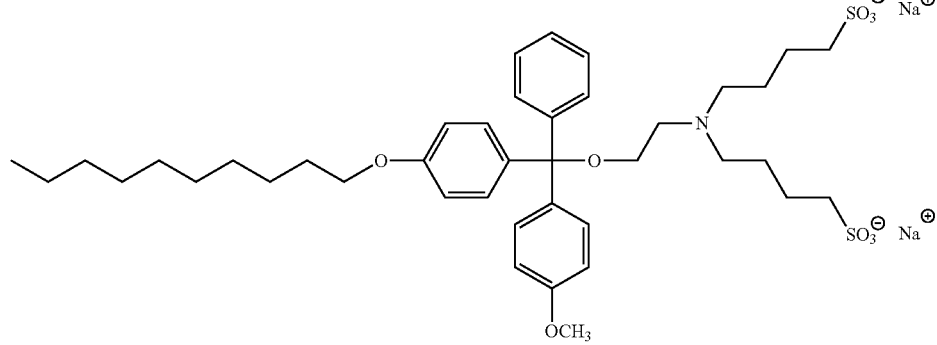

Compound: 3220

Myoglobin/Trypsin digest: 3220 Pk area/RG Pk area=0.2. Bacteriorhodopsin/Chymotrypsin digest 10:1 ratio: at 0.025%; BR was boiled with 3220 before adding chymotrypsin; 3220 Pk area/RG Pk area=0.8.

Good solubility in aqueous solutions: easily dissolved to 1%. Excellent degradation rate: 0.1% 3220 degraded within 15 minutes in 0.5% TFA at 37° C. The surfactant had moderate thermolability.

| Hydrolytic stability in 50 mM Ammonium Bicarbonate | |
|---|---|
| Surfactant conc. | ½-life (hr) |
| 0.0025% | 1.3 |
| 0.025% | 8.3 |

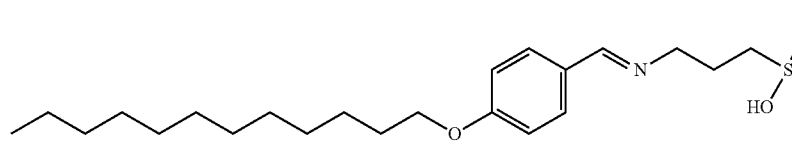

Compound 3221

Myoglobin/Trypsin digest: 3221 Pk area/RG Pk area=0.13.

Bacteriorhodopsin/Chymotrypsin digest: BR was boiled with 3221 before adding chymotrypsin; 3221 Pk area/RG Pk area=0.5.

Good solubility in aqueous solutions: easily dissolved to 0.5%.

-continued

| Hydrolytic stability in 50 mM Ammonium Bicarbonate | |
|---|---|
| Surfactant conc. | ½-life (hr) |
| 0.10% | 23 |
| 0.25% | 22 |

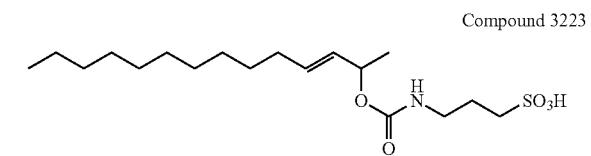 [SMILES: CCCCCCCCCC/C=C/C(C)OC(=O)NCCCS(=O)(=O)O]

Compound 3223

Myoglobin/Trypsin digest: 3223 Pk area/RG Pk area=1.1.

Bacteriorhodopsin/Chymotrypsin digest: BR was boiled with 3223 before adding chymotrypsin; 3223 Pk area/RG Pk area=1.1.

Solubility potentially limited in aqueous solutions; 0.5% solution was milky and generated a jelly top phase after centrifugation. Degradation rate is low:

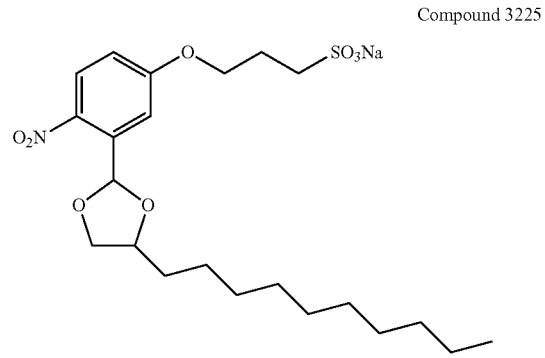

Compound 3225

Myoglobin/Trypsin digest: 3225 Pk area/RG Pk area=1.1.

Bacteriorhodopsin/Chymotrypsin digest: BR was boiled with 3225 before adding chymotrypsin; 3225 Pk area/RG Pk area=0.9.

Not soluble in aqueous solutions. It was solubilized in DMSO to 10%. Degradation rate is low: slowly degrades in 0.5% TFA at 37° C. No thermolability was observed.

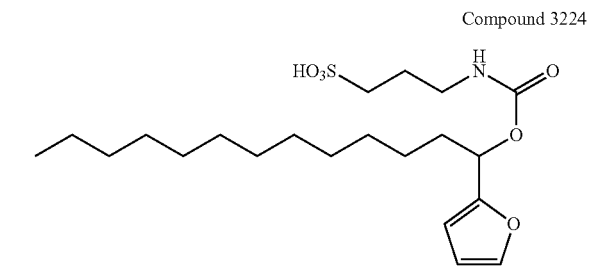 [SMILES: CCCCCCCCCCCCC(OC(=O)NCCCS(=O)(=O)O)c1ccco1]

Compound 3224

Myoglobin/Trypsin digest: 3224 Pk area/RG Pk area=1.3.

Bacteriorhodopsin/Chymotrypsin digest: 3224 Pk area/RG Pk area=0.74.

Moderate solubility in aqueous solutions: 0.25% solution. The solubility was dramatically improved after adding ACN to 20%: 2% solution was prepared. Excellent solubilization properties. BR was solubilized with 3224 at room temperature. Also see FIG. 15A and FIG. 15B.

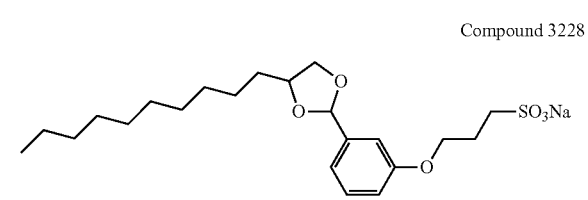

Compound 3228

Myoglobin/Trypsin digest: 3228 Pk area/RG Pk area=1.4.

Bacteriorhodopsin/Chymotrypsin digest: BR was boiled with 3228 before adding chymotrypsin; 3228 Pk area/RG Pk area=1.2.

Good solubility in aqueous solutions: easily dissolved to 1%. Degradation rate is low: 0.1%. See also FIG. 16A and FIG. 16B.

Compound 3236

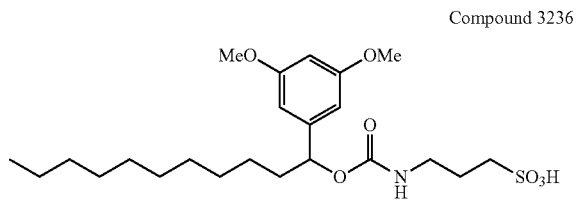 [SMILES: CCCCCCCCCCC(OC(=O)NCCCS(=O)(=O)O)c1cc(OC)cc(OC)c1]

Myoglobin/Trypsin digest: 3236 Pk area/RG Pk area=1.4.
Bacteriorhodopsin/Chymotrypsin digest: BR was boiled with 3236 before adding chymotrypsin; 3236 Pk area/RG Pk area=0.71.

Good solubilization in aqueous solutions: easily dissolved to 1%. Degradation rate is low: no degradation was observed with 0.1% solution in 0.5% TFA after 30 minutes of incubation at 37° C. or 5 minutes of boiling without TFA.

Compound 3237

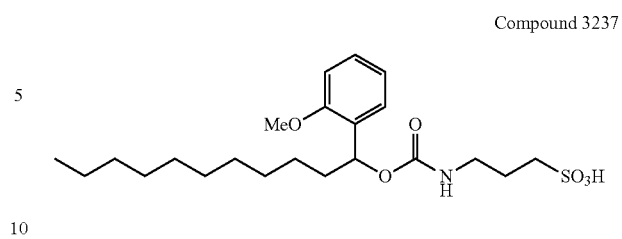

Myoglobin/Trypsin digest: 3237 Pk area/RG Pk area=1.4.
Bacteriorhodopsin/Chymotrypsin digest: BR was boiled with 3237 before adding chymotrypsin; 3237 Pk area/RG Pk area=1.

Moderate solubility: 0.5% solution. Moderate degradation was observed after 30 minutes incubation in 0.5% TFA at 37° C.

Compound 3266

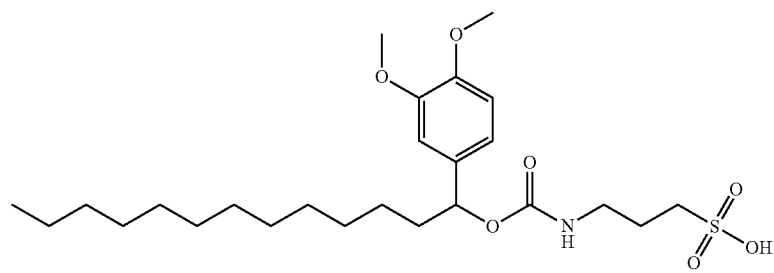

Myoglobin/Trypsin digest: 3266 Pk area/RG Pk area=1.2.
Bacteriorhodopsin/Chymotrypsin digest: 3266 Pk area/RG Pk area=N.D.

Excellent solubility: instantly dissolved to 2% in 50 mM ammonium bicarbonate. Acid-labile (0.1% solution degraded in 0.5% TFA within 30 minutes) but not thermolabile (remained intact after 5 minutes at 95° C.). Also see FIG. 17A and FIG. 17B.

| Hydrolytic stability in 50 mM Ammonium Bicarbonate | |
|---|---|
| Surfactant conc. | ½-life (hr) |
| 0.025% | >> |
| 0.25% | >> |
| 1% | >> |

>> = compound 100% stable over course of experiment.

Compound 3267

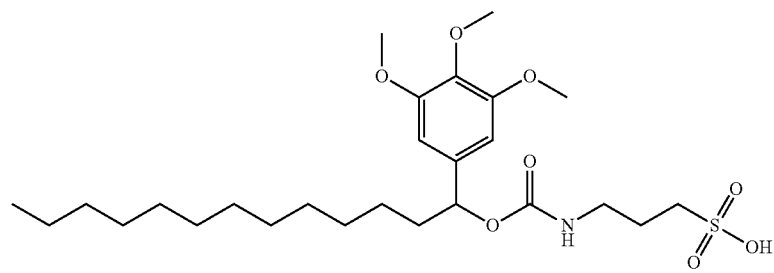

Myoglobin/Trypsin digest: 3267 Pk area/RG Pk area=0.9.

Bacteriorhodopsin/Chymotrypsin digest: BR was solubilized without boiling prior to adding chymotrypsin; 3267 Pk area/RG Pk area=N.D.

Excellent solubility: dissolved to 2% in 50 mM ammonium bicarbonate. Did not degrade in 0.5% TFA or by boiling-acid- and thermolabile.

| Hydrolytic stability in 50 mM Ammonium Bicarbonate Surfactant conc. ½-life (hr) | |
|---|---|
| 1% | >> |

>> = compound 100% stable over course of experiment.

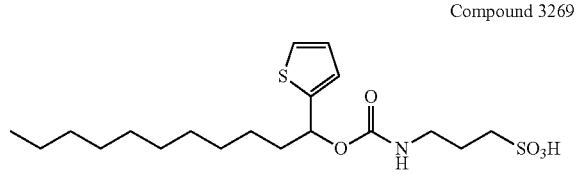 [SMILES: CCCCCCCCCCC(OC(=O)NCCCS(=O)(=O)O)c1cccs1]

Compound 3269

Myoglobin/Trypsin digest: 3269 Pk area/RG Pk area=1.

Bacteriorhodopsin/Chymotrypsin digest: BR was solubilized without boiling prior to adding chymotrypsin; 3269 Pk area/RG Pk area=N.D.

Acceptable solubility: prepared 1% solution.

| Hydrolytic stability in 50 mM Ammonium Bicarbonate Surfactant conc. ½-life (hr) | |
|---|---|
| 0.03% | 7 |
| 1% | 135 |

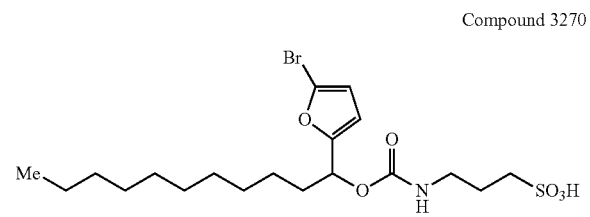 [SMILES: CCCCCCCCCCC(OC(=O)NCCCS(=O)(=O)O)c1ccc(Br)o1]

Compound 3270

Myoglobin/Trypsin digest: 3270 Pk area/RG Pk area=0.8.

Bacteriorhodopsin/Chymotrypsin digest: BR was solubilized without boiling prior to adding chymotrypsin; 3270 Pk area/RG Pk area=N.D.

Moderate solubility: prepared 0.5% 3270.

| Hydrolytic stability in 50 mM Ammonium Bicarbonate Surfactant conc. ½-life (hr) | |
|---|---|
| 0.025% | 6.5 |
| 1% | 40 |

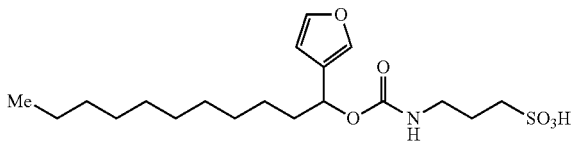

Compound 3271

Myoglobin/Trypsin digest: 3271 Pk area/RG Pk area=0.9.
Bacteriorhodopsin/Chymotrypsin digest: 3271 Pk area/RG Pk area=N.D.

Good solubility (1% solution was easily prepared). Just partially acid-labile, thermostable (TLC analysis). Also see FIG. 18A and FIG. 18B.

| Hydrolytic stability in 50 mM Ammonium Bicarbonate Surfactant conc. ½-life (hr) | |
|---|---|
| 0.025% | >350 |
| 1% | >> |

>> = compound 100% stable over course of experiment.

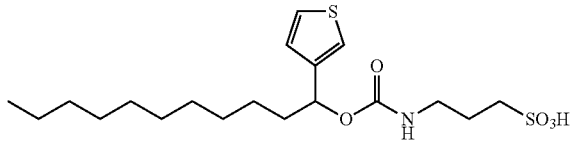

Compound 3273

Myoglobin/Trypsin digest: 3273 Pk area/RG Pk area=0.75.
Bacteriorhodopsin/Chymotrypsin digest: BR was solubilized without boiling prior to adding chymotrypsin; Pk area/RG Pk area=N.D.

Good solubility (1% solution was easily prepared). All the properties are similar to 3271. Just partially acid-labile, thermostable

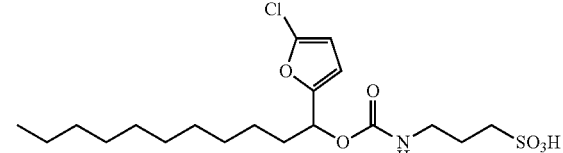

Compound 3274

Myoglobin/Trypsin digest: 3274 Pk area/RG Pk area=1.
Bacteriorhodopsin/Chymotrypsin digest: BR was solubilized without boiling prior to adding chymotrypsin; 3274 Pk area/RG Pk area=N.D.

Moderate solubility: prepared 1% solution (at room temperature). Acid- and thermolabile.

| Hydrolytic stability in 50 mM Ammonium Bicarbonate Surfactant conc. ½-life (hr) | |
|---|---|
| 0.025% | ~6 |
| 1% | N.D. |

N.D. = biphasic curve uninterruptible.

Compound 3275

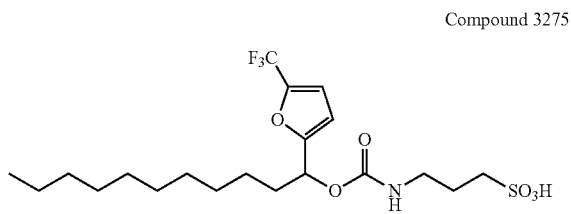 [SMILES: CCCCCCCCCCC(OC(=O)NCCCS(=O)(=O)O)c1ccc(C(F)(F)F)o1]

Myoglobin/Trypsin digest: 3275 Pk area/RG Pk area=0.2.
Bacteriorhodopsin/Chymotrypsin digest: BR was solubilized without boiling prior to adding chymotrypsin; 3275 Pk area/RG Pk area=N.D.

Acceptable solubility: easily prepared 1% solution. Fully acid- and thermostable at the tested conditions

| Hydrolytic stability in 50 mM Ammonium Bicarbonate Surfactant conc. ½-life (hr) | |
|---|---|
| 0.025% | >300 |
| 1% | >> |

>> = compound 100% stable over course of experiment

Example 13. Protocol for Trypsin-Assisted Protein Digestion for Proteins in Solution Analyzed by Off-Line 2D-LC-MS/MS A surfactant-assisted in-solution digestion was compared with a urea-assisted in-solution digestion and with urea+surfactant assisted in-solution digestion to demonstrate the increase in protein coverage one can obtain by either substituting the surfactant for urea as a denaturant, or by supplementing urea with a surfactant when digesting a complex mixture. To demonstrate the surfactants efficacy as a solubilant and denaturant, three separate samples of Mouse heart membrane protein extract were solubilized and digested in separate reactions with surfactant compound 3211 as denaturant, Urea as denaturant and Urea+surfactant compound 3211 together as denaturant. Each digest was separately analyzed by off-line 2D-LC-MS/MS and the protein coverage from each condition was compared.

Surfactant-Aided Protocol.

Protein from a 500 μg sample of mouse heart membrane extract was solubilized in 60 μL of 0.2% surfactant 3211 (in 50 mM ammonium bicarbonate), then diluted to a volume of 280 μL with 50 mM ammonium bicarbonate. After dilution, 3 μL of 1M DTT was added and the sample was incubated for 20 minutes at 56° C. DTT reduction was followed by alkylation with 18 μL 0.5M iodoacetamide for 15 minutes at room temperature. After alkylation, an additional 3 μL of 1% surfactant 3211 was added followed by 17 μg of trypsin (1.0 μg/μL in 50 mM ammonium bicarbonate) and the mixture was digested for 3 hours at 37° C.

Urea-Aided Protocol.

Protein from a 500 μg sample of mouse heart membrane extract was solubilized in 45 μL of 8M urea, and then diluted to a volume of 280 μL with 50 mM ammonium bicarbonate. After dilution, 3 μL of 1M DTT was added and the sample was incubated for 20 minutes at 56° C. DTT reduction was followed by alkylation with 18 μL of 0.5M iodoacetamide for 15 minutes at room temperature. After alkylation, 17 μg of trypsin (1.0 μg/μL in 50 mM ammonium bicarbonate) was added and the mixture was digested overnight at 37° C.

Urea+Surfactant-Aided Protocol.

Protein from a 500 μg sample of mouse heart membrane extract was solubilized in the mixture of 45 μL 8M Urea/60 μL 0.2% compound 3211, then diluted to a volume of 280 μL with 50 mM ammonium bicarbonate. After dilution, 3 μL of 1M DTT was added and the sample was incubated for 20 minutes at 56° C. DTT reduction was followed by alkylation with 18 μL 0.5M iodoacetamide for 15 minutes at room temperature. After alkylation, an additional 3 μL of 1% surfactant 3211 was added followed by 17 μg of trypsin (1.0 μg/μL in 50 mM ammonium bicarbonate) and the mixture was digested for 3 hours at 37° C.

Off-line 2D-LC-MS/MS analysis. Each digestion sample was divided into three aliquots, adjusted to 0.5% TFA and solid phase extracted using a 4 mg Varian Spec SPE tip. Triplicate elutions were combined and evaporated to dryness (speed-vac) and dissolved in ~100 μl of 0.1% TFA and loaded on to an Agilent Zorbax 300-SCX column (3.0×50 mm, 5-micron). Solvents: A=0.03% (v/v) formic acid/5% acetonitrile; B=0.03% (v/v) formic acid/5% acetonitrile/ 0.5M sodium chloride. After loading peptides were eluted by gradient elution on an HP1050 HPLC monitored by absorbance at 214 nm, eluted peptides were fractionated into 1 mL fractions (~20 fractions per condition). Salt gradient: flow rate=1 mL/min; Initial conditions: 0% B, T=0-8 minutes 100% B, T=8-20 minutes 100% B. Each SCX fraction was concentrated to dryness then dissolved in 0.1% TFA/5% acetonitrile and desalted using a 100 μL OMIX SPE column eluting with 100 μL of 70% acetonitrile (0.1% TFA). Eluants were evaporated to dryness and re-suspended in 0.1% TFA/ 5% acetonitrile for 2nd dimension LC-MS using an Agilent 1100 series LC/MSD Trap SL spectrometer.

Discussion Equal amounts of membrane protein extract were solubilized under three different conditions: with urea, with surfactant, or with a urea/surfactant mix. All the protein mixtures were digested with trypsin. Proteins solubilized with urea were digested overnight. Proteins solubilized with surfactant or the urea/surfactant mix were digested for 3 hours. The digests were fractionated on an SCX column (strong cation exchange). Each SCX fraction was analyzed in the second dimension with reverse phase LC-MS/MS.

As a accepted solubilizing denaturant, urea is commonly used to extend the coverage of proteomic coverage. In this experiment, 477 different proteins were identified by using urea as a denaturant. Digests that included a surfactant (with and without urea) extended the protein coverage by approximately 335 proteins that were not observed in the digest using urea only. This amounts to a 70% increase in protein coverage by using the surfactant as both an alternative and complimentary solubilizer/denaturant.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

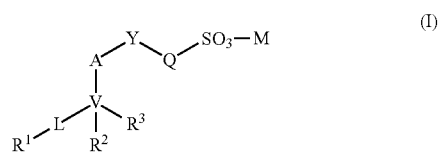

wherein:
Q is $(C_1-C_6)$alkyl;
Y is —O—C(=Z)—X—;
A is a direct bond;
Z is O or S;
X is NH;
V is C;
M is H, an alkali metal, or tetra$(C_1-C_{20})$alkylammonium;
L is —X—C(=Z)—X— or a direct bond;
$R^1$ is $(C_4-C_{20})$alkyl or $(C_2-C_{20})$alkenyl; and
$R^2$ and $R^3$ are each independently $(C_1-C_{20})$alkyl;
wherein any alkyl or alkenyl is optionally substituted with 1, 2, 3, 4, or 5 $(C_1-C_{20})$alkyl, $(C_2-C_{20})$alkenyl, $(C_2-C_{10})$alkynyl, $(C_3-C_{10})$cycloalkyl, $(C_1-C_{20})$alkoxy, halo, hydroxyl, —$CO_2R^x$, $N(R^x)_2$, mercapto, $(C_1-C_{20})$alkylthio, $(C_6-C_{16})$aryl, $(C_6-C_{30})$arylthio, trifluoromethyl, heteroaryl, or heterocycle groups; provided that Q is not substituted with $CO_2H$; and
each $R^x$ is independently H, $(C_1-C_6)$alkyl, $(C_6-C_{16})$aryl, or $(C_1-C_6)$alkyl-$(C_6-C_{16})$aryl.

2. The compound of claim 1, wherein Q is $(C_2-C_3)$alkyl.
3. The compound of claim 2, wherein Q is substituted with hydroxy.
4. The compound of claim 1, wherein Z is O.
5. The compound of claim 1, wherein M is H or Na.
6. The compound of claim 1, wherein L is a direct bond.
7. The compound of claim 1, wherein $R^1$ is $(C_4-C_{20})$alkyl.
8. The compound of claim 1, wherein $R^1$ is $(C_{10}-C_{14})$alkyl.

9. The compound of claim 1, wherein $R^2$ and $R^3$ are each $(C_1-C_6)$alkyl.
10. The compound of claim 1, wherein $R^2$ and $R^3$ are each methyl.
11. The compound of claim 1, wherein:
Q is $(C_2-C_3)$alkyl, which is unsubstituted or substituted with hydroxy;
Z is O;
M is H or Na;
L is a direct bond;
$R^1$ is unsubstituted $(C_4-C_{20})$alkyl; and
$R^2$ and $R^3$ are each unsubstituted $(C_1-C_6)$alkyl.
12. The compound of claim 11, wherein:
$R^1$ is unsubstituted $(C_{10}-C_{14})$alkyl; and
$R^2$ and $R^3$ are each methyl.
13. The compound of claim 1, wherein the compound is selected from:

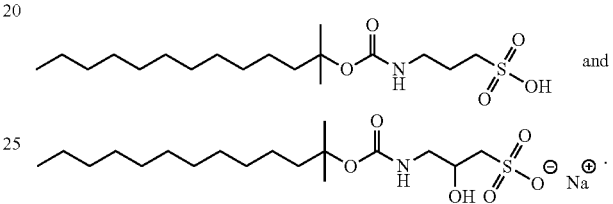

and

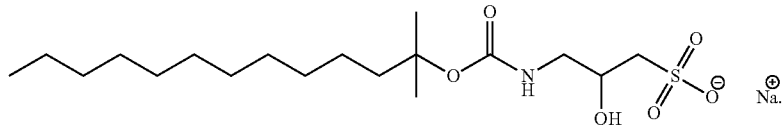

14. The compound of claim 1, wherein the compound is:

15. A composition comprising a gel and the compound of formula (I) of claim 1.
16. The composition of claim 15, further comprising at least one protein.

* * * * *